United States Patent
Ling et al.

(10) Patent No.: US 9,822,086 B2
(45) Date of Patent: Nov. 21, 2017

(54) PROCESS FOR THE PREPARATION OF VORTIOXETINE SALTS

(71) Applicant: Egis Gyogyszergyar Zrt., Budapest (HU)

(72) Inventors: Istvan Ling, Budapest (HU); Gyorgy Jeges, Vilonya (HU); Gyorgyi Kovanyine Lax, Budapest (HU); Balazs Volk, Budapest (HU); Peter Gregor, Szekesfehervar (HU); Jeno Peter Seres, Budapest (HU); Andras Dancso, Budapest (HU); Zoltan Varga, Budapest (HU); Eva Szabo, Budapest (HU)

(73) Assignee: EGIS GYOGYSZERGYAR ZRT., Budapest (HU)

(*) Notice: Subject to any disclaimer, the term of this patent is extended or adjusted under 35 U.S.C. 154(b) by 0 days.

(21) Appl. No.: 15/115,063

(22) PCT Filed: Jan. 30, 2015

(86) PCT No.: PCT/HU2015/000007
§ 371 (c)(1),
(2) Date: Jul. 28, 2016

(87) PCT Pub. No.: WO2015/114395
PCT Pub. Date: Aug. 6, 2015

(65) Prior Publication Data
US 2017/0114034 A1    Apr. 27, 2017

(30) Foreign Application Priority Data

Jan. 31, 2014  (HU) .................................. 1400044

(51) Int. Cl.
| C07D 295/08 | (2006.01) |
| A61K 31/495 | (2006.01) |
| C07D 295/096 | (2006.01) |
| C07C 55/07 | (2006.01) |
| C07C 59/265 | (2006.01) |
| C07C 65/10 | (2006.01) |
| C07C 55/08 | (2006.01) |
| C07C 309/29 | (2006.01) |
| C07C 53/10 | (2006.01) |
| C07C 55/10 | (2006.01) |

(52) U.S. Cl.
CPC .......... *C07D 295/096* (2013.01); *C07C 53/10* (2013.01); *C07C 55/07* (2013.01); *C07C 55/08* (2013.01); *C07C 55/10* (2013.01); *C07C 59/265* (2013.01); *C07C 65/10* (2013.01); *C07C 309/29* (2013.01); *C07B 2200/13* (2013.01)

(58) Field of Classification Search
CPC ........................ A61K 31/495; C07D 295/08
See application file for complete search history.

(56) References Cited

U.S. PATENT DOCUMENTS

| 8,664,225 B2 | 3/2014 | Moore et al. |
| 2011/0009422 A1 | 1/2011 | Moore et al. |
| 2016/0200698 A1 | 7/2016 | Song et al. |

FOREIGN PATENT DOCUMENTS

| CN | 103788019 A | 5/2014 | |
| CN | 103788020 A | 5/2014 | |
| WO | 2007/144005 A1 | 12/2007 | |
| WO | 2008/113359 A2 | 9/2008 | |
| WO | WO 2008/113359 * | 9/2008 | ........... A61K 31/495 |
| WO | 2015/035802 A1 | 3/2015 | |

OTHER PUBLICATIONS

International Search Report dated Nov. 2, 2015 issued in corresponding PCT/HU2015/000007 application (7 pages).
Written Opinion of the International Searching Authority dated Nov. 2, 2015 issued in corresponding PCT/HU2015/000007 application (8 pages).
English Abstract of CN 103788019 A published May 14, 2014.
English Abstract of CN 103788020 A published May 14, 2014.

* cited by examiner

Primary Examiner — Erich A Leeser
(74) Attorney, Agent, or Firm — Millen, White, Zelano & Branigan, P.C.

(57) ABSTRACT

The invention relates to an improved process for the preparation of pharmaceutical active ingredients and also to high purity salts and pharmaceutical compositions prepared by said process. More particularly the invention relates to an economical process for the preparation of the compound having the international non-proprietary name (INN) vortioxetine and the chemical nomenclature 1-[2-(2,4-dimethylphenylsulfanyl)-phenyl]-piperazine. Vortioxetine corresponds to the following Formula

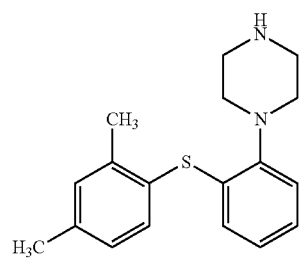

Still more particularly the invention relates to the preparation of high purity vortioxetine L-(+)-mandelate salt of the Formula IX, the conversion of this salt into other highly pure salts and also to the formulation of said salts.

28 Claims, 18 Drawing Sheets

XRD diffractogram of vortioxetine salicylate salt (1:1)

XRD diffractogram of vortioxetine hemioxalate salt

XRD diffractogram of vortioxetine L-malate salt (1:1)

XRD diffractogram of vortioxetine acetate salt (1:1)

REACTION SCHEME

PROCESS FOR THE PREPARATION OF VORTIOXETINE SALTS

TECHNICAL FIELD OF THE INVENTION

The invention relates to vortioxetine salts and polymorphs and a process for the preparation thereof. More particularly the invention is concerned with an economical process for the preparation of high purity vortioxetine mandelate of the Formula IX and the conversion thereof into other highly pure salts. The mandelate salt of the Formula IX is a salt of the compound having the INN vortioxetine of the chemical nomenclature 1-[2-(2,4-dimethyl-phenylsulfanyl)-phenyl]-piperazine.

STATE OF THE ART

It is known that 1-[2-(2,4-dimethyl-phenylsulfanyl)-phenyl]-piperazine having the INN vortioxetine is a pharmaceutical active ingredient having a combined serotonine reuptake inhibiting and 5-$HT_{1A}$ receptor partial agonist, 5-$HT_{1B}$ antagonist, 5-$HT_7$ antagonist mechanism of action. This active ingredient is suitable for the treatment of depression, general anxiety disease (GAD), panic disease and monomaniac disease.

Vortioxetine can also be used in a surprising way for the treatment of several other diseases. WO 2008/1113359 (EP 2142193) relates to the use of vortioxetine and pharmaceutically acceptable salts thereof for the treatment of pain. According to WO 2009/062517 vortioxetine is also useful in the treatment of difficulties in going to sleep.

According to WO 2012/025123 vortioxetine can be preferably used for the long-term treatment of diseases of the central nerval system.

Vortioxetine was described first by Ruhland et al in WO 03/029232, In said patent specification—among others—a broad range of phenyl piperazine derivatives, including vortioxetine, is described. Processes for the preparation of said compounds are disclosed and illustrated by means of examples. The patent specification is silent in disclosing the preparation and physical-chemical characteristics of vortioxetine. In one described process reference is made to vortioxetine as a compound prepared in an analogous manner. Vortioxetine is identified by mass spectrometrical analysis. The chromatographic purity of the product and the yield are disclosed. According to the process piperazine is coupled to p-nitro-phenyl-carbonate resin in the presence of N-methyl-maleinimide in dimethyl formamide as solvent. This product is reacted with $n^6$-1,2-dichloro-benzene-$n^5$cyclopentadienyl-Fe(II)-hexafluoro-phosphate on the presence of potassium carbonate. The N,N-disubstituted piperazine complex is reacted with dimethyl-thiophenol, then decomplexed by photolytic means, whereupon the product is removed from the resin in the presence of trifluoro acetic acid in dichloro methane as solvent. However this process is unsuitable for the preparation of a larger amount of the compound and can only be used for the synthesis of the compound library. In the patent specification a process for the preparation of analogues is also set forth; according to the method disclosed in prior art a 2-(phenyl-sulfanyl)-aniline derivative is prepared by reacting 2-fluoro-nitrobenzene with a thiophenol derivative and in the next step this product is reacted with N-(tert.butoxycarbonyl)-imino-di-acetic acid to yield the corresponding 3,5-dioxo-piperazine derivative. The product thus obtained is reduced with a borane/tetrahydrofurane complex in tetrahydrofurane as solvent and the corresponding (phenyl-sulfanyl)-phenyl-piperazine derivative is isolated in form of the hydrochloride salt with a yield of 31-100%. However the above process is only used for the preparation of analogous compounds but not for the preparation of vortioxetine.

In course of the development of the pharmaceutical compositions several crystalline salts and the crystalline base was prepared. The preparation of such crystalline salts and the crystalline base is disclosed in WO 2007/144005. In this patent publication the preparation of the crystalline base, the α-β-γ polymorphs of the hydrobromide salt and hydrates and solvates thereof and the following 10 new salts is described: hydrochloride, mesylate, fumarate, maleate, meso-tartarate, L-(+)-tartarate, D-(+)-tartarate, sulphate, phosphate and nitrate. Additionally highly water soluble salts are described in EP 2421534. These salts are explicitly for use in liquid pharmaceutical compositions.

In WO 2010/094285 the purification of vortioxetine hydrobromide via a crystalline isopropanol solvate is set forth. The inventors have surprisingly found that in course of the formation of the isopropanol solvate the impurities are eliminated or their amount is significantly reduced.

In the examples of WO 09/062517, WO 01/2025123 and WO 2007/144005 relating to the preparation of pharmaceutical compositions hydrobromide salts are used. Moreover claims 13 and 14 of WO 2007/144005 specifically relate to pharmaceutical compositions comprising vortioxetine hydrobromide.

In WO 2007/144005 two reaction variants are described for the preparation of vortioxetine starting from identical building stones. The desired compound is prepared from 2,4-dimethyl-thiophenol, 1,2-dihalogeno-benzene and protected or free piperazine in palladium catalysed homogenous phase reactions.

According to WO 02/01312573 1-halogeno-2,4-dimethyl-benzene and 2-halogeno-thiophenol are used as starting material.

The process disclosed in CN103788019 uses cheap starting materials and provides vortioxetine by a method which can be carried out in a relatively simple manner. Thus o-nitro-thiophenol is reacted with 2,6-dimethyl-chloro-benzene and the nitro compound of the Formula IV is reduced, or the key intermediate—namely 2-(2,4-dimethyl-phenyl-sulfanyl)-aniline of the Formula V is directly obtained by reacting 2,6-dimethyl-chloro-benzene with 2-amino-thio-phenol; the intermediate of the Formula V is transformed into vortioxetine of the Formula I in one step.

According to CN103788020 2-(2,4-dimethyl-phenylsulfanyl)-aniline of the Formula V is prepared by reacting 2-halo-nitro-benzene with 2,4-dimethyl-thiophenol of the Formula III and reducing the nitro compound of the Formula IV thus obtained.

According to both Chinese patent publications cited above the anilino derivative obtained is reacted with bis-(2-chloro-ethyl)-amine or bis-(2-bromo-methyl)-amine. On reproducing this reaction it has been found that the by-product of the Formula VIII is formed in an undesired high amount. This impurity has very similar properties to vortioxetine and the removal thereof is very difficult and expensive.

The processes disclosed in CN103788019 and CN103788020 are accompanied by the further disadvantage that during the preparation of the intermediate of the Formula IV a copper-containing catalyst and a very strong base are used and additionally light catalysis is applied. The use of the copper catalyst can contaminate the product and the residual solvents, the removal of the copper impurity increases the costs of the process. Moreover the copper catalyst is expensive and this is also an unfavourable factor. By using the reaction conditions set forth in said patent publications for the formation of the piperazine ring we failed to reproduce the preparation of vortioxetine.

In CN103936694 the process described already in the above Chinese patent publications (CN103788019 and CN103788020) is disclosed. Vortioxetine hydrochloride is prepared by reacting 2-(2,4-dimethyl-phenylsulfanyl)-aniline of the Formula V with bis-(2-chloroethyl)-amine hydrochloride and the vortioxetine base is set free in a separate step by alkaline treatment. This process has an important drawback because the solvents used are very detrimental to health. The 2-(2,4-dimethyl-phenylsulfanyl)-aniline is also prepared by reacting 2-halogeno-nitro-benzene with 2,4-dimethyl-thiophenol of the Formula III and reducing the nitro compound of the Formula IV thus obtained. According to the examples the reduction of the nitro compound of the Formula IV is carried out either by using iron chloride and an active carbon catalyst and as hydrogen source hydrazine hydrate, or by applying iron powder and concentrated hydrochloric acid. The drawback of the first method resides in the well-known carcinogenic properties of hydrazine hydrate, while the industrial scale use of the second method is unfavourably affected by the very aggressive properties of the metal exerted on the structural materials.

In pharmaceutical industry not only the industrial scale manufacturing process of the active ingredient but also the selection of the suitable salt is essential. It is a fundamental requirement that the product manufactured in a reproducible manner should be chemically pure and morphologically uniform. Only such products meet the high requirements of pharmaceutical industry. It is namely well-known that various salts and polymorphs have considerably different properties e.g. dissolution speed, bioavailability, chemical stability, filtration and drying properties, solubility, tableting characteristics.

From the point of view of the economy an industrial scale manufacturing process is very important. A suitable process has to yield a morphologically uniform salt free from impurities in a readily reproducible way. An active ingredient is regarded as morphologically uniform if the polymorphism thereof is a certain crystalline form rather than a mixture of more crystalline forms. The morphologically uniform nature of the active ingredient is a basic requirement of modern pharmaceutical industry because different polymorphs have different properties (e.g. flowability, density, tableting characteristics) which affect the manufacturing process and the quality of the product. Moreover if the polymorphism changes in the ready-for-use pharmaceutical composition or during the storage, the delivery of the active ingredient is significantly influenced. This exerts an effect on the efficiency of the active ingredient and this cannot be tolerated. For this reason not only the uniform morphology but also the uniform polymorphology—i.e. morphological stability—are highly important, at least during the complete storage time of the pharmaceutical composition.

It clearly appears from the state of the art that from the known salts the hydrobromide and particularly the β polymorph thereof is the most suitable for the preparation of solid pharmaceutical compositions. However the use of the hydrobromide salt constitutes a compromise because the hydrobromide and hydrochloride salts are generally very corrosive, For this reason in course of the preparation of the active ingredient these active ingredients may attack the tools and the pressing surfaces may become uneven, in a worse case the tablet press seizes. As a result thereof the pressing strength will not be uniform which deteriorates the quality of the tablets. Additionally due to the corrosion metal salts (e.g. iron halides) may get into the pharmaceutical compositions which are transformed into oxides during storage and this can cause discoloration of the composition.

It is the object of the present invention to prepare vortioxetine from easily available nitro-halo-benzene derivatives by using dimethyl thiophenol under more preferable reaction conditions than those disclosed in the Chinese patent publications, whereby the formation of impurities is suppressed or said impurities are removed by a synthetic method. It is a further object of the invention to prepare high purity vortioxetine or vortioxetine salts starting from nitro-halo-benzene derivatives. It is a still further object of the present invention to prepare new high purity vortioxetine salts which have advantageous stability and physical-chemical properties, is chemically stable and suitable for the preparation of stable pharmaceutical compositions and can be manufactured on industrial scale in a reproducible manner. According to the state of the art the hydrobromide salt of vortioxetine is the most suitable salt or the reparation of solid pharmaceutical compositions. Thus it is a still further object of the present invention to prepare salts or salt polymorphs, respectively, which are at least as stable and at least as suitable for use in pharmaceutical compositions as the hydrobromide salt of vortioxetine. Thus the problems discussed above are overcome. According to EP2439201 the vortioxetine hydrobromide salt is purified as a hydrobromide isopropanol solvate. However when during the preparation of the hydrobromide salt alcohols are used, alkyl bromides can contaminate the product. It is known that alkyl bromides are genotoxical substances and therefore—depending on the dose of the active ingredient—the amount of said impurities is to be reduced to an order of magnitude of ppm.

OBJECT OF THE INVENTION

It is the object of the present invention to provide a synthetic process which is more economical than the known procedures, uses crystalline and/or easily purifiable intermediates, can be carried on industrial scale and yields high purity vortioxetine salts or vortioxetine base.

The term "high purity salts" as used in the present patent specification relates to vortioxetine having a purity higher than 99.5% or salts thereof containing said base.

The product according to the present invention can also be characterized with a content lower than 0.5%, preferably lower than 0.2% of the impurity of the Formula VIII.

The above object can be achieved by reacting 2-(2,4-dimethyl-phenylsulfanyl)-aniline of the Formula V with a bis-(halogenoalkyl)-amine of the general Formula VI and thereafter separating the L-(+)-amygdalic acid salt of vortioxetine of the Formula IX from the reaction mixture. It has been surprisingly found that—contrary to the separation of the other salts—the amygdalic acid salt contains a very small amount of impurity, The L-(+)-amigdalic acid salt thus obtains contains in a surprising manner less than 0.5%, preferably less than 0.2% of the impurity of the Formula VIII, measured by the HPLC method described below.

The above object is achieved by the following process: the compound of the Formula V is reacted with a compound of the general Formula VI (wherein X stands for chlorine, bromine, iodine, OMs (methanesulfonyloxy), OTs (p-toluenesulfonyloxy) or hydroxyl; $H_nA$ represents an organic or inorganic mono- or polybasic acid and is the number of the hydrogen atoms, preferably 1, 2 or 3), whereupon the product obtained is converted into the L-(+)-mandelic acid salt of vortioxetine. From the salt obtained optionally the base is set free and/or the salt is optionally converted into another salt of the general Formula VII (wherein H$_n$A stands for a mono- or polybasic organic or inorganic acid; n is 1, 2 or 3 and A represents an acid residue ion).

According to a further aspect of the present invention there are provided morphologically uniform salts of vortioxetine of the Formula I formed with salicylic acid, citric acid, malonic acid, oxalic acid, L-malic acid, benzenesulfonic acid, acetic acid, succinic acid or L-mandelic acid, particularly the vortioxetine L-(+)-mandelate of the Formula IX, the vortioxetine monooxalate of the Formula X and the vortioxetine hemicitrate of the Formula XI.

According to the present invention there are provided morphologically uniform salts of vortioxetine formed with salicylic acid, citric acid, malonic acid, oxalic acid, L-malic acid, benzenesulfonic acid, acetic acid, succinic acid or L-mandelic acid which have a purity above 99.5%, preferably more than 99.8% measured by HPLC method and contain less than 0.5%, preferably less than 0.2% of the impurity of the Formula VIII. Such high purity salts which are of a purity above 99.5%, preferably above 99.8% and contain less than 0.5%, preferably less than 0.2% of the impurity of the Formula VIII can be preferably prepared by the process of the present invention.

According to the present invention morphologically uniform salts can be prepared.

DETAILED DESCRIPTION OF THE INVENTION

The key feature of the present invention is that a compound of the Formula V is reacted with a compound of the general Formula VI (wherein X stands for chlorine, bromine, iodine, OMs/methanesulfonyloxy/, OTs/p-toluenesulfonyloxy/ or hydroxyl; H$_n$A represents an organic or inorganic mono- or polybasic acid and n is the number of the hydrogen atoms, preferably 1, 2 or 3), the thus obtained vortioxetine is transformed into salt with L-(+)-mandelic acid whereupon if necessary the base is set free from the salt obtained and/or a salt is converted into another salt of the general Formula VII (wherein H$_n$A stands for a mono- or polybasic organic or inorganic acid; n is 1, 2 or 3 and A represents an acid residue ion).

According to a preferred aspect of the invention H$_n$A stands for citric acid, oxalic acid or L-(+)-mandelic acid.

More particularly the present invention relates to the following process: a compound of the Formula V is reacted with a compound of the general Formula VI (wherein X stands for chlorine, bromine, iodine, methanesulfonyloxy, p-toluenesulfonyloxy or hydroxyl; H$_n$A represents an organic or inorganic mono- or polybasic acid and A is an acid residue, n is the number of the hydrogen atoms, preferably 1, 2 or 3), optionally in the presence of an acid binding agent, in an aprotic solvent or a mixture thereof and thereafter separating the vortioxetine base from the reaction mixture and converting same into a salt formed with L-(+)-mandelic acid. The separation can be carried out by isolating the base in solid form or by extracting the base from the reaction mixture as a solution. The latter embodiment of the process enables the preparation of the mandelic acid salt without separating the solid base.

More particularly there is provided a process which comprises reacting the compound of the Formula V with a compound of the general Formula VI (wherein X stands for chlorine, bromine, iodine, methanesulfonyloxy, p-toluenesulfonyloxy or hydroxyl; H$_n$A represents an organic or inorganic mono- or polybasic acid and A is an acid residue and n is the number of the hydrogen atoms, preferably 1, 2 or 3) optionally in the presence of an acid binding agent, in an aprotic solvent or a mixture thereof, and thereafter a) separating the vortioxetine base from the reaction mixture, dissolving the separated vortioxetine base in a dipolar aprotic solvent and converting into a salt with L-(+)-mandelic acid salt; or b) adding to the reaction mixture an apolar aprotic solvent, preferably an aromatic solvent and aqueous alkali, stirring the mixture, separating the phases and washing with water, if necessary drying the organic phase and isolating the mandelate salt by adding mandelic acid.

The high purity mandelate salt thus obtained has an active ingredient content higher than 99.5%, measured by HPLC and/or contains less than 0.5%, preferably less than 0.2% of the impurity of the Formula VIII, measured by HPLC. Thus salt can be either directly used as active ingredient of pharmaceutical compositions or can be converted into the base or another salt.

The reaction of the compounds of the Formula V and VI (wherein X and H$_n$A are as stated above) can be carried out also in the absence of an acid binder. According to a further form of realization of the process of the invention the reaction is performed in the presence of an acid binder. For this purpose organic or inorganic acid binders can be used, such as tertiary amines/e.g. triethyl amine (TEA), N,N-disopropyl-ethyl-amine/DIPEA), tributyl amine (TBA), N,N-dimethyl-ethyl amine/or aromatic amines e.g. pyridine and derivatives thereof. As inorganic acid binder alkali or alkaline earth metal carbonates or hydrocarbonates, preferably alkali carbonates, particularly potassium carbonate can be used.

As aprotic solvent aromatic or aliphatic hydrocarbons, ethers, acid amides, nitriles, esters or a mixture thereof can be used. As aromatic solvent e.g. toluene, xylene, or ethyl benzene; as aliphatic solvent e.g. pentane, hexane, cyclohexane, octane or petrolether; as ether e.g. aliphatic or cyclic ethers such as diethyl ether, diisopropyl ether, dibutyl ether, methyl-ter. butyl ether, diethylene glycol dimethyl ether, diethylene glycol moonoethyl ether; as acid amide carboxylic acid amides e.g. dimethyl- or diethyl formamide, dimethyl- or diethyl-acetamide or propionamide; urea derivatives e.g. 1,3-dimethyl-2-imidazolidinone (DMI), as ester e.g. esters of acetic acid or propionic acid formed with C$_{1-4}$ alcohols e.g. ethyl acetate, propyl acetate, ethyl propionate or butyl acetate can be used.

The reaction can also be carried out in a solvent mixture, namely a mixture of an aromatic and amide type solvent, particularly a mixture of toluene and DMI. The weight ratio of toluene and DMI is 5:1-1:5, preferably 2:1-1:2, more advantageously 1:1.

The process can be carried out at a temperature between 100° C. and 200° C., preferably 150° C. and 200° C., particularly at 170-180° C. One may work at the boiling point of the solvent or solvent mixture or in a closed apparatus.

According to a preferred form of realization of the process of the invention the vortioxetine base is isolated from the reaction mixture when the reaction is completed. The vortioxetine base may also be isolated by filtering and clarifying the reaction mixture, if necessary, removing the solvent partly or completely preferably by distilling off. To the residue alkaline water is added, the precipitated solid is filtered to yield vortioxetine base. Said base is isolated, dissolved in a dipolar aprotic solvent, e.g. in a ketone or nitrile type solvent, whereupon a calculated amount of L-(+)-mandelic acid is added, preferably as a solution formed with a dipolar aprotic solvent. One may proceed preferably by dissolving vortioxetine base in hot acetone and adding a calculated amount of L-(+)-mandelic acid dissolved in acetone. The precipitated vortioxetine-L-(+)-mandelate is filtered from the cooled mixture and if necessary the product is recrystallized from an aliphatic alcohol, preferably methanol or 2-propanol.

One may proceed still more preferably by reacting the compounds of the Formulae V and VI (wherein X and $H_nA$ are as stated above) preferably in a mixture of toluene and DMI (1,3-dimethyl-2-imidazolidinone), most advantageously in a 1:1 mixture of toluene and DMI under reflux or in a closed vessel at 150-200° C., advantageously at 170-180° C., for a period of 6-20 hours, preferably 9-15 hours. The reaction mixture can be worked up by filtering and clarifying (with charcoal), distilling off the toluene from the reaction mixture and treating the residual solution with alkaline water. The solid is separated, dissolved in hot acetone and a calculated amount of L-(+)-mandelic acid is added. Thus the compound of the Formula IX is obtained.

According to a further preferred form of realization of the process of the present invention the vortioxetine base is isolated from the reaction mixture after the reaction has been completed. The base can be isolated by adding an apolar aprotic solvent, preferably an aromatic solvent, more advantageously toluene and alkaline water. The organic phase is separated and the vortioxetine-L-(+)-mandelate is precipitated from the solution of the vortioxetine base by adding L-(+)-mandelic acid. The salt is filtered and if necessary recrystallized from an aliphatic alcohol, preferably methanol or 2-propanol.

One may proceed still more preferably by reacting the compounds of the Formulae V and VI (wherein X and $H_nA$ are as stated above) preferably in a mixture of toluene and DMI (1,3-dimethyl-2-imidazolidinone), particularly in a 1:1 mixture of an aromatic solvent, preferably toluene and DMI, under reflux or in a closed vessel, at 150-200° C., preferably at 170-180° C. for a period of 6-20 hours, preferably 9-15 hours. The reaction mixture can be worked up by adding an apolar aprotic solvent, preferably an aromatic solvent, particularly toluene and treating the mixture thus obtained with alkaline water. The phases of the two-layer mixture thus obtained are separated. The organic phase which contains the vortioxetine base is dried, if necessary, heated to 50-100° C., preferably 50-80° C., particularly 55-65° C., whereupon a calculated amount of L-(+)-mandelic acid is added, the mixture is allowed to cool and the precipitated crystals are filtered and dried.

One may proceed most preferably by reacting the compounds of the Formulae V and VI (wherein X and $H_nA$ are as stated above) preferably in a mixture of toluene and DMI (1,3-dimethyl-2-imidazolidinone), most preferably in a 1:1 mixture of toluene and DMI under reflux or in a closed vessel, at a temperature of 150-200° C., preferably 170-180° C. for 6-20 hours, preferably 9-15 hours. The reaction mixture may be worked up by adding a 2-15 fold, preferably 3-12 fold, particularly 5-fold amount of toluene—related to the volume of the reaction mixture—and treating the mixture obtained with alkaline water. The layers of the two-phase mixture obtained are separated. The organic phase which contains the vortioxetine base is dried, if desired, warmed to 50-100° C., preferably to 50-80° C., particularly to 55-65° C., whereupon a calculated amount of with L-(+)-mandelic acid is added, the mixture is allowed to cool, the precipitated crystals are filtered and dried. If necessary the product is recrystallized from a protic solvent, preferably ethanol or 2-propanol in order to obtain a product which meets the requirements of pharmaceutical industry.

The HPLC purity of the L-(+)-mandelic acid salt of the Formula IX thus obtained is higher than 99.5%. This L-(+)-mandelic acid salt contains less than 0.5%, preferably less than 0.2% of the impurity of the Formula VIII.

If the vortioxetine formed in the reaction is separated in form of another salt rather than the mandelic acid salt, the purity of the product does not comply with pharmaceutical requirements, On replacing mandelic acid by other acids in course of the working up of the reaction mixture the results obtained are summarized in the following Table:

| Acid used | Product | HPLC purity |
|---|---|---|
| L-(+)-mandelic acid | L-(+)-mandelic acid salt | 99.9% |
| Oxalic acid | monooxalate salt | 97.85% |
| Citric acid | hemicitrate salt | 98.93% |
| HBr | hydrobromide salt | 97.72% |

The salt formed with mandelic acid can be used for the preparation of high purity vortioxetine base or highly pure salts. In this case one may proceed by setting free the vortioxetine base from the mandelic acid salt and converting the base into the desired salt.

The base suitable for the preparation of pure salts can be prepared by suspending the mandelic acid salt of vortioxetine in water, adding a solvent which is insoluble in water—e.g. dichloro methane—thereafter adding to the suspension sodium carbonate in an amount that the pH value of the aqueous phase should be alkaline. The mixture is vigorously stirred. The organic phase is separated, dried over magnesium sulphate and evaporated to dryness. The residual colourless oil is allowed to crystallize. The oil thus obtained is taken up in hot acetonitrile, the solution is cooled, the precipitated crystals are filtered, washed and dried.

One may also proceed by suspending the salt of vortioxetine formed with L-(+)-mandelic acid in dichloromethane, adding a 1 M sodium hydroxide solution and stirring the mixture until clear layers are obtained. The phases are separated, the organic layer is washed with water, dried and evaporated. The crystalline residue is suspended in water, filtered, washed with water and dried.

The pure vortioxetine base thus obtained is dissolved in a suitable solvent, preferably an aprotic solvent, particularly ethyl acetate or acetone, whereupon a 0.4-5.0 molar, preferably 0.5-3.0 molar amount of the acid is added per se or in form of a solution at a temperature between 0° C. and the reflux temperature of the solvent. If the salt is precipitated at the temperature of the addition or after cooling of the solution, the salt is filtered, if desired purified by recrystallization, and finally filtered, washed and dried. Should the salt not precipitate spontaneously the solvent is evaporated in vacuo, the residue is crystallized by adding a suitable solvent or solvent mixture, if desired the product is purified by recrystallization, finally filtered, washed and dried.

The purity of the salts thus obtained meets the requirements of pharmaceutical industry.

EXAMPLES

| Acid used | Product | HPLC puirity |
|---|---|---|
| Oxalic acid | monooxalate salt | 99.99% |
| Citric acid | hemicitrate salt | 99.90% |
| HBr | monohydrobromide salt | 99.81% |

According to the present invention the compound of the Formula V is prepared by reacting a compound of the general Formula II (wherein Z stands for fluorine, chlorine, bromine or iodine) with the compound of the Formula III in a dipolar aprotic solvent, preferably dimethyl formamide, at 60-120° C., preferably 80-120° C. The intermediate of the Formula IV is obtained with almost quantitative yield. In the second step of the process the nitro group of the compound of the Formula IV is reduced to an amino group. It is preferred to apply catalytic hydrogenation, advantageously on a palladium/charcoal catalyst. Hydrogenation is performed in a protic solvent, advantageously ethanol. The compound of the Formula V is obtained with an approximately quantitative yield.

According to a still further aspect of the present invention there are provided pharmaceutical compositions comprising a therapeutically efficient amount of a vortioxetine salt according to the present invention and if desired a pharmaceutically acceptable carrier. According to a still further aspect of the present invention there is provided the use of vortioxetine salts of the present invention as medicine and also the use of the vortioxetine salts according to the present invention for the preparation of pharmaceutical compositions.

The pharmaceutical compositions according to the present invention can be preferably prepared in the form of dosage units. Said dosage units can be put on the market in form of a package which contains separated amounts of the composition (e.g. packaged tablets, capsules, lozenges or ampoules containing a powder). The term "dosage unit" relates to the capsule, tablet, little bag, and lozenge and also to the package which contains the desired number of dosage units.

The pharmaceutical compositions according to the present invention can be preferably administered orally or parenterally. Oral compositions may be e.g. tablets, capsules, dragées, solutions, elixir, suspensions or emulsions. Parenteral compositions may be advantageously intravenously or intramuscularly administered injections or infusions The salts according to the present invention may be administered most advantageously in form of immediately release tablets.

The pharmaceutical compositions according to the present invention may contain conventional pharmaceutical carriers and/or auxiliary agents. As carrier e.g. magnesium carbonate, magnesium stearate, talc, sugar, lactose, pectin, dextrin, starch, gelatine, tragacanth, methyl cellulose, sodium carboxymethyl cellulose, low melting wax, PEG, cocoa butter etc. can be used. The wall of capsules often serves as carrier and in such cases no separate carrier is needed. Little bags and lozenge can also be used for oral administration. Particularly preferred solid oral compositions are the tablets, powders, capsules, pilules, little bags and lozenge.

The pharmaceutical compositions according to the present invention contain preferably morphologically uniform salts of vortioxetine formed with salicylic acid, citric acid, malonic acid, oxalic acid, L-malic acid, benzenesulfonic acid, acetic acid, succinic acid and L-amygdalic acid. It is preferred to use the following salts: vortioxetine salicylate (1:1) of the Formula XIII, monocitrate anhydrate of the Formula XX, monocitrate hydrate of the Formula XIV, hemicitrate of the Formula XI, malonate of the Formula XV, hemioxalate of the Formula XVI, monooxalate of the Formula X, malate of the Formula XVII, benzenesulfonate of the Formula XVIII, acetic acid salt of the Formula XIX, succinic acid salt of the Formula XII and L-(+)-mandelate of the Formula IX and polymorphs thereof. In the pharmaceutical compositions according to the present invention preferably vortioxetine salts can be used which have a HPLC purity higher than 99.5%, preferably higher than 99.8% and contain less than 0.5%, preferably less than 0.2% of the impurity of the Formula VIII. The following polymorph salts can be particularly advantageously used:

Polymorph of vortioxetine succinic acid (1:1) salt of the Formula XII which has the following characteristic X-ray powder diffraction peaks: 2θ (±0.2° 2θ): 11.33; 15.32; 17.03; 17.91; 23.44; 24;

polymorph of vortioxetine salicylate salt of the Formula XIII which has the following characteristic X-ray powder diffraction peaks lásd: 2θ (±0.2° 2θ): 13.73; 14.39; 16.60; 16.84; 18.61;

polymorph of vortioxetine monocitrate monohydrate (1:1) of the Formula XIV salt which has the following characteristic X-ray powder diffraction peaks: 2θ (±0.2° 2θ): 11.66; 13.89; 16.36; 17; 22.65; 24.09;

polymorph vortioxetine monocitrate anhydrate (1:1) salt of the Formula XX which has the following characteristic X-ray powder diffraction peaks: 2θ (±0.2° 2θ): 5.52; 12.38; 16.26; 16.61; 18.12; 20.89;

polymorph vortioxetine malonate salt of the Formula XV salt which has the following characteristic X-ray powder diffraction peaks: 2θ (±0.2° 2θ): 5.11; 10.46; 11.93; 15.21; 18.71; 20.42;

polymorph vortioxetine hemioxalate (2:1) salt of the Formula XVI salt which has the following characteristic X-ray powder diffraction peaks: 2θ (±0.2° 2θ): 15.43; 16.32; 16.96; 17.48; 22.85; 25.14;

polymorph vortioxetine L-malate (1:1) salt of the Formula XVII salt which has the following characteristic X-ray powder diffraction peaks: 2θ (±0.2° 2θ): 12.08; 13.4; 13.58; 16.97; 19.58; 24.26;

polymorph vortioxetine benzenesulfonate salt of the Formula XII which has the following characteristic X-ray powder diffraction peaks: 2θ (±0.2° 2θ): 14.79; 15.63; 17.61; 18.51; 19.54; 23.53;

polymorph vortioxetine acetate salt of the Formula XIX which has the following characteristic X-ray powder diffraction peaks: 2θ (±0.2° 2θ): 15.68; 22.44; 21.06; 13.08; 14.06; 18.26;

polymorph vortioxetine L-(+)-mandelate salt which has the following characteristic X-ray powder diffraction peaks: 2θ (±0.2° 2θ): 11.86; 13.29; 16.52; 16.93; 17.17; 23.46;

polymorph vortioxetine L-(+)-mandelate salt which has the following characteristic X-ray powder diffraction peaks: 2θ (±0.2° 2θ): 4.25; 11.69; 11.86; 13.29; 16.52; 16.93; 17.17; 18.47; 23.46; 24.29; 26.21;

polymorph vortioxetine hemicitrate (2:1) salt which has the following characteristic X-ray powder diffraction peaks: 2θ (±0.2° 2θ): 5.24; 13.79; 16.52; 17.31; 18.15; 20.35;

polymorph vortioxetine monooxalate (1:1) salt which has the following characteristic X-ray powder diffraction peaks: 2θ (±0.2° 2θ): 14.48; 17.8; 18.97; 20.38; 23.87; 27.57.

The pharmaceutical compositions according to the present invention contain preferably the polymorphs of the L(+)-mandelate, hemicitrate (2:1) and monooxalate salts the detailed process for the preparation thereof and their physical constants, XRD diffraction lines, melting point, NMR and other analytical data are disclosed. Stable pharmaceutical compositions which show a substantially constant dissolution during storage can be successfully prepared from these salts. According to the most preferred embodiment of the present invention the pharmaceutical composition contains the L-(+)-mandelate salt.

The pharmaceutical compositions according to the present invention may contain conventional auxiliary agents generally used in pharmaceutical industry. For this purpose e.g. fillers, glidants, antiadhesives, binders, disintegrants and lubricants can be used. The pharmaceutical compositions according to the present invention may contain the filler in an amount of 20-90% by weight, preferably 40-80% by weight, particularly 60-80% by weight, related to the weight of the pharmaceutical composition.

Any conventional filler can be used which does not effect the stability of the active ingredient. Thus organic polymers, e.g. microcrystalline cellulose, organic mono-, di- or polysaccharides or sugar alcohols e.g. lactose, mannitol, saccharose or inorganic salts e.g. tricalcium phosphate, calcium phosphate, calcium carbonate, or sodium chloride can be used. According to the most preferable embodiment of the invention the composition contains microcrystalline cellulose and/or mannitol as filler.

The pharmaceutical compositions according to the present invention may also contain disintegrants in order to accelerate the dissolution of the active ingredient. These substances generally swell in the presence of moisture and thereby break the tablet or capsule. Thus the active ingredient particles of the composition are set free. The disintegrants are generally organic polymers. The amount of the disintegrant in the composition is preferably 1-30% by weight, preferably 10-25% by weight, particularly 10-20% by weight. Any disintegrant generally used in pharmaceutical industry can be applied which does not react with the active ingredient. For this purpose preferably organic polymers e.g. cross-linked polyvinyl pyrrolidone (Poliplasdon, preferably Poliplasdon XL-10), microcrystalline cellulose, starch e.g. maize or wheat starch, pre-gelatinized starch, modified starch such as sodium carboxymethyl starch (Primojel) can be used. According to the most advantageous embodiment of the present invention the composition contains sodium carboxymethyl starch (Primojel).

The pharmaceutical compositions may contain a binder, if necessary. Conventional binders generally used in pharmaceutical industry can be applied which do not react with the active ingredient. Thus e.g. organic polymers such as hydroxypropylmethyl cellulose (hypromellose—referred to further on an HPMC) can be used, preferably in an aqueous solution which has a viscosity below 10000 mPas, preferably 3000-6000 mPas in a 2% aqueous solution at 20° C. Such HPMC types are e.g. Pharmacoat 603 or 606. For this purpose also polyvinyl pyrrolidone—referred to further on as PVP—can be used, preferably products having a lower polymerization degree, e.g. products designated as K-15 or K-30. It is highly preferred to use hydroxypropyl cellulose. The amount of the binder in the pharmaceutical composition is preferably 1-10% by weight, more preferably 1-5% by weight, particularly 1-3% by weight.

According to a preferred embodiment of the present invention the pharmaceutical compositions contain a lubricant and a glidant. The amount of the lubricant is 0.1-10% by weight, preferably 0.1-5% by weight, particularly 0.2-2% by weight, related to the weight of the pharmaceutical composition. As lubricant organic or inorganic substances generally used in pharmaceutical industry can be applied, e.g. stearates, preferably magnesium stearate, sodium stearyl fumarate, glyceryl behenate (e.g. Compritol 888) or inorganic substances such as talc.

Glidants generally used in pharmaceutical industry can be used such as talc, colloidal silica or tricalcium phosphate. The amount of the glidant may be 0.1-10% by weight, preferably 0.1-5% by weight, particularly 0.1-2% by weight.

The pharmaceutical compositions according to the present invention can be coated, if necessary. The coating may be aesthetical or functional e.g. it may modify dissolution. Any coating generally used in pharmaceutical industry can be used, e.g. organic polymers which do not react with the active ingredient. Preferably polymers are used which swell in water or are water soluble and thus promote the rapid dissolution of the active ingredient. As polymer preferably HPMC can be used, particularly a low viscosity product which has a viscosity lower than 10000 mPas, preferably 3000-6000 mPas in a 2% aqueous solution at 200. Such products are Pharmacoat 603 and 606. Polyvinyl pyrrolidone can also be used as coating material. According to a preferred embodiment of the present invention products having a lower polymerization degree are used, such as K-15 or K-30. The amount of the coating is preferably 1-10% by weight, more preferably 1-5% by weight, particularly 1-3% by weight, related to the weight of the pharmaceutical composition.

The vortioxetine salts according to the present invention may also be formulated as sustained release compositions. Such compositions are coated with a functional, preferably enterosolvent polymer coating, For this purpose e.g. methyl acrylate-methacrylic acid copolymers, cellulose acetate succinate, hydroxypropylmethyl cellulose phthalate, hydroxypropylmethyl cellulose acetate succinate (hipromellose acetate succinate), polyvinyl acetate phthalate (PVAP), methyl-methacrylate-methacrylic acid copolymers, shellac, cellulose acetate trimellitate or sodium alginate based polymers may be used.

The suppositories contain as carrier a low melting wax (e.g. a mixture of fatty acid glycerides, PEG or cocoa butter). The wax is melt and the active ingredient is homogenously distributed in the melt. The homogenous melt is poured in a conical mould of suitable size and solidified by cooling.

The pharmaceutical compositions according to the present invention may be most preferably capsules or tablets.

According to a further aspect of the present invention there is provided a process for the preparation of pharmaceutical compositions which comprises admixing a salt of vortioxetine formed with salicylic acid, citric acid, malonic acid, oxalic acid, L-malic acid, benzenesulfonic acid, acetic acid, succinic acid and L-mandelic acid, preferably vortioxetine monooxalate of the Formula X, vortioxetine L-(+)-mandelate of the Formula IX, vortioxetine hemicitrate of the Formula XI or votrtioxetine hydrobromide or a mixture of such salts with pharmaceutically acceptable solid or liquid diluents and/or auxiliary agents and bringing the mixture to a galenic form.

The pharmaceutical compositions according to the present invention can be prepared by well-known methods of pharmaceutical industry.

Tablets can be prepared by admixing the active ingredient with the desired amount of suitable carriers and pressing the mixture into tablets of the desired form and size. Capsules can be prepared by any method used for the preparation of tablets except that the powder mixture obtained or the granules and further auxiliary agents containing mixture or the homogenized mixture is not pressed to tablets but filled in capsules, preferably soft gelatine capsules.

The capsules and tablets can also be prepared by subjecting the active ingredient and a part of the auxiliary agents to dry (e.g. with a compactor) or wet granulation (e.g. by kneading, extrusion or fluid granulation), if necessary drying the granules thus obtained and pressing the mixture to tablets or filling into capsules.

One may proceed preferably admixing the morphologically uniform vortioxetine salt according to the present invention with one or more filler(s) and disintegrant(s), granulating the mixture thus obtained with a binder, preferably with an aqueous solution or suspension of a binder, drying the granules, if necessary spheronizing, regranulating and thereafter admixing with further auxiliary agents and pressing the mixture to tablets or filling into capsules.

Granulation can be carried out preferably in a fluid granulating apparatus. As filler most preferably mannitol and/or microcrystalline cellulose, while as binder preferably hydroxypropyl cellulose can be used. Before pressing to tablets the granules are admixed with further fillers, preferably microcrystalline cellulose and with lubricants, preferably magnesium stearate.

As active ingredient salts of vortioxetine formed with salicylic acid, citric acid, malonic acid, oxalic acid, L-malic acid, benzenesulfonic acid, acetic acid, succinic acid and L-amygdalic acid and hydrogen bromide, preferably the vortioxetine salicylate of the Formula XIII, the vortioxetine monocitrate anhydrate of the Formula XX, the monocitrate hydrate salt of the Formula XIV, the hemicitrate salt of the Formula XI, the malonate salt of the Formula XV, the hemioxalate salt of the Formula XVI, the monooxalate salt of the Formula X, the malate salt of the Formula XVII, the benzenesulfonate salt of the Formula XVIII, the acetic acid salt of the Formula XIX, the succinic acid salt of the Formula XII and the L-(+)-mandelate salt of the Formula IX or polymorphs thereof can be used.

According to the present invention preferably vortioxetine salts are used which have a HPLC purity higher than 99.5%, preferably higher than 99.8% and/or contain less than 0.5%, preferably less than 0.2% of the impurity of the Formula VIII. The following polymorph salts can be particularly advantageously used:

Polymorph vortioxetine L-(+)-mandelate salt which has the following characteristic X-ray powder diffraction peaks: 2θ (±0.2° 2θ): 4.25; 11.69; 11.86; 13.29; 16.52; 16.93; 17.17; 18.47; 23.46; 24.29; 26.21;

polymorph vortioxetine hemicitrate (2:1) salt which has the following characteristic X-ray powder diffraction peaks: 2θ (±0.2° 2θ): 5.24; 13.79; 16.52; 17.31; 18.15; 20.35;

polymorph vortioxetine monooxalate (1:1) salt which has the following characteristic X-ray powder diffraction peaks: 2θ (±0.2° 2θ): 14.48; 17.8; 18.97; 20.38; 23.87; 27.57.

The salts according to the present invention are morphologically stable. The particle size is adjusted to the desired preferred value by grinding, if necessary. For this purpose any grinding apparatus conventionally used in pharmaceutical industry is suitable. The vortioxetine salts according to the present invention can be ground in a vortex mill.

The vortioxetine salts according to the present invention can be ground preferably in a vortex mill, if necessary. Such active ingredients ground in a vortex mill are used in the pharmaceutical compositions according to examples 20-23. The data of some starting salts and those of the ground salts are summarized in the following table:

The polymorph character of the salts according to the present invention is stable and does not change in course of the grinding procedure.

The preparation of the tablets and capsules can be carried out by methods and equipment generally used in pharmaceutical industry. The selection of the apparatus and the optimization of the manufacturing procedures belong to the general knowledge of the person skilled in the art.

One may proceed particularly preferably by admixing 2-23% by weight, preferably 5-20% by weight—related to the weight of the composition—of the L-(+)-mandalate salt, the hemicitrate salt or the oxalate salt according to the present invention with 40-90% by weight, preferably 60-80% by weight of mannitol, 5-15% by weight, preferably 9-12% by weight of microcrystalline cellulose, 1-4% by weight, preferably 2-3% by weight of sodium carboxymethyl starch (Primojel) and granulating the mixture in a fluid granulating apparatus with a 3-10% by weight, preferably 4-8% by weight, particularly 6% by weight solution of hydroxypropyl cellulose (Klucel EXF). The granules thus obtained are dried in a fluidization apparatus, regranulated on a 1 mm oscillating sieve, whereupon the residual 2-5% by weight of microcrystalline cellulose and 0.5-1.5% by weight of magnesium stearate are added and the mixture thus obtained is pressed to tablets on a rotating tableting machine.

Powders are prepared by admixing the finely powdered active ingredient with the finely powdered carriers. The liquid compositions may be solutions, suspensions or emulsions which may also be suitable for sustained release delivery of the active ingredient. Aqueous solutions or aqueous propylene glycol solutions are preferred. Liquid compositions suitable for parenteral administration may be preferably prepared in form of an aqueous polyethylene glycol solution.

Aqueous solutions for oral administration can be prepared by dissolving the active ingredient in water and thereafter adding a suitable colouring agent, aroma, stabilizer and thickener. Orally administered aqueous suspensions may be prepared by suspending the active ingredient in water in the presence of a viscous material (e.g. a natural or artificial gum, methyl cellulose, sodium carboxymethyl cellulose or another known suspending agent).

Another group of the solid pharmaceutical compositions is transformed directly before use to a liquid composition which is orally administered into the organism. Said liquid compositions may be solutions, suspensions or emulsions, which may contain in addition to the active ingredient a colouring agent, an aroma, preservative, buffer, artificial or natural sweetener, dispersing agent, thickener etc.

The pharmaceutical compositions according to the present invention contain salts of vortioxetine formed with salicylic acid, citric acid, malonic acid, oxalic acid, L-malic

| Sample | Dispersing pressure [bar] | Characteristic particle size [μm] | | |
|---|---|---|---|---|
| | | $d_{10}$ | $d_{50}$ | $d_{90}$ |
| Vortioxetine-L-mandalate | 2.0 | 8.6 (±0.2%) | 41.5 (±0.2%) | 114 (±0.9%) |
| Vortioxetine-L-mandalate ground | 2.0 | 0.5 (±0.6%) | 2.1 (±0.2%) | 5.0 (±0.9%) |
| Vortioxetine-monooxalate | 2.0 | 2.0 (±0.3%) | 6.8 (±0.5%) | 21.14 (±0.7%) |
| Vortioxetine-monooxalate ground | 2.0 | 0.7 (±0.5%) | 2.2 (±0.7%) | 5.9 (±0.9%) |
| Vortioxetine-hemicitrate | 2.0 | 5.3 (±0.4%) | 25.9 (±0.7%) | 83.6 (±0.4%) |
| Vortioxetine-hemicitrate ground | 2.0 | 0.6 (±0.7%) | 2.9 (±0.2%) | 9.1 (±1.1%) |
| Vortioxetine-hydrobromide | 4.0 | 1.4 (±2.2%) | 10.8 (±1.6%) | 98.6 (±4.3%) |
| Vortioxetine-hydrobromide ground | 2.0 | 0.4 (±0.5%) | 2.1 (±0.7%) | 6.2 (±1.0%) | acid, benzenesulfonic acid, acetic acid, succinic acid and L-amygdalic acid, preferably the vortioxetine monooxalate of the Formula X, the vortioxetine-L-(+)-mandelate of the Formula IX, the vortioxetine hemicitrate of the Formula XI or a mixture thereof and compatible further pharmaceutical active ingredients.

According to the present invention there is provided the use of a salt of vortioxetine formed with salicylic acid, citric acid, malonic acid, oxalic acid, L-malic acid, benzenesulfonic acid, acetic acid, succinic acid and L-mandelic acid, preferably vortioxetine monooxalate of the Formula X, vortioxetine L-(+)-mandelate of the Formula IX and vortioxetine hemicitrate of the Formula XI as pharmaceutical active ingredient.

According to the present invention there is provided the use of the vortioxetine salts according to the present invention for the treatment or prophylaxis of melancholy, senile depressive disorders, general anxiety disease (GAD), panic disease, post-traumatic stress disorder, deterioration of cognitic functions related to depression, Alzheimer disease or residual symptoms of depression, chronical pain, eating disorders or compulsive eating disorders.

The most important embodiments of the present invention can be summarized as follows:

The invention relates to an improved process for the preparation of vortioxetine salts by reacting a compound of the Formula V with a compound of the general Formula VI (wherein X stands for chlorine, bromine, iodine, Oms/methanesulfonyloxy/, OTs/p-toluenesulfonyloxy/or hydroxyl; $H_nA$ represents an organic or inorganic mono- or polybasic acid, A is an acid residue and n is the number of the hydrogen atoms, preferably 1, 2 or 3). The vortioxetine base of the Formula I formed in the reaction is converted into a salt formed with L-(+)-mandelic acid of the Formula IX, if necessary the base is set free from the salt and/or converted into another salt of the general Formula VII (wherein $H_nA$ stands for a mono- or polybasic organic or inorganic acid; n is 1, 2 or 3 and A represents an acid residue ion).

The reaction of the compound of the Formula V and the compound of the general Formula VI (wherein X and $H_nA$ are as state above) is carried out in a solvent, preferably an aprotic solvent. As aprotic solvent aromatic or aliphatic hydrocarbons, ethers, acid amides, nitriles, esters or mixtures thereof can be used.

As aromatic solvent preferably toluene, xylene, ethyl benzene; as aliphatic solvent preferably pentane, hexane, cyclohexane, octane or petrol ether; as ether type solvent preferably aliphatic and/or cyclic ethers, particularly diethyl ether, diisopropyl ether, dibutyl ether, methyl tert. Butyl ether, diethylene glycol dimethyl ether, diethylene glycol monoethyl ether; as acid amide preferably carboxylic acid amides, particularly dimethyl or diethyl formamide, dimethyl or diethyl acetamide or propionamide; urea derivatives, preferably 1,3-dimethyl-2-imidazolidinone (DMI), esters preferably esters of acetic acid or propionic acid formed with $C_{1-4}$ alcohols, particularly ethyl acetate, propyl acetate, ethyl propionate, butyl acetate or a mixture thereof can be used. It is highly preferred to use as solvent a mixture of an aromatic and amide type solvent, still more advantageously a mixture of toluene and DMI wherein the ratio of toluene and DMI is 5:1-1:5, preferably 2:1-1:2, more advantageously 1:1.

The reaction of the compound of the Formula V and the compound of the general Formula VI (wherein X and $H_nA$ are as stated above) can be carried out preferably in the absence or in the presence of an organic or inorganic base.

If the reaction is carried out in the presence of an acid binding agent one may use an organic base preferably a tertiary amine and/or an aromatic amine. As tertiary amine preferably triethyl amine (TEA), N,N-diisopropyl ethyl amine (DIPEA), tributyl amine (TBA), N,N-dimethyl amine; as aromatic amine pyridine or a pyridine derivative can be used. As inorganic base preferably alkali or alkaline earth metal carbonates or hydrocarbonates, particularly potassium carbonate can be used. The reaction of the compound of the Formula V and the compound of the general Formula VI (wherein X and $H_nA$ are as stated above) can be performed at 100-200° C., preferably at 150-200° C., more advantageously at 170-180° C., at the boiling point of the solvent or solvent mixture or in a closed vessel. The reaction time is 6-20 hours, preferably 9-15 hours.

Once the reaction of the compound of the Formula V and the compound of the general Formula VI (wherein X and HnA are state above) is completed the vortioxetine base of the Formula I is isolated. This step can be carried out by evaporating the reaction mixture partially or completely, reacting the residue with an aqueous alkali, preferably ammonium hydroxide or a potassium hydroxide or a sodium hydroxides solution, more advantageously with an ammonium hydroxide solution, separating the precipitated vortioxetine base from the liquid phase, dissolving the base in a dipolar aprotic solvent, preferably in acetone and adding L-(+)-mandelic acid or a solution thereof formed with an aprotic solvent, isolating the salt thus obtained and optionally recrystallizing the L-(+)-mandelate salt of the Formula IX from a protic solvent, preferably ethanol or isopropanol.

The pure base can be prepared by suspending the crystalline vortioxetine L-(+)-mandelate of the Formula IX salt thus obtained in water, adding to the mixture a water non-miscible solvent, preferably an aromatic solvent, particularly toluene; or a halogenated solvent preferably dichloro methane; or an ether type solvent preferably diethyl ether or diisopropyl ether; and adding to the mixture thus obtained an inorganic base, e.g. an alkali or alkaline earth metal hydroxide or carbonate in an amount to make the aqueous phase alkaline, thereafter separating the organic phase, drying and evaporating the same.

If necessary the vortioxetine base of the Formula I thus obtained is
  a) recrystallized; or
  b) dissolved or suspended in a dipolar aprotic solvent, preferably a nitrile, ketone or ester type solvent, more advantageously in acetonitrile as nitrile; acetone as ketone; or ethyl acetate as ester and reacted with an organic acid, preferably salicylic acid, citric acid, malonic acid, oxalic acid, L-malic acid, benzenesulfonic acid, acetic acid, succinic acid and L-mandelic acid or a solution thereof formed with an organic solvent, or with an inorganic acid, preferably hydrogen bromide, still more preferably with citric acid, oxalic acid or a solution thereof formed with an organic solvent, preferably acetone or ethyl acetate or with aqueous hydrogen bromide and if necessary recrystallizing the salts thus obtained.

According to a still more preferred embodiment of the present invention the compound of the Formula V and the compound of the general Formula VI (wherein X and $H_nA$ are as stated above) are reacted in a 1:2-2:1, preferably 1:1 mixture of toluene and DMI, in the presence of potassium or sodium carbonate, preferably potassium carbonate, at 150-200° C., preferably 170-180° C. for 10-16 hours, preferably 12 hours. The reaction mixture is cooled, the precipitated inorganic salts are filtered off, washed, the united organic phases are evaporated toluene-free, the residue is poured into and an aqueous ammonium hydroxide solution, the precipitated vortioxetine base crystals of the Formula I are filtered off, and suspended in acetone. The suspension thus obtained is warmed to 60° C. and a calculated amount of L-(+)-mandelic acid dissolved in acetone is added. The mixture is cooled, the precipitated L-(+)-mandelate salt of the Formula IX is separated, optionally suspended in water, whereupon dichloro methane is added, the aqueous phase is made alkaline by adding potassium or sodium carbonate or an alkali hydroxide solution, preferably sodium or potassium hydroxide. The dichloro methane phase is separated, dried and evaporated. The vortioxetine base of the Formula I thus obtained is optionally a) allowed to crystallize or recrystallized from acetonitrile; or
b) the base is optionally crystallized or recrystallized, suspended and/or dissolved in a dipolar aprotic solvent, preferably acetone or ethyl acetate, to the mixture at 60° C. a calculated amount of an organic acid, preferably salicylic acid, citric acid, malonic acid, oxalic acid, L-malic acid, benzenesulfonic acid, acetic acid, succinic acid and L-mandelic acid, citric acid or oxalic acid dissolved in acetone or ethyl acetate or an aqueous hydrogen bromide solution is added and the corresponding vortioxetine salt is separated by cooling.

According to a particularly preferred embodiment of the present invention the compound of the Formula V and the compound of the general Formula VI (wherein X and $H_nA$ are as stated above) are reacted in a 1:2-2:1, preferably 1:1 mixture of toluene and DMI, in the presence of potassium or sodium carbonate, preferably potassium carbonate, in a closed vessel, at 150-200° C., preferably at 170-180° C. for 6-16 hours, preferably for 12 hours. To the warm reaction mixture a 2-15 volume, preferably 3-12 volume, more advantageously 5 volume excess of toluene—related to the volume of the reaction mixture—is added. The mixture thus obtained is cooled and made alkaline with an aqueous base preferably a sodium or potassium hydroxide solution, whereupon the organic phase is separated, if necessary dried, warmed to 50-100° C., preferably 50-80° C., particularly 55-65° C. To the mixture a calculated amount of L-(+)-amygdalic acid is added, the reaction mixture is allowed to cool, the precipitated crystals are filtered and dried.

The key intermediate of the synthesis—the compound of the Formula V—is prepared by reacting a nitro compound of the general Formula II (wherein Z is fluorine, chlorine, bromine or iodine) with the thiol of the Formula III and thereafter reducing the compound of the Formula IV into the amine of the Formula V.

According to a further aspect of the present invention there are provided new salts, preferably salts of vortioxetine base of the Formula I formed with salicylic acid, citric acid, malonic acid, oxalic acid, L-malic acid, benzenesulfonic acid, acetic acid, succinic acid and L-mandelic acid of a uniform morphology.

According to the present invention there are provided the salicylate, hemicitrate, monocitrate-monohydrate, monocitrate anhydrate, malonate, hemioxalate, monooxalate, L-malate, besylate, acetate, succinate and L-mandelate salts of vortioxetine.

According to the process of the present invention the pure base prepared from the mandelic acid salt is dissolved or suspended in a dipolar aprotic solvent whereupon the calculated amount of the corresponding acid is added. In the preparation of the above salts as solvent preferably acetone can be used.

According to a particularly preferred embodiment of the present invention there is provided vortioxetine L-(+)-mandelate of the Formula IX and a form thereof which has a HPLC purity higher than 99.5%, preferably higher than 99.8% and contains less than 0.5%, preferably less than 0.2% of the impurity of the Formula VIII.

According to the present invention there is provided a polymorph of vortioxetine L-(+)-mandelate of the Formula IX which has the following characteristic X-ray powder diffraction peaks: 2θ (±0.2° 2θ): 11.86; 13.29; 16.52; 16.93; 17.17; 23.46. but can also be characterized by the following salt which has the following characteristic X-ray powder diffraction peaks: 2θ (±0.2° 2θ): 4.25; 11.69; 11.86; 13.29; 16.52; 16.93; 17.17; 18.47; 23.46; 24.29; 26.21. The product can also be characterized by the following characteristic X-ray powder diffraction peaks disclosed in the following Table (relative intensity is > than 2%):

| Peak | 2θ (°) | d (Å) | Relative intensity (%) |
|---|---|---|---|
| 1 | 4.25 | 20.76 | 16 |
| 2 | 11.69 | 7.56 | 22 |
| 3 | 11.86 | 7.46 | 24 |
| 4 | 12.25 | 7.22 | 10 |
| 5 | 13.29 | 6.66 | 32 |
| 6 | 14.42 | 6.14 | 16 |
| 7 | 16.52 | 5.36 | 65 |
| 8 | 16.93 | 5.23 | 100 |
| 9 | 17.17 | 5.16 | 26 |
| 10 | 17.58 | 5.04 | 11 |
| 11 | 18.47 | 4.8 | 17 |
| 12 | 18.81 | 4.71 | 2 |
| 13 | 19.54 | 4.54 | 7 |
| 14 | 20.55 | 4.32 | 2 |
| 15 | 20.78 | 4.27 | 5 |
| 16 | 22.18 | 4 | 2 |
| 17 | 22.39 | 3.97 | 2 |
| 18 | 23.15 | 3.84 | 9 |
| 19 | 23.46 | 3.79 | 38 |
| 20 | 23.94 | 3.71 | 15 |
| 21 | 24.29 | 3.66 | 18 |
| 22 | 24.59 | 3.62 | 5 |
| 23 | 24.95 | 3.57 | 4 |
| 24 | 25.42 | 3.5 | 8 |
| 25 | 26.21 | 3.4 | 24 |
| 26 | 26.93 | 3.31 | 13 |
| 27 | 28.28 | 3.15 | 5 |
| 28 | 28.71 | 3.11 | 3 |
| 29 | 29 | 3.08 | 3 |
| 30 | 30.18 | 2.96 | 3 |
| 31 | 31.32 | 2.85 | 4 |
| 32 | 31.82 | 2.81 | 2 |
| 33 | 32.58 | 2.75 | 3 |
| 34 | 33.1 | 2.7 | 2 |
| 35 | 33.36 | 2.68 | 2 |

According to the present invention there is also provided a polymorph of vortioxetine hemicitrate (2:1) salt of the Formula XI which has the following characteristic X-ray powder diffraction peaks: 2θ (±0.2° 2θ): 5.24; 13.79; 16.52; 17.31; 18.15; 20.35. This salt can also be characterized by the following X-ray powder diffraction peaks: 2θ (±0.2° 2θ): 5.24; 13.79; 15.76; 16.52; 17.31; 17.65; 18.15; 20.35; 20.6; 21.00; 23.01. Said polymorph of the vortioxetine hemicitrate (2:1) salt of the Formula XI can also be characterized by the characteristic X-ray powder diffraction peaks disclosed in the following Table (relative intensities> than 2%):

| Peak | 2θ (°) | d (Å) | Relative intensity (%) |
|---|---|---|---|
| 1 | 5.24 | 16.85 | 100 |
| 2 | 10.26 | 8.61 | 36 |
| 3 | 10.5 | 8.41 | 10 |
| 4 | 10.94 | 8.08 | 9 |
| 5 | 11.43 | 7.74 | 14 |
| 6 | 12.1 | 7.31 | 16 |
| 7 | 13.02 | 6.8 | 21 |
| 8 | 13.79 | 6.41 | 93 |
| 9 | 14.28 | 6.2 | 8 |
| 10 | 14.67 | 6.03 | 10 |
| 11 | 15.76 | 5.62 | 41 |
| 12 | 16.52 | 5.36 | 73 |
| 13 | 17.31 | 5.12 | 48 |
| 14 | 17.65 | 5.02 | 39 |
| 15 | 18.15 | 4.88 | 50 |
| 16 | 18.77 | 4.72 | 27 |
| 17 | 19.04 | 4.66 | 13 |
| 18 | 20.01 | 4.43 | 21 |
| 19 | 20.35 | 4.36 | 53 |
| 20 | 20.6 | 4.31 | 44 |
| 21 | 21 | 4.23 | 40 |
| 22 | 21.45 | 4.14 | 21 |
| 23 | 22 | 4.04 | 14 |
| 24 | 23.01 | 3.86 | 42 |
| 25 | 23.2 | 3.83 | 31 |
| 26 | 24.31 | 3.66 | 13 |
| 27 | 24.71 | 3.6 | 15 |
| 28 | 25.12 | 3.54 | 11 |
| 29 | 25.39 | 3.51 | 10 |
| 30 | 25.85 | 3.44 | 18 |
| 31 | 26.37 | 3.38 | 17 |
| 32 | 26.71 | 3.34 | 4 |
| 33 | 27.3 | 3.26 | 5 |
| 34 | 27.75 | 3.21 | 18 |
| 35 | 28.22 | 3.16 | 3 |
| 36 | 28.84 | 3.09 | 6 |
| 37 | 30 | 2.98 | 6 |
| 38 | 31.07 | 2.88 | 7 |

According to another very preferred embodiment of the present invention there is provided the vortioxetine monooxalate (1:1) salt of the Formula X which has a HPLC purity higher than 99.5%, preferably higher than 99.8% and contains less than 0.5%, preferably less than 0.2% of the impurity of the Formula VIII.

According to the present intervention there is provided a polymorph of the vortioxetine monooxalate (1:1) salt having the following characteristic X-ray powder diffraction peaks: 2θ (±0.2° 2θ): 14.48; 17.8; 18.97; 20.38; 23.87; 27.57. The polymorph can also be characterized by the salt which has the following characteristic X-ray powder diffraction peaks: 2θ (±0.2° 2θ): 13.67; 14.48; 16.01; 17.8; 18.15; 18.46; 18.97; 20.38; 23.87; 27.57; 28.15. The monooxalate (1:1) salt can also be characterized by characteristic X-ray powder diffraction peaks summarized in the following Table (relative intensities>2%)

| Peak | 2θ (°) | d (Å) | Relative intensity (%) |
|---|---|---|---|
| 1 | 10.16 | 8.7 | 9 |
| 2 | 13.67 | 6.47 | 41 |
| 3 | 14.48 | 6.11 | 96 |
| 4 | 15.38 | 5.76 | 3 |
| 5 | 16.01 | 5.53 | 28 |
| 6 | 16.98 | 5.22 | 8 |
| 7 | 17.8 | 4.98 | 51 |
| 8 | 18.15 | 4.88 | 32 |
| 9 | 18.46 | 4.8 | 18 |
| 10 | 18.97 | 4.67 | 100 |
| 11 | 19.54 | 4.54 | 7 |
| 12 | 20.38 | 4.36 | 48 |
| 13 | 21.1 | 4.21 | 10 |
| 14 | 21.72 | 4.09 | 3 |
| 15 | 22.16 | 4.01 | 4 |
| 16 | 22.75 | 3.91 | 3 |
| 17 | 23.16 | 3.84 | 10 |
| 19 | 24.36 | 3.65 | 5 |
| 20 | 24.89 | 3.57 | 2 |
| 21 | 25.35 | 3.51 | 3 |
| 22 | 26.1 | 3.41 | 6 |
| 23 | 26.81 | 3.32 | 16 |
| 24 | 27.15 | 3.28 | 4 |
| 25 | 27.57 | 3.23 | 57 |
| 26 | 28.15 | 3.17 | 29 |
| 27 | 29.32 | 3.04 | 10 |
| 28 | 29.73 | 3 | 3 |
| 29 | 30.65 | 2.91 | 2 |
| 30 | 31.63 | 2.83 | 8 |
| 31 | 31.96 | 2.8 | 3 |
| 32 | 32.33 | 2.77 | 12 |
| 33 | 32.74 | 2.73 | 3 |
| 34 | 33.37 | 2.68 | 4 |
| 35 | 34.44 | 2.6 | 10 |

The advantage of the present invention is that the salts according to the invention, namely the vortioxetine salicylate, vortioxetine hemicitrate, vortioxetine monocitrate monohydrate, vortioxetine monocitrate anhydrate, vortioxetine malonate, vortioxetine hemioxalate, vortioxetine monooxalate, vortioxetine L-malate, vortioxetine besylate, vortioxetine acetate, vortioxetine succinate and vortioxetine L-(+)-mandelate is the uniform morphology. Accordingly these salts have reproducible dissolution speed, bioavailability, chemical stability and processing properties' (e.g. filtration, drying, tableting properties etc).

The vortioxetine salicylate, vortioxetine hemicitrate, vortioxetine monocitrate monohydrate, vortioxetine monocitrate anhydrate, vortioxetine malonate, vortioxetine hemioxalate, vortioxetine monooxalate, vortioxetine L-malate, vortioxetine besylate, vortioxetine acetate, vortioxetine succinate and vortioxetine L-(+)-mandelate salts of the present invention are pharmaceutical active ingredients which can be manufactured on industrial scale by a readily reproducible process.

The above salts can be prepared according to the process of the present invention from easily available and inexpensive starting materials by a simple synthesis. Said salts can be used as high purity pharmaceutical active ingredients. It has been surprisingly found that the impurities formed during the synthesis can be separated by conversion into the mandelic acid salt. The use of said salt formed with mandelic acid enables the preparation of further salts having high purity. The salts thus obtained are chemically and morphologically stable both as active ingredient and in pharmaceutical compositions. An additional advantage of the salt formed with mandelic acid is that it is obtained in a highly pure form.

The pure mandelic acid salt is obtained substantially in a one-pot process in pure form without isolating the base.

The analytical tests of the compositions and products of the present invention are carried out by the following methods:

HPLC:
The purity is determined by the following HPLC method:
Apparatus: HP1100
Column: Purospher STAR RP-8, 5 µm, 250×4
Eluents: A=acetonitrile (referred to furtheron as ACN) 100/water 90/0.05% HCOOH
B=ACN90/water 10/0.05% HCOOH
Gradient: min/B % 0/10, 10/100, 12/100, 12.1/10, 15/100
Streaming speed: 1 ml/min
Temperature: 25° C.
The sample is dissolved in ACN-water 1:1 0.3 mg/ml
Injection: 2 ul
Detection: 210 nm X-Ray Powder Diffraction The X-ray powder diffraction data of all tested substances are obtained by using the following measuring conditions:
Apparatus: Bruker D8 Advance X-ray powder diffractometer
Radiation: CuK$\alpha_1$ ($\lambda$=1,54060 Å), CuK$\alpha_2$ ($\lambda$=1,54439 Å)
Acceleration voltage: 40 kV
Anode heating current: 40 maA
Equipment: Gobel mirror/optical device preparing a parallel bundle optic), 9 position sample change, transmission apparatus
Detector: Brujer LynxEye line detector
Soller: 2.5°
Orifice: 0.6 mm divergence orifice
Detected side: 8 mm entering orifice
Measuring interval: continuous 0/0 scan. 4-35°2Θ
Time of one step: 1.2 s
Interval between steps: 0.02°2Q
Preparation of the samples: the unpowdered sample is placed between Mylar foils at room temperature
Rotation speed of the sample: 0.5 rotation per sec.
Number of measuring cycles: 1
Time of measurement: 35 minutes Thermo Gravimetrical Measurement TG measurement conditions:
Apparatus: Perkin Elmer Pyris 1 TGA thermogravimetrical analyser
Atmosphere. streaming $N_2$ (20 ml/min.)
Temperature program: 25° C.-130° C.-10° C./minute
Crucible: Pt NMR Measurements The NMR spectra are obtained on a Varian Inova 500 MHz and Bruker AvanceIII 400 MHz NMR apparatus, by using a TMS internal standard IR Measurements The IR spectra are obtained on Bruker Vector 22 FTIR and Bruker Alpha FTIR apparatus, in KBr pastil.

Measurement of the Melting Point

The melting points are determined on a heatable Leica Galen microscopic melting point measuring apparatus.

Determination of the Dissolution of the Active Ingredient from the Tablet

The dissolution of the immediate release tablets is measured on a FaSSGF (fasted state stimulated gastric fluid) apparatus, in a pH=1.6 solution prepared as follows:
2.0 g of sodium chloride are weighed in a 1.00 l flask, dissolved in 900 ml of degassed 37° C. purified water. The pH is adjusted to 1.6 with a 1:1 mixture of hydrochloric acid and purified water, the solution is filled up to the sign and homogenized. In 500 ml of the solution thus obtained 59.6 mg of a SIF powder (4:1 mixture of sodium taurocholate and lecithin) are dissolved, where after 500 ml of the residue are added. In the solution thus obtained 100 mg of pepsin are dissolved and the mixture is again homogenized. The mixture can be stored at room temperature for 48 hours and at 37° C. for 24 hours.

The dissolved active ingredient is determined by a HPLC method.
Apparatus: ACQUITY UPLC H-Class
Type of column: Waters Acquity UPLC BEH C18 2.1×50 mm 1.7 µm
Composition of the eluent: Eluent A ACN:$H_2O$:$H_3PO_4$=400:600:0.5 ml/ml/ml
Streaming speed: 0.6 ml/min.
Column temperature: 30° C.
Temperature of the sample area: 37° C.
Injection: 2 µl
Stop time: 2 minutes Conditions of Dissolution Agilent 708DS
Chinese Pharmacopeia Dissolution Test Method 3
Dissolving medium: 250 ml FaSSGF pH=1.6 solution
Speed of stirring paddle: 75 rpm
Temperature: 37° C.

The distribution of the particle size is measured on a Malvern Mastersizer 3000 apparatus under the following conditions:

| Instrument: | Malvern Mastersizer 3000 |
|---|---|
| Accessory: | Aero S |
| Accessory control: | Air pressure: [ 2,0 ] barg |
| Configuration: | Venturi type: [x] Standard Venturi disperser |
| Calculation mode: | Mie evaluation |
| Refractive index: | 1.520 |
| Absorption coefficient: | 0.1 |
| Data processing: | Model: [x] General purpose |

Figure 1:
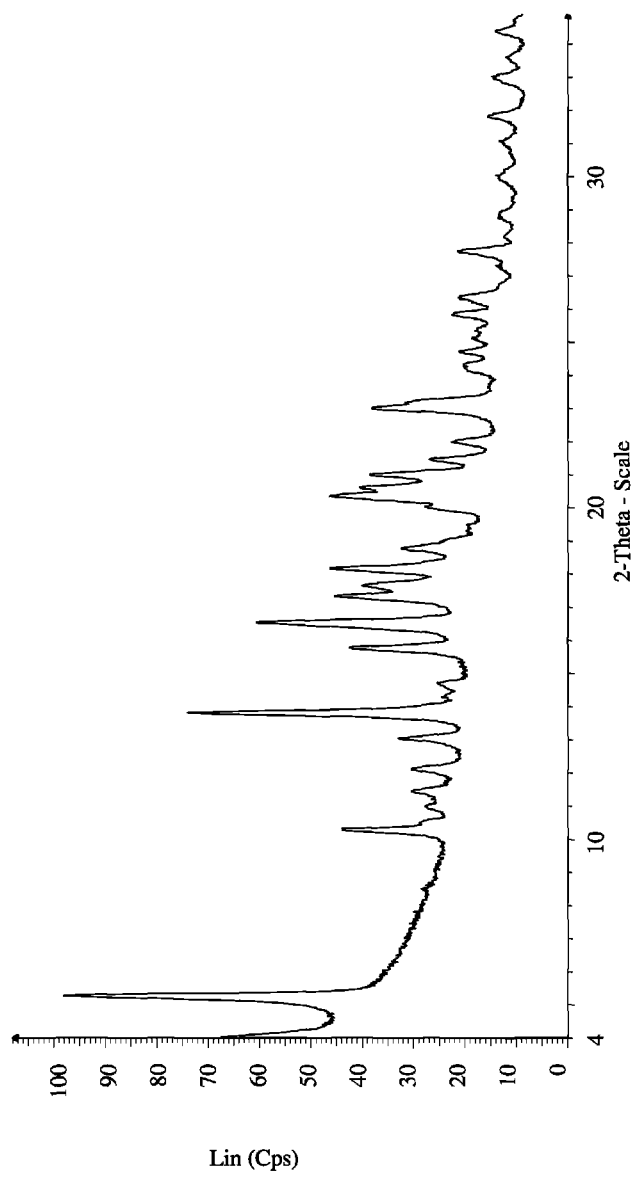
FIG. 1./Drawing 1: X-ray powder diffractogram of the vortioxetine hemicitrate (2:1) salt of the Formula XI.

Further details of the present invention are to be found in the following examples without limiting the scope of protection to said examples.

Example 1

Preparation of 2,4-dimethyl-1-/(2-nitrophenyl)-phenylsulfanyl/-benzene (compound of the Formula IV)

31.5 g (0.2 mole) of 2-chloro-nitrobenzene (II) (wherein Z stands for chlorine) and 27.65 g (0.2 mole) of 2,4-dimethylthiophenol (III) are dissolved in 500 ml of dimethyl formamide whereupon to the solution 30.35 g (0.22 mole) of potassium carbonate are added under vigorous stirring. The reaction mixture is stirred at an internal temperature of 100° C. in an inert atmosphere for 2.5 hours. The reaction mixture is evaporated. The viscous resin thus obtained is treated with 250 ml of water. The yellow crystalline substance thus obtained is filtered, washed with 250 ml of water. The yellow crystalline product thus obtained is filtered, washed three times with 50 ml of water each and dried. Thus 51.76 g (99.79%) of a yellow crystalline product are obtained, which melts at 82-89° C. (HPLC purity 99.89%). The product can be used in the next step without purification.

Elementary analysis $C_{14}H_{13}NO_2S$ (259.33) calculated for the Formula:

| Calc [%] | C: 64.48 | H: 5.05 | N: 5.40 | S: 12.36 |
| --- | --- | --- | --- | --- |
| Found [%] | C: 64.71 | H: 5.06 | N: 5.35 | S: 12.44 |

IR (KBr): 1517, 1331, 1302, 810, 732 cm$^{-1}$.
$^1$H-NMR (CDCl$_3$, 400 MHz): δ 8.25 (m, 1H), 7.47 (d, J=7.8 Hz, 1H), 7.31 (m, 1H), 7.21 (s, 1H), 7.19 (m, 1H), 7.11 (d, J=7.6 Hz, 1H), 6.70 (m, 1H), 2.40 (s, 3H), 2.30 (s, 3H) ppm.

Example 2

Preparation of 2-[(2,4-dimethyl-phenyl)-sulfanyl]-aniline (V)

A solution of 51.9 g (0.2 mole) of 2,4-dimethyl-1-[(2-nitro-phenyl)-sulfanyl]-benzene (IV) and 200 ml ethanol is placed in a hydrogenating autoclave whereupon 5.2 g of a 10% palladium/charcoal catalyst are added. The closed autoclave is rinsed, placed under a hydrogen pressure of 10 bar and stirred in a 80° C. oil bath for 6 hours (if the internal pressure decreases to 0 bar, the autoclave is put again under a hydrogen pressure of 10 bar). The heating is stopped and the autoclave is allowed to stand at room temperature overnight. The catalyst is filtered, washed with ethanol and the filtrate is evaporated. Thus 45.87 g (theoretical yield 45.85 g) of a yellow-brown oily product are obtained (HPLC purity 96%). The product is used in the next step without purification.

Elementary analysis $C_{14}H_{15}NS$ (229.35) calculated for the Formula:

| Calc [%] | C: 73.32 | H: 6.59 | N: 6.11 |
| --- | --- | --- | --- |
| Found [%] | C: 73.02 | H: 6.56 | N: 6.14 |

IR (film): 3473, 3374, 1609, 1479, 751 cm$^{-1}$.
$^1$H-NMR (CDCl$_3$, 500 MHz): δ 7.34 (m, 1H), 7.19 (m, 1H), 6.98 (s, 1H), 6.83 (d, J=8.1 Hz, 1H), 6.74 (m, 1H), 6.72 (m, 1H), 6.70 (d, J=7.9 Hz, 1H), 4.19 (b, 2H), 2.37 (s, 3H), 2.25 (s, 3H) ppm.

Example 3

Preparation of the 1-[2-(2,4-dimethyl-phenylsulfanyl)-phenyl]-piperazine L-(+)-mandelic acid salt of the Formula IX 1.0 g (4.36 millimoles) of 2-[(2,4-dimethyl-phenyl)-sulfanyl]-aniline, 0.91 g (5.0 millimoles) of bis-(2-chloroethyl-amine)-hydrochloride and 0.72 g (5.2 millimoles) of potassium carbonate are suspended in a mixture of 10 ml of toluene and 10 ml of DMI. The suspension is placed in a hermetically closed Teflon vessel and heated in an oil bath at 170-180° C. for 12 hours under stirring. The reaction mixture is cooled every 3 hours, whereupon bis-(2-chloro-ethyl)-amine hydrochloride and potassium carbonate are added in an amount disclosed above. Heating is continued. The reaction having been completed the suspension is filtered, the inorganic salt mixture is washed successively with 5 ml of toluene and three times with 5 ml of dichloro methane each. The united filtrates are poured in a mixture of 100 g of ice and 5 ml of ammonium hydroxide, then evaporated dichloro methane and toluene free. The precipitated resin is solidified by rubbing. The solid substance is filtered, washed with water until neutral and dried. Thus about 0.94 g (72%) of sticky crystals are obtained from which a 0.3 g (about 1.0 millimole) portion is suspended in 6 ml of acetone. The suspension is warmed to 60° C. whereupon at this temperature a solution of 0.15 g (1.0 millimole) of L-(+)-mandelic acid and 2 ml of acetone is added dropwise. After some minutes the precipitation of crystals begins. The precipitated salt is filtered, washed three times whit 2 ml of cold acetone each and dried. Thus 0.35 g (78%) of the desired compound is obtained. Mp.: 155-158° C., HPLC purity 99.9%.

IR (KBr): 2736, 2517, 1716, 1594, 1471, 1370, 1232, 1187 cm$^{-1}$.

$^1$H-NMR (CDCl$_3$, 400 MHz): δ 7.50 (m, 2H), 7.36 (d, J=7.8 Hz, 1H), 7.32 (m, 2H), 7.21 (m, 1H), 7.19 (s, 1H), 7.09 (m, 1H), 7.05 (m, 1H), 6.92 (m, 1H), 6.91 (m, 1H), 6.52 (m, 1H), 4.95 (s, 1H), 3.06 (m, 2H), 3.02 (m, 4H), 2.95 (m, 2H), 2.38 (s, 3H), 2.31 (s, 3H) ppm.

The characteristic X-ray powder diffraction peaks of the salt thus obtained are shown on FIG. 3 and summarized in the following Table:

(relative intensities>2%)

| Peak | 2θ (°) | d (Å) | Relative intensity (%) |
|---|---|---|---|
| 1 | 4.25 | 20.76 | 16 |
| 2 | 11.69 | 7.56 | 22 |
| 3 | 11.86 | 7.46 | 24 |
| 4 | 12.25 | 7.22 | 10 |
| 5 | 13.29 | 6.66 | 32 |
| 6 | 14.42 | 6.14 | 16 |
| 7 | 16.52 | 5.36 | 65 |
| 8 | 16.93 | 5.23 | 100 |
| 9 | 17.17 | 5.16 | 26 |
| 10 | 17.58 | 5.04 | 11 |
| 11 | 18.47 | 4.80 | 17 |
| 12 | 18.81 | 4.71 | 2 |
| 13 | 19.54 | 4.54 | 7 |
| 14 | 20.55 | 4.32 | 2 |
| 15 | 20.78 | 4.27 | 5 |
| 16 | 22.18 | 4.00 | 2 |
| 17 | 22.39 | 3.97 | 2 |
| 18 | 23.15 | 3.84 | 9 |
| 19 | 23.46 | 3.79 | 38 |
| 20 | 23.94 | 3.71 | 15 |
| 21 | 24.29 | 3.66 | 18 |
| 22 | 24.59 | 3.62 | 5 |
| 23 | 24.95 | 3.57 | 4 |
| 24 | 25.42 | 3.50 | 8 |
| 25 | 26.21 | 3.40 | 24 |
| 26 | 26.93 | 3.31 | 13 |
| 27 | 28.28 | 3.15 | 5 |
| 28 | 28.71 | 3.11 | 3 |
| 29 | 29.00 | 3.08 | 3 |
| 30 | 30.18 | 2.96 | 3 |
| 31 | 31.32 | 2.85 | 4 |
| 32 | 31.82 | 2.81 | 2 |
| 33 | 32.58 | 2.75 | 3 |
| 34 | 33.10 | 2.70 | 2 |
| 35 | 33.36 | 2.68 | 2 |

Example 3/A

Preparation of the 1-[2-(2,4-dimethyl-phenylsulfanyl)-phenyl]-piperazin L-(+)-mandelic acid salt of the Formula (IX)

3.4 g (14.8 millimoles) of 2-[(2,4-dimethyl-phenyl)-sulfanyl]-aniline and 2.9 g (16.25 millimoles) of bis-(2-chloroethyl)-amine hydrochlorideare suspended in a mixture of 3.4 ml of toluene and 3.4 ml of DMI. The suspension is heated to boiling in an inert atmosphere for 4 hours under stirring. The reaction mixture is cooled and washed until free from toluene, whereupon one proceeds as described in Example 3.

Example 3/B

Preparation of 1-/2-(2,4-dimethyl-phenylsulfanyl)-phenyl/-piperazine L-(+)-mandelic acid salt (IX)

3.4 g (14.8 millimoles) of 2-[(2,4-dimethyl-phenyl)-sulfanyl]-aniline and 2.9 g (16.25 millimoles) of bis-(2-chloroethyl)-amine)-hydrochloride are dissolved in a mixture of 3.4 ml of toluene and 3.4 ml of DMI. The solution is heated to boiling in an oil bath at 170-180° C. for 6 hours under stirring. To the warm reaction mixture 34 ml of toluene are added. The mixture is allowed to cool to room temperature and 20 ml of a 1 n sodium hydroxide solution are added. The mixture is stirred until clear phases are formed. The phases are separated, the organic layer is washed four times with 10 ml of water each, warmed to 60° C. and 2.25 g (14.8 millimoles) of L-(+)-mandelic acid are added and the reaction mixture is stirred at this temperature until the L-(+)-mandelic acid is dissolved. On cooling the precipitation of crystals begins. The crystal suspension is placed in a refrigerator overnight, the precipitated salt is filtered, washed twice with 3 ml of cold toluene each and three times with 5 ml of acetone each and dried. Thus 4.3 g (64.4%) of the desired L-(+)-mandelic acid salt are obtained. Mp.: 154-157° C. HPLC yield 99.91%.

Example 3/C

1-[2-(2,4-dimethyl-phenylsulfanyl)-phenyl]-piperazine L-(+)-mandelic acid salt (IX) (from vortioxetine base by salt formation)

6.0 g (20.0 millimoles) of 1-[2-(2,4-dimethyl-phenylsulfanyl)-phenyl]-piperazine base are suspended in 120 ml of acetone. The suspension is warmed to reflux temperature. A solution is obtained. To the hot solution 3.0 g (20.0 millimoles) of L-(+)-mandelic acid in 40 ml of acetone are added. The precipitation of crystals immediately begins. The suspension is stirred at room temperature for 6 hours and allowed to stand at 4° C. overnight. The crystals are filtered, washed with cold acetone and dried under an infrared lamp until constant weight. Yield 8.31 g (92.2%). The HPLC purity of the white crystals is >99.9% (HPLC).

Figure 3:
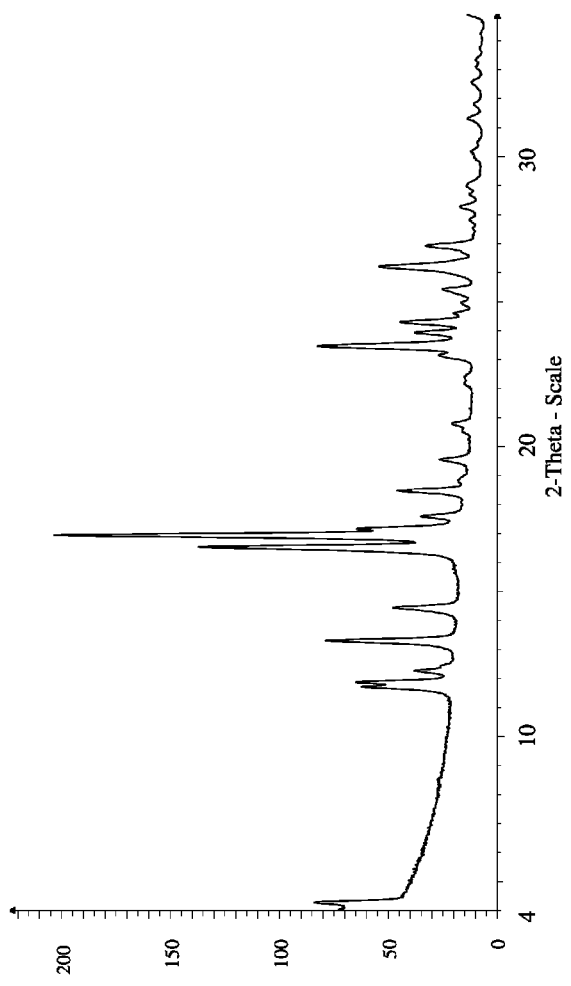
FIG. 3./Drawing 3: X-ray powder diffractogram of the 1-[2-(2,4-dimethyl-phenylsulfanyl)-phenyl]-piperazine L-(+)-amygdalic acid salt of the Formula IX.
Figure 4:
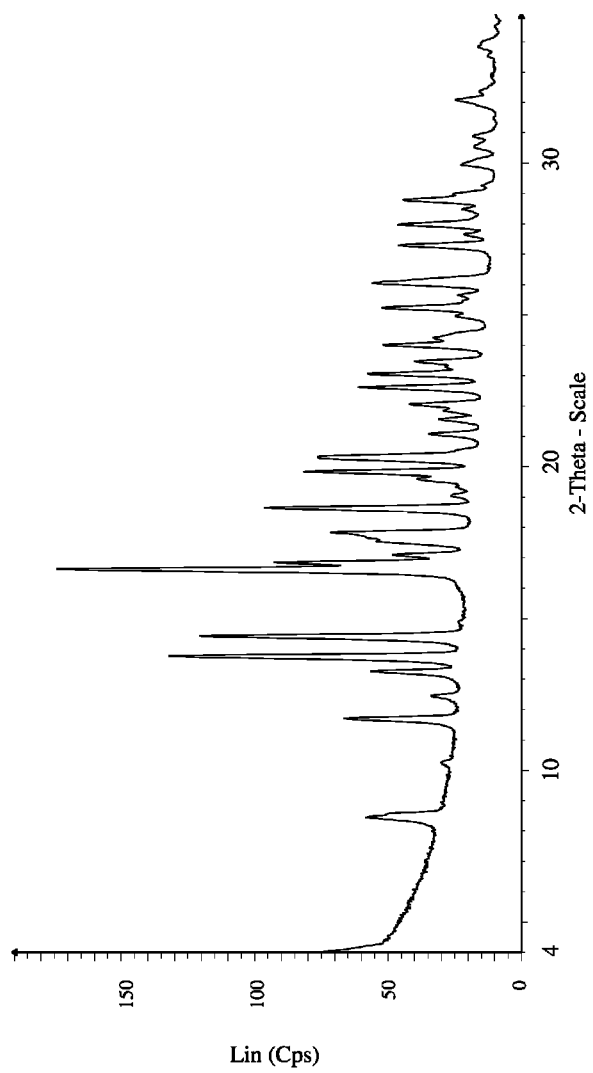
FIG. 4./Drawing 4: X-ray powder diffractogram of the 1-[2-(2,4-dimethyl-phenylsulfanyl)-phenyl]-piperazine salicylic acid salt of the Formula XIII FIG. 5./Drawing 5: X-ray powder diffractogram of the vortioxetine monocitrate (1:1) hydrate salt of the Formula XIV.
Figure 5:
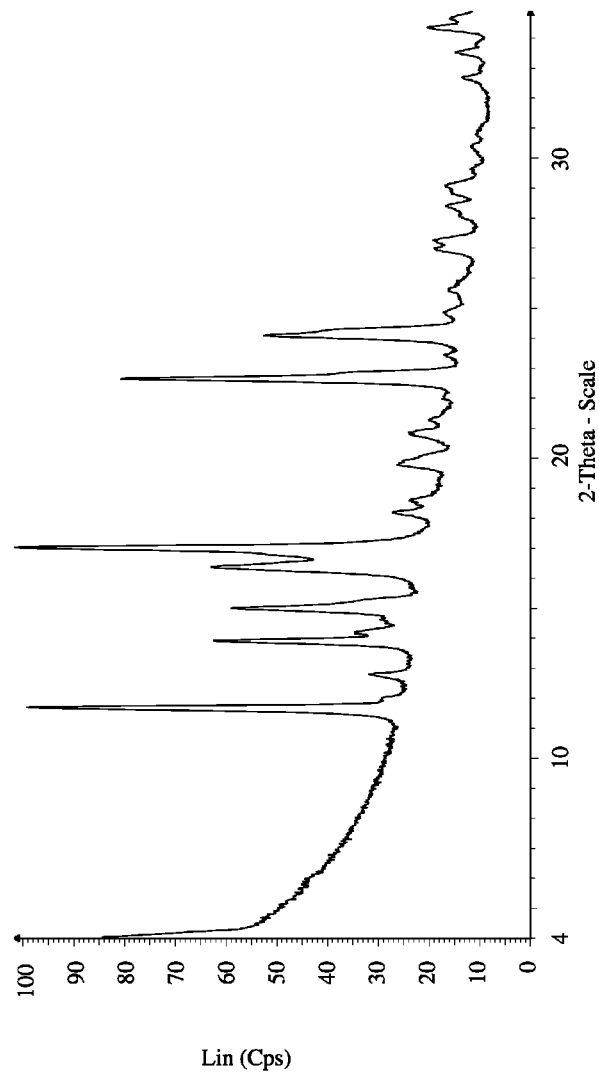
Figure 6:
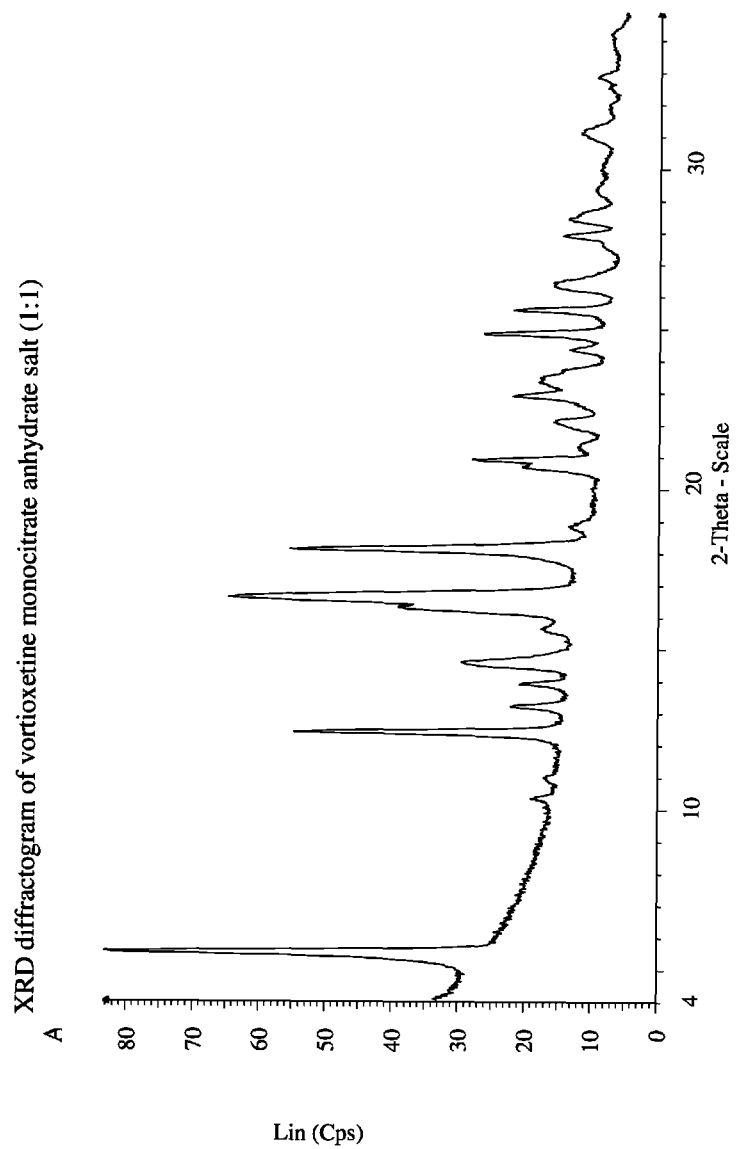
FIG. 6./Drawing 6: X-ray powder diffractogram of the vortioxetine monocitrate (1:1) anhydrate salt of the Formula XX.
Figure 7:
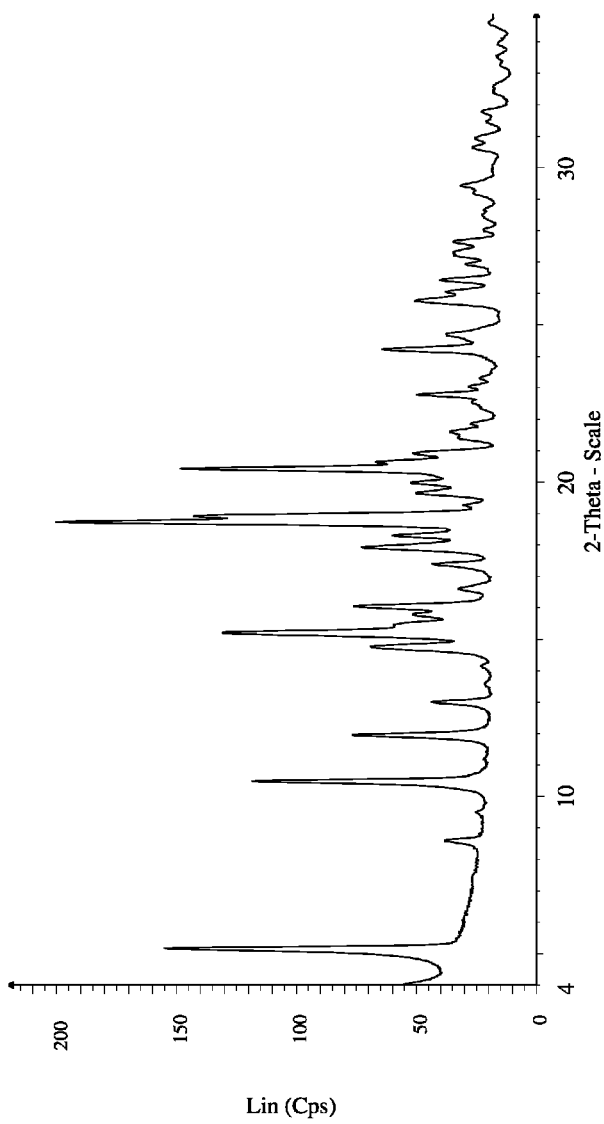
FIG. 7./Drawing 7: X-ray powder diffractogram of the vortioxetine malonate salt of the Formula XV.
Figure 8:
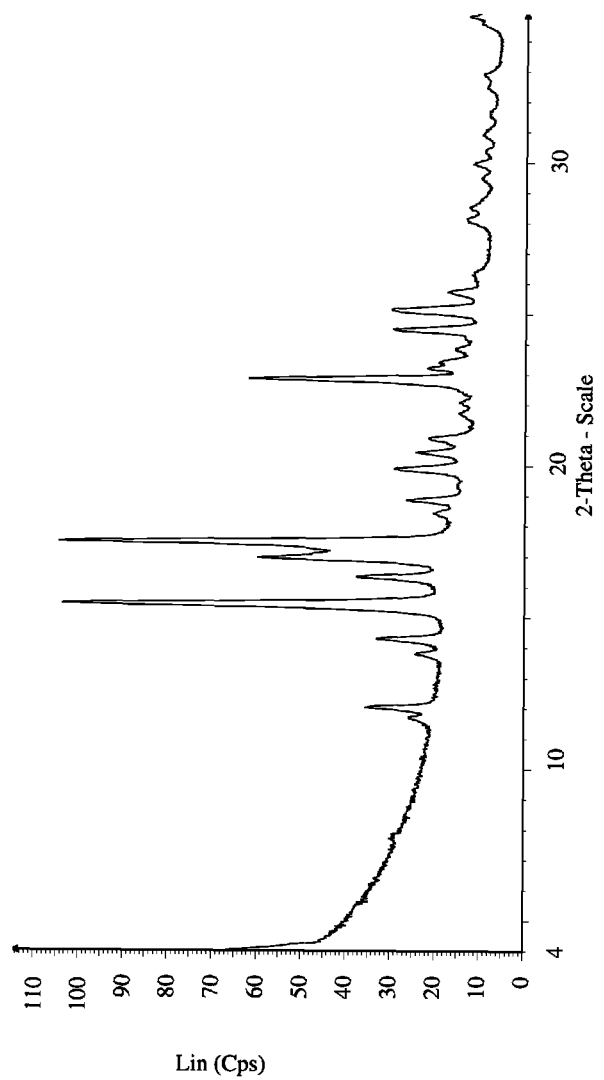
FIG. 8./Drawing 8: X-ray powder diffractogram of the vortioxetine hemioxalate salt of the Formula XVI.
Figure 9:
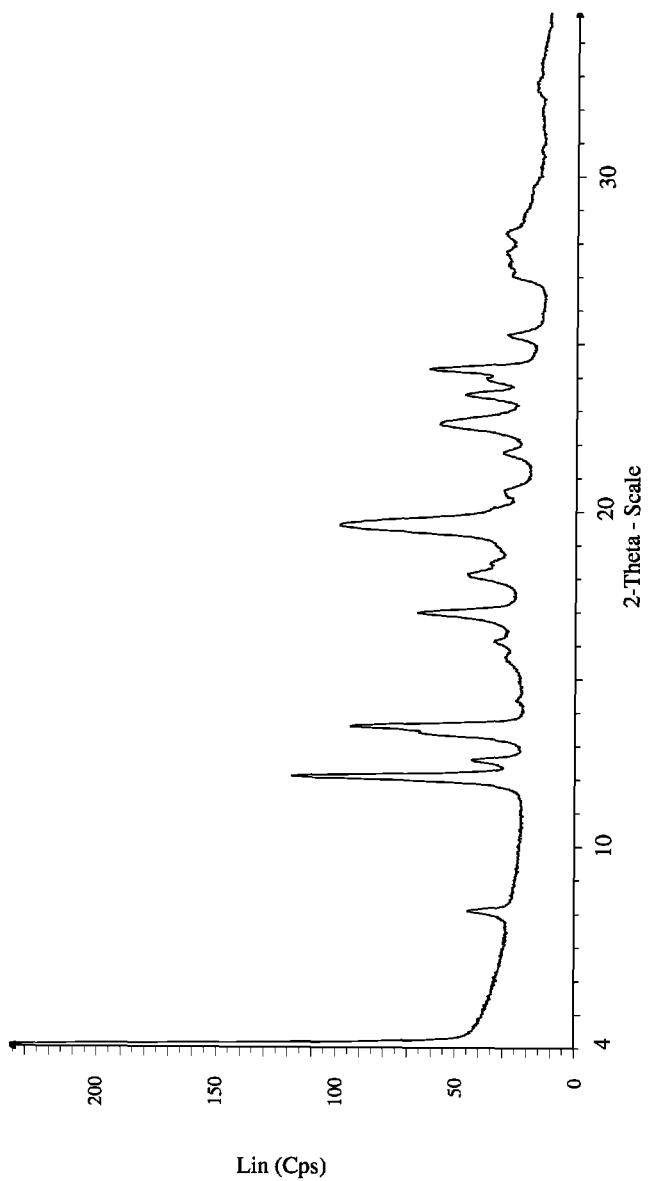
FIG. 9./Drawing 9: X-ray powder diffractogram of the vortioxetine malic acid salt of the Formula XVII.

The characteristic X-ray powder diffraction peaks of the salt are shown on FIG. 3.

Example 4

Preparation of 1-[2-(2,4-dimethyl-phenylsulfanyl)-phenyl]-piperazine from the L-(+)-mandelic acid salt of the Formula IX 5.26 g (11.67 millimoles) of 1-[2-(2,4-dimethyl-phenylsulfanyl)-phenyl]-piperazine L-(+)-mandelic acid salt prepared according to any of examples 3, 3/A or 3/B are suspended in 175 ml of dichloro methane, whereupon 175 ml of a 1 M sodium hydroxide solution are added. The mixture is cooled until clear pure phases are formed. The layers are separated; the organic phase is washed three times with 100 ml of water each, dried over sodium sulphate and evaporated in vacuo. The crystalline residue is suspended in 50 ml of water, washed three times with 20 ml of water each and dried. Thus 3.5 g (yield about 100%) of the desired product are obtained. Mp.: 112-115° C.

Example 5

Preparation of 1-[2-(2,4-dimethyl-phenylsulfanyl)-phenyl]-piperazine monooxalate salt (X)

One proceeds as described in Example 3 except that to the suspension a solution of 0.09 g (1.0 millimoles) of oxalic acid in 2 ml of acetone is added at 60° C. Thus 0.33 g (85%) of the desired monooxalate salt is obtained. Mp.: 185-188° C., HPLC purity 97.85%.

IR (KBr): 3434, 3016, 2510, 1715, 1652, 1474, 1209, 705 cm$^{-1}$.

$^1$H-NMR (DMSO-d$_6$, 400 MHz): δ 7.33 (d, J=7.8 Hz, 1H), 7.25 (s, 1H), 7.14 (m, 2H), 7.10 (m, 1H), 6.95 (m, 1H), 6.41 (m, 1H), 3.17 (m, 4H), 3.13 (m, 4H), 2.33 (s, 3H), 2.24 (s, 3H) ppm.

$^{13}$CNMR (DMSO-d$_6$, 100 MHz): δ 163.39, 148.06, 141.79, 139.44, 135.86, 133.56, 131.92, 128.22, 127.05, 126.18, 126.00, 125.25, 120.46, 48.42, 43.56, 20.87, 20.23 ppm.

Figure 2:
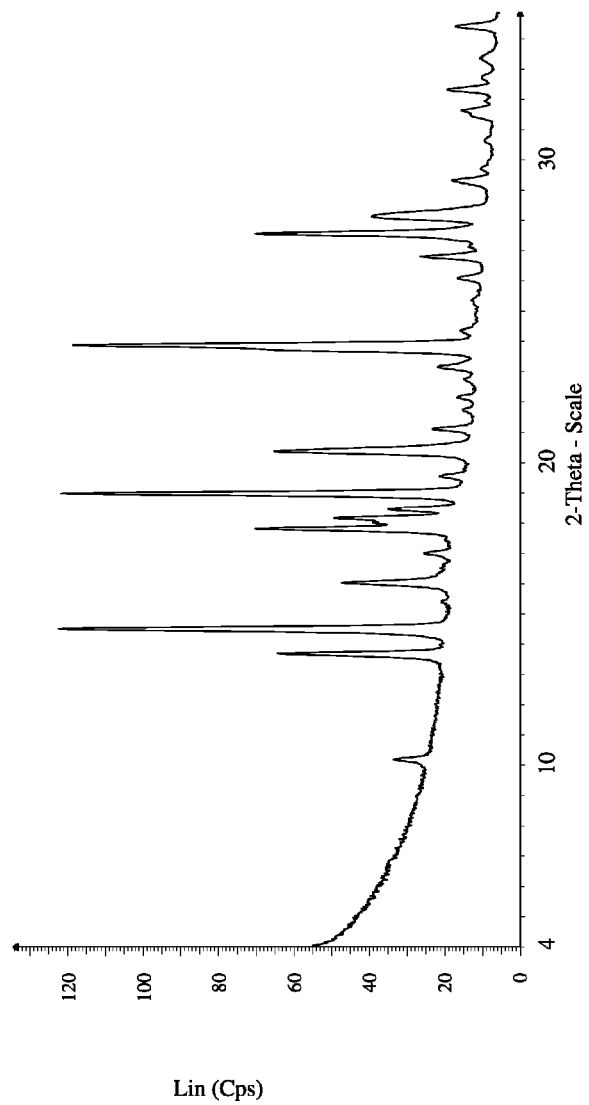
FIG. 2./Drawing 2: X-ray powder diffractogram of the vortioxetine monooxaalate (1:1) salt of the Formula X.

The characteristic X-ray powder diffraction peaks of the salt are shown on FIG. 2.

(relative intensities> than 2%)

| Peak | 2θ (°) | d (Å) | Relative intensity (%) |
|---|---|---|---|
| 1 | 10.16 | 8.70 | 9 |
| 2 | 13.67 | 6.47 | 41 |
| 3 | 14.48 | 6.11 | 96 |
| 4 | 15.38 | 5.76 | 3 |
| 5 | 16.01 | 5.53 | 28 |
| 6 | 16.98 | 5.22 | 8 |
| 7 | 17.80 | 4.98 | 51 |
| 8 | 18.15 | 4.88 | 32 |
| 9 | 18.46 | 4.80 | 18 |
| 10 | 18.97 | 4.67 | 100 |
| 11 | 19.54 | 4.54 | 7 |
| 12 | 20.38 | 4.36 | 48 |
| 13 | 21.10 | 4.21 | 10 |
| 14 | 21.72 | 4.09 | 3 |
| 15 | 22.16 | 4.01 | 4 |
| 16 | 22.75 | 3.91 | 3 |
| 17 | 23.16 | 3.84 | 10 |
| 18 | 23.87 | 3.72 | 100 |
| 19 | 24.36 | 3.65 | 5 |
| 20 | 24.89 | 3.57 | 2 |
| 21 | 25.35 | 3.51 | 3 |
| 22 | 26.10 | 3.41 | 6 |
| 23 | 26.81 | 3.32 | 16 |
| 24 | 27.15 | 3.28 | 4 |
| 25 | 27.57 | 3.23 | 57 |
| 26 | 28.15 | 3.17 | 29 |
| 27 | 29.32 | 3.04 | 10 |
| 28 | 29.73 | 3.00 | 3 |
| 29 | 30.65 | 2.91 | 2 |
| 30 | 31.63 | 2.83 | 8 |
| 31 | 31.96 | 2.80 | 3 |
| 32 | 32.33 | 2.77 | 12 |
| 33 | 32.74 | 2.73 | 3 |
| 34 | 33.37 | 2.68 | 4 |
| 35 | 34.44 | 2.60 | 10 |

Example 6

Preparation of the 1-[2-(2,4-dimethyl-phenylsulfanyl)-phenyl]-piperazine hemicitrate salt (XI)

One proceeds as described in Example 3 except that to the suspension 0.115 g (0.6 millimole) of citric acid dissolved in 2 ml of acetone is added at 60° C. Thus 0.32 g (79%) of the desired hemicitrate salt is obtained. Mp.: 183-186° C., HPLC purity 98.93%.

IR (KBr): 2491, 1603, 1474, 1280, 764 cm$^{-1}$.

$^1$H-NMR (CD$_3$OD-CDCl$_3$, 500 MHz): δ 7.31 (d, J=7.8 Hz, 1H), 7.18 (d, J=0.6 Hz, 1H), 7.13 (m, 1H), 7.11 (m, 1H), 7.05 (m, 1H), 6.92 (m, 1H), 6.54 (dd, J1=0.9 Hz, J2=7.7 Hz, 1H), 3.30 (m, 4H), 3.24 (m, 4H), 2.81 (d, J=15.4 Hz, 0.5*2H), 2.73 (d, J=15.4 Hz, 0.5*2H), 2.36 (s, 3H), 2.29 (s, 3H) ppm.

The X-ray powder diffraction data are shown on FIG. 1. The X-ray powder mixture diffraction of the citric acid (1:2) salt are shown in the following Table 2:

TABLE 2

| Peak | 2θ (°) | d (Å) | Relative intensity (%) |
|---|---|---|---|
| 1 | 5.24 | 16.85 | 100 |
| 2 | 10.26 | 8.61 | 36 |
| 3 | 10.50 | 8.41 | 10 |
| 4 | 10.94 | 8.08 | 9 |
| 5 | 11.43 | 7.74 | 14 |
| 6 | 12.10 | 7.31 | 16 |
| 7 | 13.02 | 6.80 | 21 |
| 8 | 13.79 | 6.41 | 93 |
| 9 | 14.28 | 6.20 | 8 |
| 10 | 14.67 | 6.03 | 10 |
| 11 | 15.76 | 5.62 | 41 |
| 12 | 16.52 | 5.36 | 73 |
| 13 | 17.31 | 5.12 | 48 |
| 14 | 17.65 | 5.02 | 39 |
| 15 | 18.15 | 4.88 | 50 |
| 16 | 18.77 | 4.72 | 27 |
| 17 | 19.04 | 4.66 | 13 |
| 18 | 20.01 | 4.43 | 21 |
| 19 | 20.35 | 4.36 | 53 |
| 20 | 20.60 | 4.31 | 44 |
| 21 | 21.00 | 4.23 | 40 |
| 22 | 21.45 | 4.14 | 21 |
| 23 | 22.00 | 4.04 | 14 |
| 24 | 23.01 | 3.86 | 42 |
| 25 | 23.20 | 3.83 | 31 |
| 26 | 24.31 | 3.66 | 13 |
| 27 | 24.71 | 3.60 | 15 |
| 28 | 25.12 | 3.54 | 11 |
| 29 | 25.39 | 3.51 | 10 |
| 30 | 25.85 | 3.44 | 18 |
| 31 | 26.37 | 3.38 | 17 |
| 32 | 26.71 | 3.34 | 4 |
| 33 | 27.30 | 3.26 | 5 |
| 34 | 27.75 | 3.21 | 18 |
| 35 | 28.22 | 3.16 | 3 |
| 36 | 28.84 | 3.09 | 6 |
| 37 | 30.00 | 2.98 | 6 |
| 38 | 31.07 | 2.88 | 7 |

The X-ray powder diffraction data of the vortioxetine citric acid (1:2) salt (relative intensities>2%)

Example 7

1-/2-[(2,4-dimethyl-phenylsulfanyl)-phenyl]-piperazine hydrobromide salt (beta polymorph One proceeds as described in Example 3 except that to the suspension 0.113 ml (1.0 millimole) of an aqueous 48% hydrogen bromide solution is added at 60° C. Thus 0.26 g (69%) of the desired hydrobromide salt (β polymorph) is obtained. Mp.: 224-229° C., HPLC purity 97.72%.

elementary analysis C$_{18}$H$_{23}$BrN$_2$S (379.37) calculated for the Formula:

| | | | | | |
|---|---|---|---|---|---|
| Calc [%] | C: 56.99 | H: 6.11 | N: 7.38 | S: 8.45 | Br: 21.06 |
| Found [%] | C: 56.31 | H: 5.98 | N: 7.30 | S: 8.22 | Br: 21.08 |

IR (KBr): 2704, 2460, 1440, 1041, 927 cm$^{-1}$.

$^1$H-NMR (DMSO-d$_6$, 400 MHz): δ 8.77 (b, 2H), 7.34 (d, J=7.8 Hz, 1H), 7.25 (s, 1H), 7.16 (m, 1H), 7.15 (m, 1H), 7.11 (m, 1H), 6.97 (m, 1H), 6.43 (m, 1H), 3.25 (m, 4H), 3.19 (m, 4H), 2.33 (s, 3H), 2.25 (s, 3H) ppm.

Preparation of Salts of High Purity Via the Base Formed from the Mandelic Acid Salt

Example 8

Preparation of the 1-[2-(2,4-dimethyl-phenylsulfanyl)-phenyl]-piperazine citric acid (2:1) salt (vortioxetine hemicitrate of the Formula XI)

300 mg (1.0 millimoles) of the 1-[2-(2,4-dimethyl-phenylsulfanyl)-phenyl]-piperazine base prepared according to Example 4 are dissolved in 6 ml of acetone under reflux whereupon to the hot solution 114 mg (0.6 millimole) of citric acid in 2 ml of acetone is added. From the hot solution the precipitation of crystals immediately begins. The suspension is stirred at room temperature for 6 hours and allowed to stand at 4° C. overnight. The crystals are filtered, washed with cold acetone and dried. Yield 350 mg (71%). The white crystals melt at 183-186° C., HPLC purity 99.9%.

The NMR and XRPD data of the product correspond to those disclosed in Example 6.

Example 8/A

Preparation of the 1-[1-(2,4-dimethyl-phenylsulfanyl)-phenyl]-piperazine citric acid (2:1) salt (vortioxetine hemicitrate of the Formula XI)

6.0 g (20.0 millimoles) of 1-[2-(2,4-dimethyl-phenylsulfanyl)-phenyl]-piperazine base are suspended in 120 ml of acetone. The suspension is heated to reflux temperature. To the hot solution 2.31 g (12.0 millimoles) of citric acid dissolved in 225 ml of acetone is added. The precipitation of crystals immediately begins. On manual treatment the oily product becomes crystalline and can be easily stirred. The suspension is stirred at room temperature for 6 hours and thereafter allowed to stand at 4° C. overnight. The crystals are filtered, washed with cold acetone and dried. Yield 7.2 g (88.6%). The white crystals melt at 183-186° C. Purity: >99.9%.

The NMR and XRPD data of the product correspond to those disclosed in Example 6.

Example 9

Preparation of 1-[2-(2,4-dimethyl-phenylsulfanyl)-phenyl]-piperazine oxalic acid (1:1) salt (X) (vortioxetine monooxalate)

300 mg (1.0 millimoles) of 1-[2-(2,4-dimethyl-phenylsulfanyl)-phenyl]-piperazine base obtained according to Example 4 are dissolved in 6 ml of acetone under reflux. To the hot solution 108 mg (1.2 millimoles) of oxalic acid dissolved in 2 ml of acetone are added. From the hot solution the precipitation of crystals immediately begins. The suspension is stirred at room temperature for 3 hours and thereafter allowed to stand at 4° C. overnight. The crystals are filtered, washed with cold acetone and dried. Yield 360 mg (93%). The white crystals melt at 185-188° C., HPLC purity larger than 99.9%.The NMR and XRPD data of the product correspond to those disclosed in Example 6.

Example 9/A

Preparation of the 1-[2-(2,4-dimethyl-phenylsulfanyl)-phenyl]-piperazine monooxalate salt of the Formula X 6.0 g (20.0 millimoles) of 1-[2-(2,4-dimethyl-phenylsulfanyl)-phenyl]-piperazine base prepared according to Example 4 are suspended in 120 ml of acetone. The suspension is heated under reflux. To the hot solution thus obtained 2.06 g (24.0 millimoles) of oxalic acid dissolved in 25 ml of acetone are added. An abundant crystal precipitation immediately starts. The suspension is stirred at room temperature for 6 hours and thereafter allowed to stand at 4° C. overnight. The crystals are filtered, washed with cold acetone and dried to constant weight. Yield 7.19 g (92.5%). The white crystals melt at 185-188° XC. HPL purity larger than 99.9%. The NMR and XRPD data correspond to those disclosed in Example 5.

Example 10

Preparation of the 1-[2-(2,4-dimethyl-phenylsulfanyl)-phenyl]-piperazine hydrobromide salt (beta polymorph)

300 mg (1.0 millimole) of 1-[2-(2,4-dimethyl-phenylsulfanyl)-phenyl]-piperazine base prepared according to Example 4 are dissolved in 6 ml of acetone under reflux. To the hot solution thus obtained 0.113 g (1.0 millimole) of a 48% aqueous hydrobromic acid solution is added. From the hot solution the precipitation of crystals immediately begins. The suspension is stirred at room temperature for 3 hours and then allowed to stand at 4° C. overnight. The crystals are filtered, washed with cold acetone and dried. Yield 0.27 g (70.6%). Mp.: 226-228° C. HPLC purity 99.81%. The NMR and XRPD data of the product correspond to those disclosed in Example 7.

Example 11

Preparation of the 1-[2-(2,4-dimethyl-phenylsulfanyl)-phenyl]-piperazine salicylic acid (1:1) salt (vortioxetine salicylate of the Formula XIII)

400 mg (1.34 millimole) of 1-[2-(2,4-dimethyl-phenylsulfanyl)-phenyl]-piperazine base are dissolved in 8 ml of acetone under reflux. To the hot solution thus obtained 185 mg (1.34 millimole) of salicylic acid dissolved in 2 ml of acetone are added. The reaction mixture is cooled to room temperature; the solvent is evaporated in vacuo. The residue is crystallized from 1 ml of acetone. The crystals obtained are filtered, washed with cold acetone and dried in a refrigerator at 80° C. for 6 hours. The white crystals melt at 179-184° C., yield 510 mg (87%).

IR (KBr): 2488, 1638, 1474, 1457, 1381, 763 cm$^{-1}$.

1H-NMR (CDCl3, 400 MHz): δ 7.94 (m, 1H), 7.36 (m, 1H), 7.32 (d, J=7.8 Hz, 1H), 7.14 (s, 1H), 7.05 (m, 1H), 7.02 (m, 1H), 6.97 (m, 1H), 6.95 (m, 1H), 6.91 (m, 1H), 6.86 (m, 1H), 6.53 (dd, J1=1.2 Hz, J2=7.9 Hz, 1H), 3.41 (m, 4H), 3.29 (m, 4H), 2.35 (s, 3H), 2.29 (s, 3H) ppm.

The X-ray powder diffraction data of the vortioxetine salicylic acid (1:1) salt are disclosed in the following Table (relative intensities>2%).

| Peak | 2θ (°) | d (Å) | Relative intensity (%) |
|---|---|---|---|
| 1 | 8.44 | 10.47 | 18 |
| 2 | 11.66 | 7.58 | 27 |
| 3 | 12.41 | 7.12 | 7 |
| 4 | 13.22 | 6.69 | 22 |
| 5 | 13.73 | 6.45 | 71 |
| 6 | 14.39 | 6.15 | 64 |
| 7 | 16.60 | 5.34 | 100 |

-continued

| Peak | 2θ (°) | d (Å) | Relative intensity (%) |
|---|---|---|---|
| 8 | 16.84 | 5.26 | 47 |
| 9 | 17.57 | 5.04 | 23 |
| 10 | 17.83 | 4.97 | 34 |
| 11 | 18.61 | 4.76 | 51 |
| 12 | 19.03 | 4.66 | 6 |
| 13 | 19.57 | 4.53 | 14 |
| 14 | 19.81 | 4.48 | 42 |
| 15 | 20.30 | 4.37 | 39 |
| 16 | 21.55 | 4.12 | 10 |
| 17 | 21.82 | 4.07 | 9 |
| 18 | 32.10 | 2.79 | 10 |
| 19 | 29.04 | 3.07 | 9 |
| 20 | 22.05 | 4.03 | 17 |
| 21 | 22.60 | 3.93 | 30 |
| 22 | 23.06 | 3.85 | 28 |
| 23 | 21.07 | 4.21 | 12 |
| 24 | 17.08 | 5.19 | 19 |
| 25 | 10.21 | 8.65 | 3 |
| 26 | 23.45 | 3.79 | 17 |
| 27 | 24.00 | 3.71 | 25 |
| 28 | 24.24 | 3.67 | 13 |
| 29 | 24.96 | 3.56 | 8 |
| 30 | 25.24 | 3.53 | 26 |
| 31 | 25.63 | 3.47 | 7 |
| 32 | 26.06 | 3.42 | 28 |
| 33 | 27.30 | 3.26 | 23 |
| 34 | 27.66 | 3.22 | 7 |
| 35 | 27.99 | 3.18 | 23 |
| 36 | 28.47 | 3.13 | 8 |
| 37 | 28.80 | 3.10 | 22 |
| 38 | 29.28 | 3.05 | 3 |
| 39 | 29.98 | 2.98 | 8 |
| 40 | 30.57 | 2.92 | 5 |
| 41 | 30.90 | 2.89 | 6 |
| 42 | 32.38 | 2.76 | 4 |
| 43 | 33.57 | 2.67 | 3 |
| 44 | 33.87 | 2.64 | 5 |

Example 12

Preparation of the 1-[2-(2,4-dimethyl-phenylsulfanyl)-phenyl]-piperazine citric acid [1:1] salt (vortioxetine monocitrate monohydrate of the Formula XIV 100 mg (0.335 millimole) of 1-[2-(2,4-dimethyl-phenylsulfanyl)-phenyl]-piperazine base are dissolved in a mixture of 2 ml of acetone and 0.2 ml of water under reflux. To the hot solution 320 mg (1.67 millimole) of citric acid in 2 ml of acetone are added. From the hot solution the precipitation of crystals immediately begins. The suspension thus obtained is stirred at room temperature for 6 hours and then allowed to stand at 4° C. overnight. The crystals are filtered, washed with cold acetone and dried. Yield 90 mg (53%). The white crystals melt at 126-129° C.

IR (KBr): 3454, 2528, 1702, 1679, 1582, 1311, 1234 cm$^{-1}$.

$^1$H-NMR (DMSO-d$_6$, 400 MHz): δ 10.46 (b, 3H), 7.33 (d, J=7.8 Hz, 1H), 7.25 (s, 1H), 7.16 (m, 1H), 7.15 (m, 1H), 7.11 (m, 1H), 6.97 (m, 1H), 6.42 (m, 1H), 3.23 (m, 4H), 3.16 (m, 4H), 2.55 (d, J=15.1 Hz, 2H), 2.48 (d), 2.33 (s, 3H), 2.24 (s, 3H) ppm.

The loss of weight of the product obtained according to the process amounts to 3.3% by weight measured by TG (calc. 3.6% by weight).

The characteristic X-ray powder diffraction data of the citric acid [1:1] salt (vortioxetine monocitrate monohydrate) are disclosed in the following Table:

(relative intensities> than 2%)

| Peak | 2θ (°) | d (Å) | Relative intensity (%) |
|---|---|---|---|
| 1 | 11.66 | 7.58 | 90 |
| 2 | 11.97 | 7.39 | 5 |
| 3 | 12.76 | 6.93 | 10 |
| 4 | 13.89 | 6.37 | 48 |
| 5 | 14.17 | 6.24 | 15 |
| 6 | 14.98 | 5.91 | 45 |
| 7 | 16.36 | 5.42 | 52 |
| 8 | 17.00 | 5.21 | 100 |
| 9 | 18.17 | 4.88 | 11 |
| 10 | 18.58 | 4.77 | 7 |
| 11 | 19.8 | 4.48 | 11 |
| 12 | 20.82 | 4.26 | 9 |
| 13 | 21.27 | 4.17 | 6 |
| 14 | 22.04 | 4.03 | 3 |
| 15 | 22.65 | 3.92 | 81 |
| 16 | 23.42 | 3.79 | 4 |
| 17 | 24.09 | 3.69 | 48 |
| 18 | 24.84 | 3.58 | 6 |
| 19 | 25.61 | 3.48 | 5 |
| 20 | 26.98 | 3.3 | 10 |
| 21 | 27.26 | 3.27 | 10 |
| 22 | 28.42 | 3.14 | 8 |
| 23 | 29.09 | 3.07 | 9 |
| 24 | 29.63 | 3.01 | 3 |
| 25 | 30.42 | 2.94 | 4 |
| 26 | 30.82 | 2.90 | 3 |
| 27 | 32.69 | 2.74 | 6 |
| 28 | 33.54 | 2.67 | 7 |
| 29 | 34.36 | 2.61 | 13 |
| 30 | 34.68 | 2.58 | 6 |

Example 13

Preparation of the 1-[2-(2,4-dimethyl-phenylsulfanyl)-phenyl]-piperazine citric acid [1:1] salt (vortioxetine monocitrate anhydrate of the (Formula XX)

100 mg (0.335 mole) of 1-[2-(2,4-dimethyl-phenylsulfanyl)-phenyl]-piperazine base are dissolved in 2 ml of acetone under reflux whereupon to the hot solution thus obtained 320 mg (1.67 millimoles) of citric acid dissolved in 2 ml of acetone are added. From the hot solution the precipitation of crystals starts immediately. The suspension is stirred at room temperature for 6 hours and thereafter allowed to stand at 4° C. overnight. The crystals are filtered, washed with cold acetone and dried. Yield 120 mg (73%). The white crystals melt at 152-154° C.

IR (KBr): 3351, 3139, 2518, 1735, 1686, 1628, 1440, 1403, 1199, 1044 cm$^{-1}$.

$^1$H-NMR (CD$_3$OD-CDCl$_3$, 500 MHz): δ 7.29 (d, J=7.8 Hz, 1H), 7.20 (bs, 1H), 7.17 (m, 1H), 7.13 (m, 1H), 7.06 (m, 1H), 6.93 (m, 1H), 6.54 (m, 1H), 3.37 (m, 4H), 3.28 (m, 4H), 2.83 (d, J=15.5 Hz, 2H), 2.74 (d, J=15.4 Hz, 2H), 2.35 (s, 3H), 2.28 (s, 3H) ppm.

The characteristic X-ray diffraction data of the citric acid (1:1) salt (vortioxetine monocitrate anhydrate) are summarized in the following Table:
(relative intensities>2%)

| Peak | 2θ (°) | d (Å) | Relative intensity (%) |
|---|---|---|---|
| 1 | 5.52 | 16.01 | 100 |
| 2 | 10.33 | 8.56 | 6 |
| 3 | 10.94 | 8.08 | 3 |
| 4 | 12.38 | 7.14 | 71 |
| 5 | 13.20 | 6.70 | 15 |
| 6 | 13.91 | 6.36 | 13 |
| 7 | 14.56 | 6.08 | 29 |
| 8 | 15.62 | 5.67 | 10 |
| 9 | 16.26 | 5.45 | 47 |
| 10 | 16.61 | 5.33 | 93 |
| 11 | 18.12 | 4.89 | 78 |
| 12 | 18.83 | 4.71 | 6 |
| 13 | 20.68 | 4.29 | 20 |
| 14 | 20.89 | 4.25 | 33 |
| 15 | 21.34 | 4.16 | 6 |
| 16 | 22.10 | 4.02 | 13 |
| 17 | 22.91 | 3.88 | 24 |
| 18 | 23.41 | 3.80 | 17 |
| 19 | 24.37 | 3.65 | 11 |
| 20 | 24.85 | 3.58 | 33 |
| 21 | 25.60 | 3.48 | 26 |
| 22 | 26.37 | 3.38 | 16 |
| 23 | 27.93 | 3.19 | 15 |
| 24 | 28.45 | 3.13 | 13 |
| 25 | 29.37 | 3.04 | 7 |
| 26 | 31.15 | 2.87 | 11 |
| 27 | 31.97 | 2.80 | 4 |
| 28 | 32.89 | 2.72 | 7 |

Example 14

Preparation of the 1-[2-(2,4-dimethyl-phenylsulfanyl)-phenyl]-piperazine malonic acid [1:1] salt (vortioxetine malonate of the Formula XV)

300 mg (1.0 mole) of 1-[2-(2,4-dimethyl-phenylsulfanyl)-phenyl]-piperazine base are dissolved in 6 ml acetone at room temperature whereupon to the hot solution thus obtained 100 mg (1.0 millimole) of malonic acid dissolved in 2 ml of acetone are added. The reaction mixture is cooled to room temperature; the solvent is evaporated in vacuo. The oily residue is crystallized from 1 ml of acetone. The crystals are filtered, washed with cold acetone and dried in a refrigerator under a pressure of 8 mbar in vacuo at 80° C. for 6 hours. Yield 350 mg (87%). The white crystals melt at 126-129° C.

IR (KBr): 3478, 3029, 2490, 1718, 1580, 1469, 1374 cm$^{-1}$.

$^1$H-NMR (DMSO-$d_6$, 400 MHz): δ 7.33 (d, J=7.8 Hz, 1H), 7.25 (s, 1H), 7.15 (m, 2H), 7.11 (m, 1H), 6.97 (m, 1H), 6.42 (m, 1H), 3.23 (m, 4H), 3.17 (m, 4H), 2.72 (s, 2H), 2.33 (s, 3H), 2.24 (s, 3H) ppm.

The characteristic X-ray powder diffraction peaks of the vortioxetine malonic acid [1:1] salt are summarized in the following Table
(relative intensity> than 2%)

| Peak | 2θ (°) | d (Å) | Relative intensity (%) |
|---|---|---|---|
| 1 | 5.11 | 17.26 | 71 |
| 2 | 10.46 | 8.45 | 59 |
| 3 | 11.93 | 7.41 | 34 |
| 4 | 14.77 | 5.99 | 24 |
| 5 | 15.21 | 5.82 | 63 |
| 6 | 16.05 | 5.52 | 31 |
| 7 | 16.58 | 5.34 | 11 |
| 8 | 17.35 | 5.11 | 15 |
| 9 | 17.91 | 4.95 | 25 |
| 10 | 18.30 | 4.84 | 28 |
| 11 | 18.71 | 4.74 | 100 |
| 12 | 19.64 | 4.52 | 9 |
| 13 | 19.98 | 4.44 | 16 |
| 14 | 20.42 | 4.35 | 76 |
| 15 | 20.64 | 4.30 | 28 |
| 16 | 20.93 | 4.24 | 9 |
| 17 | 21.58 | 4.12 | 9 |
| 18 | 22.53 | 3.94 | 7 |
| 19 | 22.79 | 3.90 | 20 |
| 20 | 23.03 | 3.86 | 8 |
| 21 | 24.22 | 3.67 | 28 |
| 22 | 24.60 | 3.62 | 7 |
| 23 | 25.77 | 3.45 | 19 |
| 24 | 26.44 | 3.37 | 14 |
| 25 | 26.95 | 3.31 | 10 |
| 26 | 27.19 | 3.28 | 10 |
| 27 | 27.66 | 3.22 | 12 |
| 28 | 29.23 | 3.05 | 8 |
| 29 | 29.45 | 3.03 | 11 |
| 30 | 30.66 | 2.91 | 8 |
| 31 | 30.95 | 2.89 | 8 |
| 32 | 31.79 | 2.81 | 7 |

Example 15

Preparation of the 1-[2-(2,4-dimethyl-phenylsulfanyl)-phenyl]-piperazine oxalic acid [2:1] salt (vortioxetine hemioxalate of the Formula XVI)

300 mg (1.0 millimole) of 1-[2-(2,4-dimethyl-phenylsulfanyl)-phenyl]-piperazine base are dissolved in 6 ml of acetone under reflux and to the hot solution thus obtained 54 mg (0.6 millimole) of oxalic acid dissolved in 1.2 ml of acetone are added. From the hot solution the precipitation of crystals immediately begins. The suspension is stirred at room temperature for 5 hours and then allowed to stand overnight. The crystals are filtered, washed with cold acetone and dried. Yield 270 mg (93%). The white crystals melt at 199-208° C.

IR (KBr): 2756, 2509, 1915, 1653, 1474, 1209, 705 cm$^{-1}$.

$^1$H-NMR (DMSO-$d_6$, 400 MHz): δ 7.33 (d, J=7.8 Hz, 1H), 7.25 (s, 1H), 7.14 (m, 2H), 7.10 (m, 1H), 6.95 (m, 1H), 6.41 (m, 1H), 3.17 (m, 4H), 3.13 (m, 4H), 2.33 (s, 3H), 2.24 (s, 3H) ppm.

$^{13}$CNMR (DMSO-$d_6$, 100 MHz): δ 163.39, 148.06, 141.79, 139.44, 135.86, 133.56, 131.92, 128.22, 127.05, 126.18, 126.00, 125.25, 120.46, 48.42, 43.56, 20.87, 20.23 ppm.

X-ray powder diffraction data of the vortioxetine oxalic acid [1:2] salt:
(relative intensities>2%)

| Peak | 2θ (°) | d (Å) | Relative intensity (%) |
|---|---|---|---|
| 1 | 11.67 | 7.58 | 6 |
| 2 | 12.00 | 7.37 | 17 |
| 3 | 13.79 | 6.42 | 7 |
| 4 | 14.27 | 6.20 | 17 |
| 5 | 15.43 | 5.74 | 97 |
| 6 | 16.32 | 5.43 | 24 |
| 7 | 16.96 | 5.22 | 50 |
| 8 | 17.48 | 5.07 | 100 |
| 9 | 18.42 | 4.81 | 7 |
| 10 | 18.85 | 4.70 | 14 |
| 11 | 19.89 | 4.46 | 18 |
| 12 | 20.43 | 4.34 | 13 |
| 13 | 20.89 | 4.25 | 11 |
| 14 | 21.71 | 4.09 | 4 |

| Peak | 2θ (°) | d (Å) | Relative intensity (%) |
|---|---|---|---|
| 15 | 22.08 | 4.02 | 4 |
| 16 | 22.85 | 3.89 | 57 |
| 17 | 23.22 | 3.83 | 13 |
| 18 | 23.41 | 3.80 | 10 |
| 19 | 23.85 | 3.73 | 6 |
| 20 | 24.49 | 3.63 | 22 |
| 21 | 25.14 | 3.54 | 23 |
| 22 | 25.72 | 3.46 | 10 |
| 23 | 26.33 | 3.38 | 3 |
| 24 | 28.12 | 3.17 | 6 |
| 25 | 28.51 | 3.13 | 6 |
| 26 | 29.49 | 3.03 | 3 |
| 27 | 29.97 | 2.98 | 5 |
| 28 | 30.38 | 2.94 | 3 |
| 29 | 30.92 | 2.89 | 4 |
| 30 | 31.62 | 2.83 | 2 |
| 31 | 32.50 | 2.75 | 3 |
| 32 | 32.90 | 2.72 | 4 |
| 33 | 34.59 | 2.59 | 3 |
| 34 | 34.81 | 2.57 | 5 |

Example 16

Preparation of the 1-[2-(2,4-dimethyl-phenylsulfanyl)-phenyl]-piperazine L-malic acid [1:1] salt (vortioxetine L-malate of the Formula XVII)

300 mg (1.0 millimole) of 1-[2-(2,4-dimethyl-phenylsulfanyl)-phenyl]-piperazine base are dissolved in 6 ml of acetone under reflux, whereupon to the hot solution 130 mg (1.0 millimole) of L-malic acid in 2 ml of acetone are added. From the hot solution the precipitation of crystals immediately begins. The suspension is stirred at room temperature for 6 hours and then allowed to stand at room temperature overnight. The crystals are filtered, washed with cold acetone and dried. Yield 380 mg (88%). The white crystals melt at 127-130° C.

IR (KBr): 2492, 1716, 1634, 1472, 1454, 1228, 1045 $cm^{-1}$.

$^1$H-NMR (DMSO-$d_6$, 400 MHz): δ 9.75 (br s, 4H), 7.33 (d, J=7.8 Hz, 1H), 7.25 (s, 1H), 7.15 (m, 1H), 7.14 (m, 1H), 7.10 (m, 1H), 6.95 (m, 1H), 6.42 (m, 1H), 3.87 (dd, J1=3.8 Hz, J2=10.2 Hz, 1H), 3.18 (m, 4H), 3.12 (m, 4H), 2.50 (m, 1H), 2.33 (s, 3H), 2.32 (m, 1H), 2.24 (s, 3H) ppm.

X-ray powder diffraction data of the vortioxetine L-malic acid [1:1] salt
(relative intensities>2%)

| Peak | 2θ (°) | d (Å) | Relative intensity (%) |
|---|---|---|---|
| 1 | 4.05 | 21.78 | 44 |
| 2 | 8.06 | 10.96 | 19 |
| 3 | 12.08 | 7.32 | 100 |
| 4 | 12.57 | 7.04 | 23 |
| 5 | 13.40 | 6.60 | 46 |
| 6 | 13.58 | 6.52 | 76 |
| 7 | 14.36 | 6.17 | 5 |
| 8 | 15.65 | 5.66 | 11 |
| 9 | 16.13 | 5.49 | 16 |
| 10 | 16.97 | 5.22 | 49 |
| 11 | 18.12 | 4.89 | 28 |
| 12 | 19.58 | 4.53 | 84 |
| 13 | 20.63 | 4.30 | 14 |
| 14 | 21.77 | 4.08 | 15 |
| 15 | 22.61 | 3.93 | 43 |
| 16 | 23.49 | 3.78 | 33 |
| 17 | 23.96 | 3.71 | 24 |
| 18 | 24.26 | 3.67 | 48 |
| 19 | 25.29 | 3.52 | 16 |
| 20 | 27.08 | 3.29 | 15 |
| 21 | 27.72 | 3.22 | 17 |
| 22 | 28.34 | 3.15 | 18 |

Example 17

Preparation of the 1-[2-(2,4-dimethyl-phenylsulfanyl)-phenyl]-piperazine benzenesulfonic acid [1:1] salt of the Formula XVIII 300 mg of 1-[2-(2,4-dimethyl-phenylsulfanyl)-phenyl]-piperazine base are dissolved in 6 ml of acetone whereupon to the hot solution 160 mg (1.0 millimole) of benzenesulfonic acid dissolved in 2 ml of acetone are added. From the hot solution the crystallization of crystals immediately begins. The suspension is stirred at room temperature for 6 hours and thereafter allowed to stand at 4° C. overnight. The crystals are filtered, washed with cold acetone and dried. Yield 430 mg (94%). The white crystals melt at 178-181° C.

IR (KBr): 3050, 2496, 1224, 1192, 1124, 1016, 611 $cm^{-1}$.

$^1$H-NMR (CDCl$_3$, 400 MHz): δ 9.10 (br s, 2H), 7.95 (m, 2H), 7.44 (m, 3H), 7.32 (d, J=7.8 Hz, 1H), 7.14 (s, 1H), 7.05 (m, 1H), 7.02 (m, 1H), 6.97 (m, 1H), 6.90 (m, 1H), 6.52 (dd, J1=1.5 Hz, J2=7.9 Hz, 1H), 3.44 (m, 4H), 3.29 (m, 4H), 2.35 (s, 3H), 2.28 (s, 3H) ppm.

The X-ray powder diffraction data of the vortioxetine benzene sulfonic acid [1:1] salt are summarized in the following Table:
(relative intensities>2%)

| Peak | 2θ (°) | d (Å) | Relative intensity (%) |
|---|---|---|---|
| 1 | 5.83 | 15.15 | 18 |
| 2 | 7.81 | 11.31 | 49 |
| 3 | 8.04 | 10.99 | 17 |
| 4 | 11.19 | 7.90 | 10 |
| 5 | 11.64 | 7.60 | 7 |
| 6 | 13.49 | 6.56 | 24 |
| 7 | 14.30 | 6.19 | 13 |
| 8 | 14.79 | 5.98 | 100 |
| 9 | 15.35 | 5.77 | 19 |
| 10 | 15.63 | 5.67 | 58 |
| 11 | 16.08 | 5.51 | 43 |
| 12 | 16.56 | 5.35 | 33 |
| 13 | 17.61 | 5.03 | 66 |
| 14 | 18.28 | 4.85 | 35 |
| 15 | 18.51 | 4.79 | 66 |
| 16 | 19.54 | 4.54 | 83 |
| 17 | 20.44 | 4.34 | 17 |
| 18 | 20.83 | 4.26 | 3 |
| 19 | 21.27 | 4.17 | 6 |
| 20 | 21.55 | 4.12 | 20 |
| 21 | 22.03 | 4.03 | 17 |
| 22 | 22.53 | 3.94 | 37 |
| 23 | 22.79 | 3.90 | 28 |
| 24 | 23.53 | 3.78 | 62 |
| 25 | 24.11 | 3.69 | 12 |
| 26 | 24.71 | 3.60 | 12 |
| 27 | 24.92 | 3.57 | 24 |
| 28 | 25.76 | 3.46 | 15 |
| 29 | 26.22 | 3.40 | 4 |
| 30 | 26.46 | 3.37 | 3 |
| 31 | 27.03 | 3.30 | 23 |
| 32 | 27.50 | 3.24 | 6 |
| 33 | 28.28 | 3.15 | 7 |
| 34 | 28.77 | 3.10 | 9 |

Example 18

Preparation of the 1-[2-(2,4-dimethyl-phenylsulfanyl)-phenyl]-piperazine acetic acid salt (vortioxetine acetate of the Formula XIX)

300 mg (1.0 millimole) of 1-[2-(2,4-dimethyl-phenylsulfanyl)-phenyl]-piperazine base are dissolved in 6 ml of acetone under reflux whereupon to the hot solution 0.06 ml (1.0 millimole) of acetic acid dissolved in 2 ml of acetone is added. The solution is cooled to room temperature, whereby slow precipitation of crystals begins. The suspension is stirred at room temperature for 6 hours and thereafter allowed to stand at 4° C. overnight. The crystals are filtered, washed with cold acetone and dried. Yield 140 mg (39%). The white crystals melt at 106-108° C.

IR (KBr): 2398, 1580, 1470, 1440, 1040, 759 cm$^{-1}$.

$^1$H-NMR (DMSO-d$_6$, 400 MHz): δ 7.32 (d, J=7.8 Hz, 1H), 7.23 (s, 1H), 7.10 (m, 2H), 7.08 (m, 1H), 6.88 (m, 1H), 6.38 (d, J=7.7 Hz, 1H), 2.89 (m, 4H), 2.85 (m, 4H), 2.32 (s, 3H), 2.23 (s, 3H), 1.90 (s, 3H) ppm.

Figure 10:
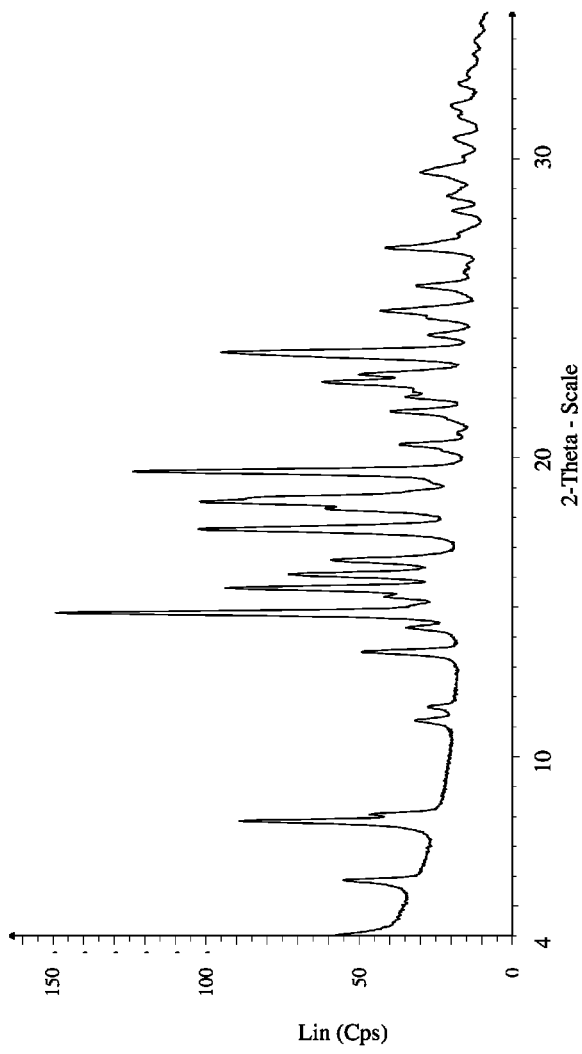
FIG. 10./Drawing 10: X-ray powder diffractogram of the vortioxetine benzenesulfonic acid salt [1:1] of the Formula XVIII.
Figure 11:
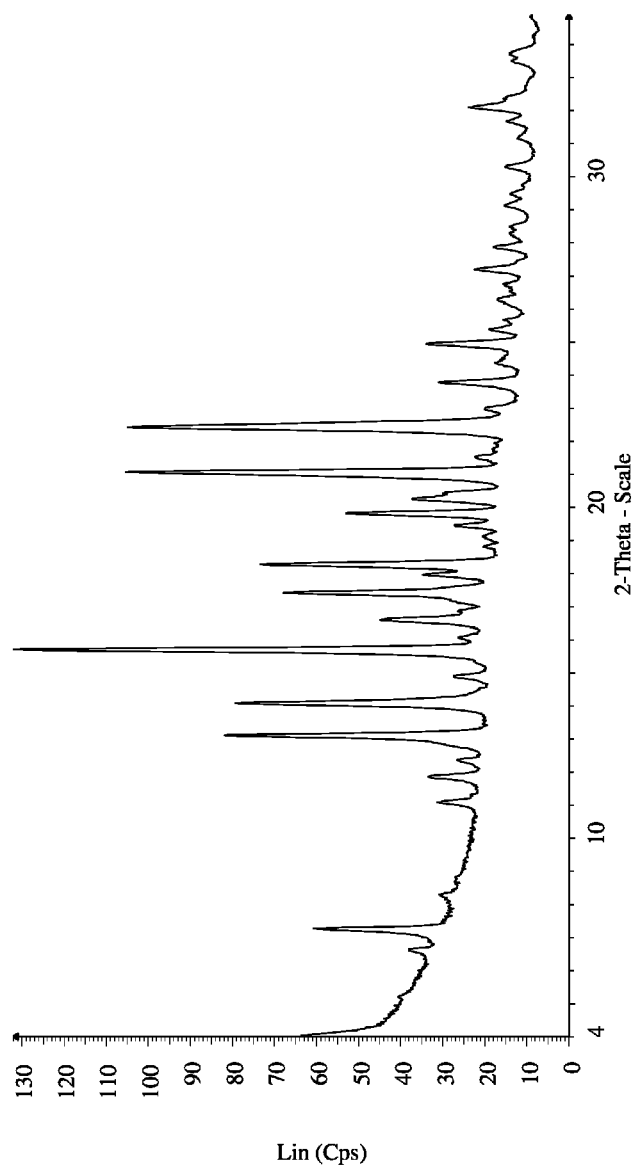
FIG. 11./Drawing 11: X-ray powder diffractogram of the vortioxetine acetic acid [1:1] salt of the Formula XIX.
Figure 12:
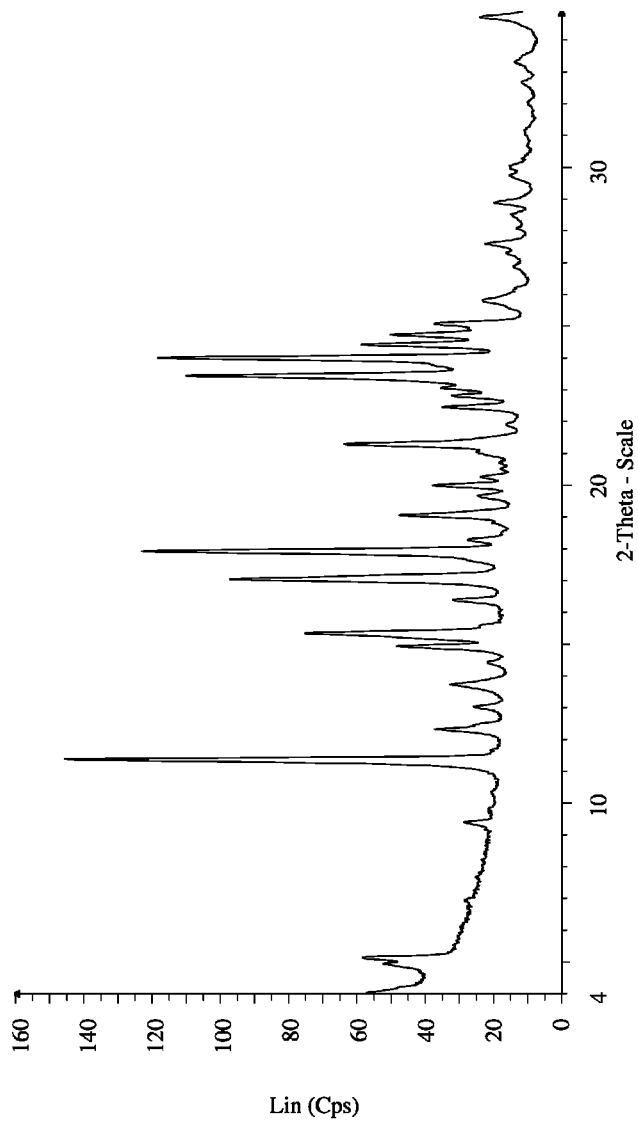
FIG. 12./Drawing 12: X-ray powder diffractogram of the vortioxetine succinate [1:1] salt of the Formula XII.
Figure 13:
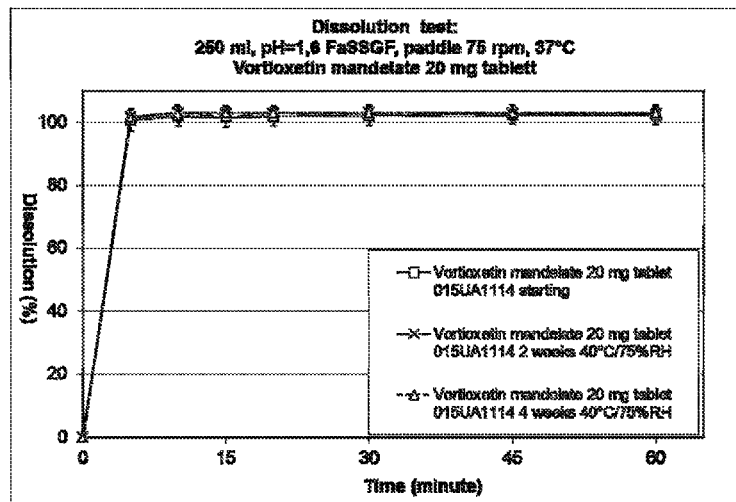
FIG. 13./Drawing 13: Dissolution curve of vortioxetine mandelate containing immediate release tablets (250 ml, pH 1.6 FaSSGF, paddle, 75 rpm, 37° C.) at the starting point of the test and 2 weeks and 4 weeks after storage (40° C./75% RH).

The X-ray powder diffraction data of the acetic acid salt are shown on FIG. 10 and the characteristic X-ray powder diffraction data are summarized in Table 10.

TABLE 10

| Peak | 2θ (°) | d (Å) | Relative intensity (%) |
|---|---|---|---|
| 1 | 6.59 | 13.41 | 5 |
| 2 | 7.22 | 12.23 | 27 |
| 4 | 11.07 | 7.99 | 8 |
| 5 | 11.83 | 7.47 | 11 |
| 6 | 12.34 | 7.17 | 5 |
| 7 | 12.79 | 6.92 | 8 |
| 8 | 13.08 | 6.76 | 54 |
| 9 | 14.06 | 6.30 | 53 |
| 10 | 14.87 | 5.95 | 8 |
| 11 | 15.68 | 5.65 | 100 |
| 12 | 16.06 | 5.52 | 7 |
| 13 | 16.59 | 5.34 | 24 |
| 14 | 16.87 | 5.25 | 8 |
| 15 | 17.41 | 5.09 | 45 |
| 16 | 17.96 | 4.93 | 16 |
| 17 | 18.26 | 4.85 | 50 |
| 20 | 19.44 | 4.56 | 10 |
| 21 | 19.82 | 4.48 | 33 |
| 22 | 20.25 | 4.38 | 20 |
| 23 | 20.42 | 4.35 | 14 |
| 24 | 21.06 | 4.21 | 80 |
| 25 | 21.52 | 4.13 | 7 |
| 27 | 22.44 | 3.96 | 81 |
| 28 | 22.98 | 3.87 | 6 |
| 29 | 23.77 | 3.74 | 16 |
| 31 | 24.95 | 3.57 | 20 |
| 32 | 25.38 | 3.51 | 7 |
| 34 | 26.30 | 3.39 | 6 |
| 36 | 27.21 | 3.27 | 11 |
| 37 | 27.87 | 3.20 | 7 |
| 40 | 29.16 | 3.06 | 5 |
| 42 | 30.32 | 2.95 | 6 |
| 44 | 31.69 | 2.82 | 6 |
| 45 | 32.12 | 2.78 | 14 |
| 46 | 32.40 | 2.76 | 7 |
| 47 | 33.52 | 2.67 | 6 |
| 48 | 33.75 | 2.65 | 6 |

X-ray powder diffraction data of the vortioxetine acetic acid salt (1:1)

(relative intensities>2%)

Example 19

Preparation of 1-[2-(2,4-dimethyl-phenylsulfanyl)-phenyl]-piperazine succinic acid salt (vortioxetine succinate of the Formula XII)

300 mg (1.0 millimole) of 1-[2-(2,4-dimethyl-phenylsulfanyl)-phenyl]-piperazine are dissolved in 6 ml of acetone under reflux whereupon to the hot solution 120 mg (1.0 millimole) of succinic acid dissolved in 2 ml of acetone are added. From the hot solution the precipitation of crystals begins. The suspension is stirred at room temperature for 6 hours and thereafter allowed to stand at 4° C. overnight. The crystals are filtered, washed with cold acetone and dried. Yield 370 mg (89%). Melting point: 146-149° C.

Elementary analysis $C_{22}H_{28}N_2O_4S$ (416.54) calculated for the Formula:

| | | | | |
|---|---|---|---|---|
| Calc [%] | C: 63.44 | H: 6.78 | N: 6.73 | S: 7.70 |
| Found [%] | C: 63.11 | H: 6.78 | N: 6.63 | S: 7.60 |

IR (KBr): 2739, 2529, 1720, 1632, 1581, 1472, 1043 cm$^{-1}$.

$^1$H-NMR (DMSO-d$_6$, 400 MHz): δ 7.33 (d, J=7.8 Hz, 1H), 7.24 (s, 1H), 7.13 (m, 2H), 7.09 (m, 1H), 6.92 (m, 1H), 6.40 (m, 1H), 3.03 (s, 8H), 2.33 (s, 3H), 2.33 (s, 4H), 2.24 (s, 3H) ppm.

The X-ray powder diffraction data of the vortioxetine succinic acid (1:1) salt (relative intensities>2%)

| Peak | 2θ (°) | d (Å) | Relative intensity (%) |
|---|---|---|---|
| 1 | 4.90 | 18.02 | 13 |
| 2 | 5.10 | 17.32 | 19 |
| 3 | 9.36 | 9.45 | 7 |
| 4 | 11.33 | 7.80 | 100 |
| 5 | 12.29 | 7.19 | 15 |
| 6 | 13.00 | 6.80 | 7 |
| 7 | 13.70 | 6.46 | 13 |
| 8 | 14.39 | 6.15 | 4 |
| 9 | 14.91 | 5.94 | 26 |
| 10 | 15.32 | 5.78 | 47 |
| 11 | 16.37 | 5.41 | 13 |
| 12 | 17.03 | 5.20 | 65 |
| 13 | 17.91 | 4.95 | 85 |
| 14 | 18.27 | 4.85 | 10 |
| 15 | 19.05 | 4.66 | 27 |
| 16 | 19.64 | 4.52 | 9 |
| 17 | 19.99 | 4.44 | 19 |
| 18 | 20.26 | 4.38 | 8 |
| 19 | 21.28 | 4.17 | 40 |
| 20 | 21.90 | 4.06 | 3 |
| 21 | 22.46 | 3.96 | 18 |
| 22 | 22.81 | 3.90 | 16 |
| 23 | 23.08 | 3.85 | 19 |
| 24 | 23.44 | 3.79 | 77 |
| 25 | 24.00 | 3.71 | 84 |
| 26 | 24.42 | 3.64 | 38 |
| 27 | 24.72 | 3.60 | 31 |
| 28 | 25.08 | 3.55 | 21 |
| 29 | 25.81 | 3.45 | 10 |
| 30 | 27.32 | 3.26 | 5 |
| 31 | 27.59 | 3.23 | 10 |
| 32 | 28.50 | 3.13 | 5 |
| 33 | 28.90 | 3.09 | 9 |
| 34 | 29.75 | 3.00 | 5 |
| 35 | 30.03 | 2.97 | 6 |
| 36 | 32.67 | 2.74 | 3 |
| 37 | 33.33 | 2.69 | 5 |
| 38 | 34.74 | 2.58 | 11 |

Example 20/A

Preparation of Vortioxetine Mandelate (Compound of the Formula IX) Containing Tablets (Strength: Corresponds to 20 mg of Vortioxetine Base)

| Weight | Name of the product: Vortioxetine 20 mg tablet | |
|---|---|---|
| | Batch Number: 015 UA 1114 mg/tablet | Batch size: about 1 050 g weight (g) |
| Vortioxetine-mandelate ground | 30.196 | 211.37 |
| Microcrystalline cellulose (Avicel PH 101 (FMC)) | 13.620 | 95.34 |
| Mannitol (Pearlitol SD 200) | 88.884 | 622.19 |
| Sodium carboxymethyl starch (Primojel) | 4.500 | 31.50 |
| Hydroxypropyl cellulose (Klucel EXF) | 4.50 | 31.50 |
| Purified water | 0 | 493.50 |
| | 0 | 0 |
| Avicel PH 101 (FMC) | 6.80 | 47.60 |
| Magnesium stearate | 1.50 | 10.50 |
| | 0 | 0 |
| Total: | 150.0 | 1050.0 |

Brief description of the manufacturing process:

a) The components of the internal phase vortioxetine mandelate, microcrystalline cellulose (Avicel PH 101, FMC), mannitol (Pearlitol SD 200) and sodium carboxymethyl starch (Primojel) are admixed, homogenized and granulated with a solution of hydroxypropyl cellulose (Klucel EXF) in a fluidized granulating apparatus (Glatt GPCG 1). The granules thus obtained are dried and regranulated on an oscillating sieve (Frewitt 1.0 mm).

b) The components of the external phase microcrystalline cellulose (Avicel PH 101 FMC) and magnesium stearate are admixed with the granules prepared according to paragraph a). The mixture thus obtained is homogenized.

c) The homogenized mixture prepared according to paragraph b) is pressed on a rotating tableting machine to lentiform tablets (size 9.5×4.5 mm, weight 150 mg). Pressing strength: min. 30N. The chemical stability and dissolution of the tablets thus obtained are tested:

a) Chemical Stability of the Tablets Obtained:

| | | | Amount of the impurity expressed in the percentage of the active ingredient | | |
|---|---|---|---|---|---|
| | | | | Σ Total amount of impurities [%] (>0.03%) | |
| Sample | Storing conditions | Average content % | Σ total. [%] | Σ known [%] | Σ unknown [%] |
| Mandelate salt containing tablet (015UA1114) | Starting | 102.94 | <0.03 | <0.03 | <0.03 |
| | 40° C./75RH %-2 weeks | 102.38 | <0.03 | <0.03 | <0.03 |
| | 40° C./75RH %-4 weeks | 99.37 | 0.03 | <0.03 | 0.03 |

(The results are calculated from 2 parallels measurements. The average content is expressed in the percentage of the theoretical content calculated from the measured value). It can be seen from the Table that the chemical stability of the tablets is excellent.

b) Dissolution Test

The dissolution of the tablets meets the requirements of the immediate release tablets. On advancement of time the dissolution of the tablets does not significantly change which is shown on Drawing 13 and in Table 13:

| 015UA1114 | | Time of sampling (minutes)—dissolution (%) | | | | | | |
|---|---|---|---|---|---|---|---|---|
| | | 5 | 10 | 15 | 20 | 30 | 45 | 60 |
| starting | Average (%) | 100.72 | 101.99 | 101.81 | 101.89 | 102.05 | 102.35 | 102.29 |
| | SD | 3.48 | 3.11 | 3.16 | 3.01 | 2.99 | 2.96 | 3.08 |
| | RSD[%] | 3.44 | 3.04 | 3.10 | 2.95 | 2.93 | 2.89 | 3.00 |
| 2 weeks 40° C./75% RH | Average (%) | 101.56 | 103.00 | 102.85 | 102.83 | 103.02 | 102.85 | 102.66 |
| | SD | 2.43 | 1.91 | 2.06 | 1.89 | 1.74 | 2.00 | 1.87 |
| | RSD[%] | 2.39 | 1.85 | 1.99 | 1.83 | 1.68 | 1.94 | 1.82 |
| 4 weeks 40° C./75% RH | Average (%) | 101.66 | 102.89 | 102.93 | 103.10 | 103.11 | 103.04 | 103.09 |
| | SD | 2.43 | 2.47 | 2.38 | 2.13 | 2.32 | 2.39 | 2.33 |
| | RSD[%] | 2.38 | 2.40 | 2.30 | 2.06 | 2.24 | 2.31 | 2.25 |

Example 20/B

Preparation of Vortioxetine Mandelate (Compound of the Formula IX) Containing Capsules (Strength: Corresponds to 20 mg of Vortioxetine Base)

One proceeds as described in steps a) and b) of Example 20A except that in step c) the homogenized mixture is not pressed to tablets but filled in soft gelatine capsules.

Example 21

Preparation of Vortioxetine Hydrobromide Containing Tablets (Strength: Corresponds to 20 mg of Vortioxetine Base)
Composition:

| | Name of the product: Vortioxetine 20 mg tablet | |
|---|---|---|
| Name of component | Batch number: 012 UA 1114 mg/tablet | Batch size: about 1 050 g weight (g) |
| Vortioxetine-hydrobromide ground | 25.42 | 177.94 |
| Microcrystalline cellulose (Avicel PH 101 (FMC)) | 14.212 | 99.48 |
| Mannitol (Pearlitol SD 200) | 92.768 | 649.38 |
| Sodium carboxymethyl cellulose (Primojel) | 4.500 | 31.5 |
| Hydroxypropyl cellulose (Klucel EXF) | 4.50 | 31.5 |
| Purified water | 0 | 493.5 |
| | 0 | 0 |
| Avicel PH 101 (FMC) | 7.10 | 49.7 |
| Magnesium stearate | 1.50 | 10.5 |
| | 0 | 0 |
| Total: | 150.0 | 1050 |

The tablets are prepared according to the process of example 20/A except that the components are used in the amounts corresponding to the above composition.

The chemical stability and dissolution of the tablets obtained is tested.

a) Chemical Stability of the Tablets Obtained:

| | | | Σ Total amount of impurities[%] (>0.03%) | | |
|---|---|---|---|---|---|
| Sample | Storing Conditions | Average content % | Σ total [%] | Σ known [%] | Σ unknown [%] |
| Tablet containing the HBr salt (012UA1114) | Starting | 98.20 | <0.03 | <0.03 | <0.03 |
| | 40° C./75RH %-2 weeks | 100.98 | <0.03 | <0.03 | <0.03 |
| | 40° C./75RH %-4 weeks | 102.77 | <0.03 | <0.03 | <0.03 |

(The results are calculated from two parallel measurements. The average value is expressed as a percentage of the theoretical content calculated from the measured value.)

It can be seen from the Table that the chemical stability of the tablets is excellent.

b) Dissolution Tests

Figure 14:
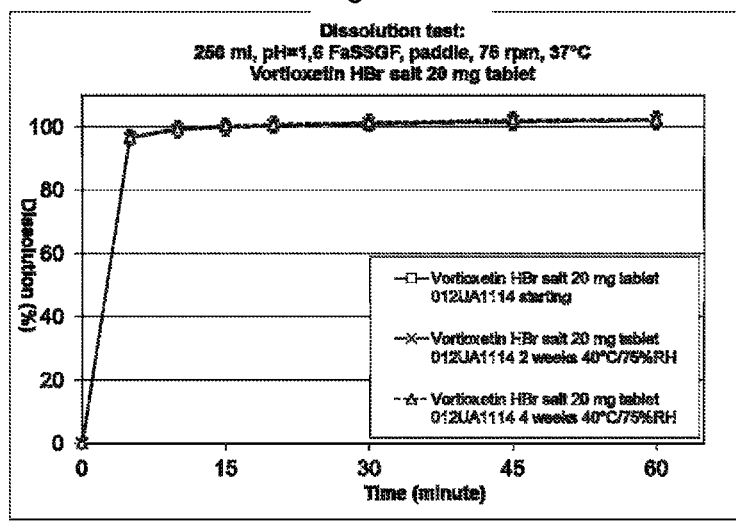
FIG. 14./Drawing 13: Dissolution curve of vortioxetine hydrogen bromide containing immediate release tablets (250 ml, pH 1.6 FaSSGF, paddle, 75 rpm, 37° C.) at the starting point of the test and 2 weeks and 4 weeks after storage (40° C./75% RH).

The dissolution of the tablets meets the requirements of the immediate release tablets. On the advancement of time the dissolution of the tablets does not significantly change as shown on Drawing 13 and FIG. 14.

| | | Time of sampling (minutes—dissolution (%)) | | | | | | |
|---|---|---|---|---|---|---|---|---|
| 012UA1114 | | 5 | 10 | 15 | 20 | 30 | 45 | 60 |
| Starting | Average (%) | 96.87 | 99.45 | 99.98 | 100.33 | 100.84 | 101.53 | 102.03 |
| | SD | 1.96 | 2.01 | 1.96 | 2.01 | 2.08 | 2.35 | 2.43 |
| | RSD[%] | 2.05 | 2.04 | 1.99 | 2.03 | 2.09 | 2.35 | 2.41 |
| 2 weeks 40° C./75% RH | Average (%) | 96.45 | 99.19 | 99.94 | 100.53 | 101.31 | 101.96 | 102.12 |
| | SD | 2.14 | 2.40 | 2.59 | 2.51 | 2.50 | 2.74 | 2.85 |
| | RSD[%] | 2.25 | 2.45 | 2.63 | 2.52 | 2.50 | 2.72 | 2.83 |
| 4 weeks 40° C./75% RH | Average (%) | 96.78 | 99.63 | 100.45 | 100.84 | 101.53 | 102.31 | 102.49 |
| | SD | 2.41 | 2.29 | 2.28 | 2.27 | 2.45 | 2.34 | 2.25 |
| | RSD[%] | 2.52 | 2.32 | 2.30 | 2.28 | 2.45 | 2.32 | 2.23 |

Example 22

Preparation of Tablets Containing Vortioxetine Hemicitrate of the Formula XI (Strength: Corresponds to 20 mg of Vortioxetine Base)
Composition:

| | Name of the product: Vortioxetine 20 mg tablet | |
|---|---|---|
| Weight of the component | Batch number: 013 UA 1114 mg/tablet | Batch size: ca. 1 050 g Weight (g) |
| Vortioxetine hemicitrate ground | 26.034 | 182.24 |
| Microcrystalline cellulose (Avicel PH 101 (FMC)) | 14.098 | 98.68 |
| Mannitol (Pearlitol SD 200) | 92.268 | 645.88 |
| Sodium carboxymethyl starch (Primojel) | 4.5 | 31.5 |
| Hydroxypropyl cellulose (Klucel EXF) | 4.5 | 31.5 |

-continued

| Weight of the component | Name of the product: Vortioxetine 20 mg tablet | |
|---|---|---|
| | Batch number: 013 UA 1114 mg/tablet | Batch size: ca. 1 050 g Weight (g) |
| Purified water | 0 0 | 493.5 0 |
| Avicel PH 101 (FMC) | 7.1 | 49.7 |
| Magnesium stearate | 1.5 0 | 10.5 0 |
| Total: | 150 | 1050 |

The tablets are prepared as described in example 20 except that the amount of the components corresponds to the above composition.

The chemical stability and the dissolution of the tablets obtained are tested.

a) Chemical Stability of the Tablets:

| | Impurity content expressed in the percentage of the active ingredient | | | |
|---|---|---|---|---|
| | | | Σ Total amount of impurities [%] (>0.03%) | |
| Sample | Storing conditions | Average content % | Σ total [%] | Σ known [%] | Σ unknown [%] |
| Hemicitrate containing tablets (013UA1114) | Starting | 97.03 | <0.03 | <0.03 | <0.03 |
| | 40° C./75RH %-2 weeks | 97.49 | <0.03 | <0.03 | <0.03 |
| | 40° C./75RH %-4 weeks | 95.93 | 0.03 | <0.03 | 0.03 |

(The results are calculated from two parallel measurements. The average content is expressed in the percentage of the theoretical content obtained from the measured value)

It can be seen from the Table that the chemical stability of the tablets is excellent.

b) Dissolution Test

The dissolution of the tablets meets the requirements of the immediate release tablets.

Figure 15:
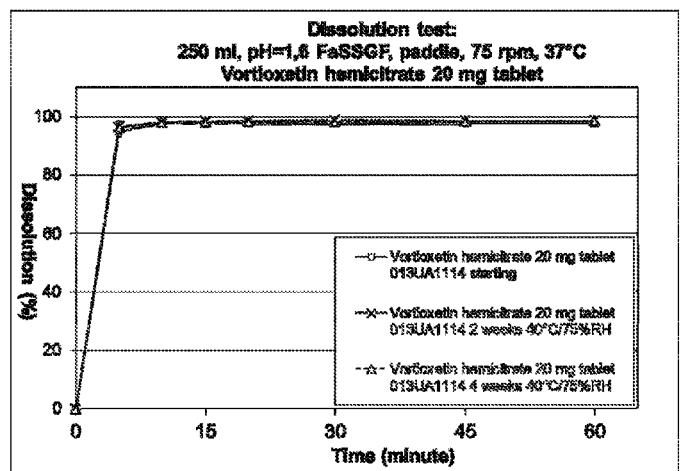
FIG. 15./Drawing 14: Dissolution curve of vortioxetine hemicitrate containing immediate release tablets (250 ml, pH 1.6 FaSSGF, paddle, 75 rpm, 37° C.) at the starting point of the test and 2 weeks and 4 weeks after storage (40° C./75% RH).

On advancement of time the dissolution of the tablets does not change significantly as shown on the following Drawing 14 and FIG. 15.

| | | Time of sampling (minutes—dissolution (%)) | | | | | | |
|---|---|---|---|---|---|---|---|---|
| 013UA1114 | | 5 | 10 | 15 | 20 | 30 | 45 | 60 |
| starting | Average (%) | 95.02 | 97.69 | 97.86 | 97.65 | 97.54 | 97.70 | 97.65 |
| | SD | 1.85 | 0.91 | 1.03 | 0.88 | 0.88 | 0.84 | 0.88 |
| | RSD[%] | 1.93 | 0.92 | 1.04 | 0.89 | 0.89 | 0.85 | 0.89 |
| 2 weeks 40° C./75% RH | Average (%) | 96.64 | 98.08 | 98.38 | 98.47 | 98.83 | 98.57 | 98.57 |
| | SD | 1.81 | 1.30 | 1.38 | 1.38 | 1.51 | 1.31 | 1.31 |
| | RSD[%] | 1.85 | 1.31 | 1.38 | 1.39 | 1.51 | 1.31 | 1.32 |
| 4 weeks 40° C./75% RH | Average (%) | 96.33 | 98.06 | 98.25 | 98.29 | 98.28 | 98.51 | 98.51 |
| | SD | 1.45 | 1.11 | 1.20 | 1.11 | 1.27 | 1.20 | 1.30 |
| | RSD[%] | 1.48 | 1.12 | 1.21 | 1.12 | 1.28 | 1.20 | 1.30 |

Example 23

Preparation of Tablets Containing Vortioxetine Monooxalate of the Formula X (Strength: Corresponds to 20 mg of Vortioxetine Base)
Composition:

| | Name of component: Vortioxetine 20 mg tablet | |
|---|---|---|
| Weight of the component | Batch number: 014 UA 1114 mg/tablet | Batch size: about 1 050 g Weight (g) |
| Vortioxetine monooxalate ground | 26.034 | 182.24 |
| Microcrystalline cellulose (Avicel PH 101 (FMC)) | 14.098 | 98.68 |
| Mannitol (Pearlitol SD 200) | 92.268 | 645.88 |
| Sodium carboxymethyl starch (Primojel) | 4.5 | 31.5 |
| Hydroxypropyl cellulose (Klucel EXF) | 4.5 | 31.5 |
| Purified water | 0 0 | 493.5 0 |
| Avicel PH 101 (FMC) | 7.1 | 49.7 |
| Magnesium stearate | 1.5 0 | 10.5 0 |
| Total: | 150 | 1050 |

The tablets are prepared according to the process of example 20 except that the components are used in an amount corresponding to the above composition.

The chemical stability and dissolution of the tablets obtained are tested:

a) Chemical Stability of the Tablets Obtained:

| | Amount of the impurity expressed in the percentage of the active ingredient | | | |
|---|---|---|---|---|
| | | | Σ Total impurities [%] (>0.03%) | |
| Sample | Storing conditions | Average content % | Σ total [%] | Σ known [%] | Σ unknown [%] |
| Monooxalate salt containing tablet (014UA1114) | Starting | 99.74 | <0.03 | <0.03 | <0.03 |
| | 40° C./75RH %-2 weeks | 98.42 | <0.03 | <0.03 | <0.03 |
| | 40° C./75RH %-4 weeks | 99.38 | <0.03 | <0.03 | <0.03 |

Figure 16:
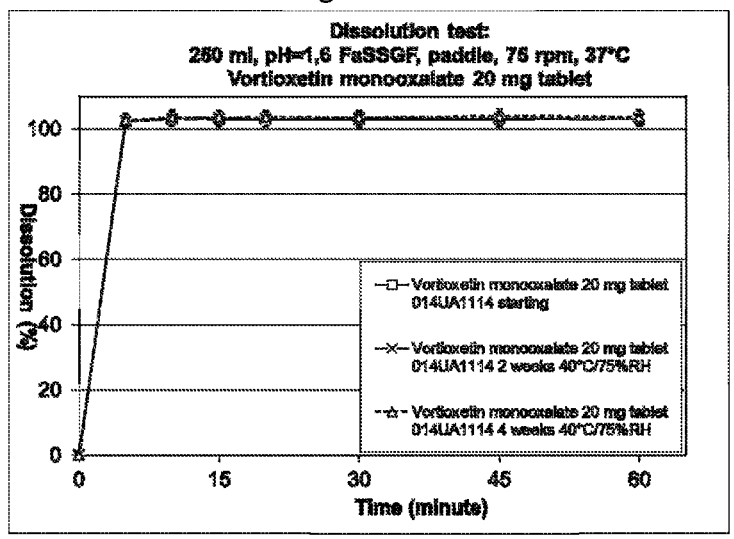
FIG. 16./Drawing 14: Dissolution curve of vortioxetine monooxaalate containing immediate release tablets (250 ml, pH 1.6 FaSSGF, paddle, 75 rpm, 37° C.) at the starting point of the test and 2 weeks and 4 weeks after storage (40° C./75% RH).
Figure 17:
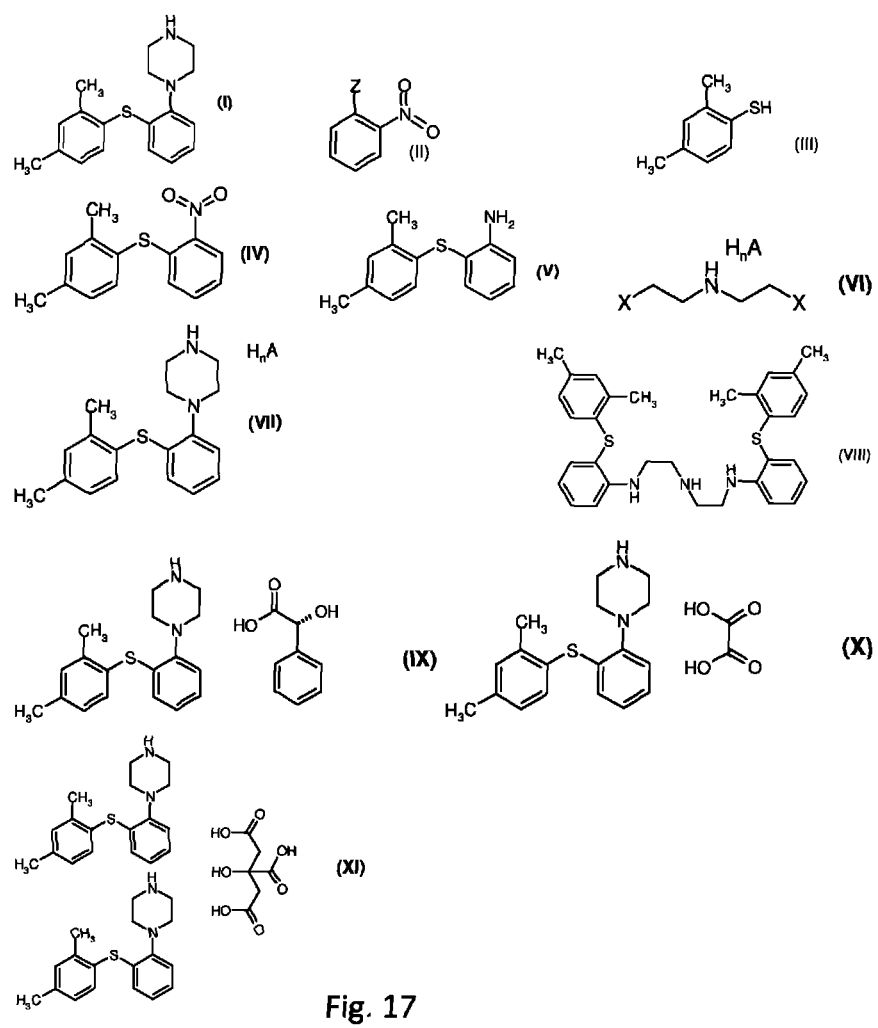
FIG. 17/Drawing 15: Formulae of the intermediates of the vortioxetine synthesis and of the most preferred salts.
Figure 18:
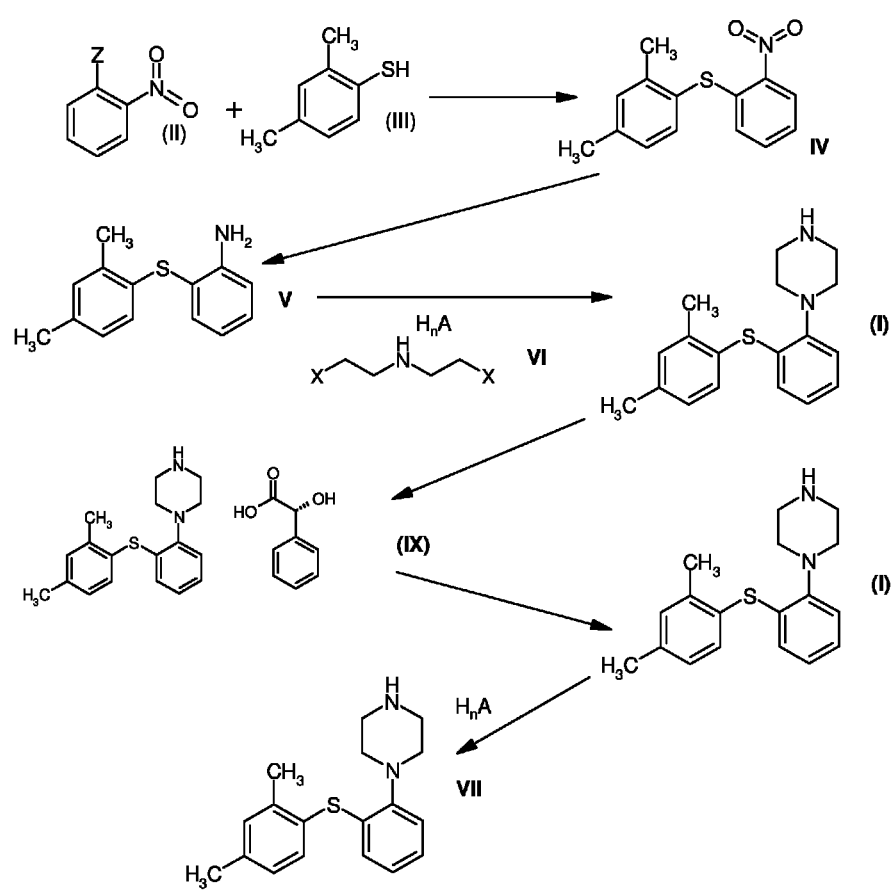
FIG. 18/Drawing 16: synthesis route of the vortioxetine mandelate salt and the other salts prepared from the mandelate.
Figure 19:
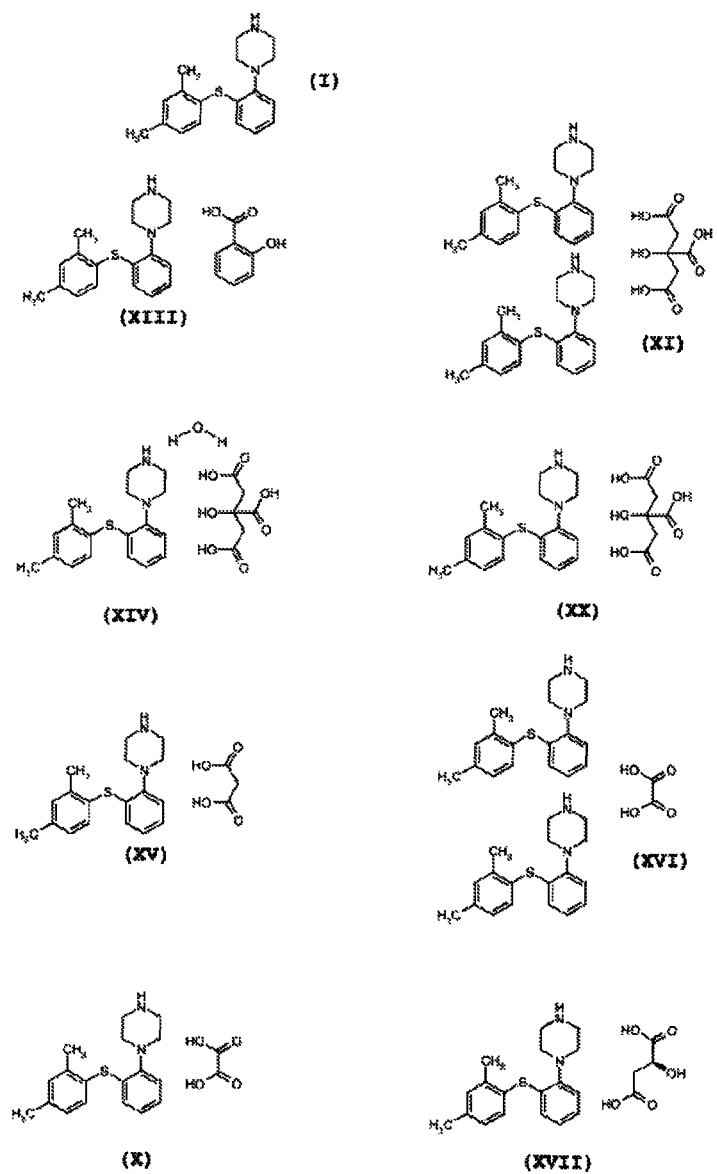
FIG. 19/Drawing 17: structural Formulae of the salts prepared according to the present invention.
Figure 20:
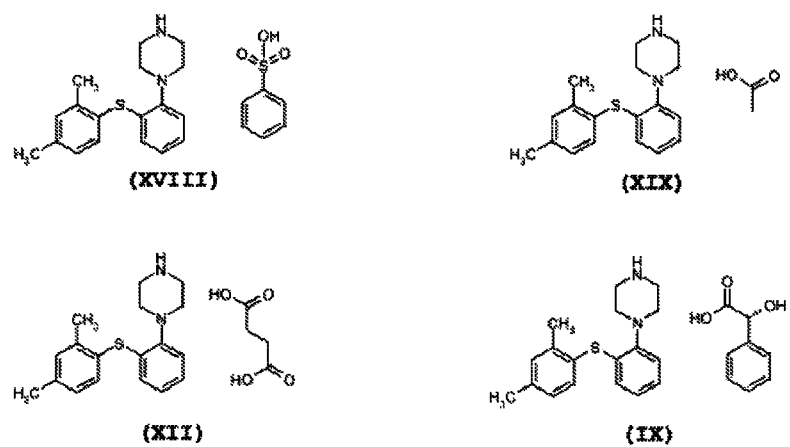
FIG. 20/Drawing 18: structural Formulae of the salts prepared according to the present invention.

(The results are calculated from 2 parallel measurements. The average content is expressed in % of the theoretical content calculated from the measured value.) It can be seen from the Table that the chemical stability of the tablets is excellent.

b) Dissolution Tests:

After storing the dissolution of the tablets meets the requirements of immediate release tablets. On advancement of time the dissolution of the tablets does not change significantly as shown in the following Table and on Drawing 14 and FIG. 16:

|  |  | \multicolumn{7}{c}{Time of sampling (minutes—dissolution (%))} |
|---|---|---|---|---|---|---|---|---|
| 014UA1114 |  | 5 | 10 | 15 | 20 | 30 | 45 | 60 |
| starting | Average (%) | 102.31 | 103.17 | 103.06 | 103.02 | 102.93 | 102.94 | 103.15 |
|  | SD | 2.14 | 2.34 | 2.39 | 2.24 | 2.33 | 2.34 | 2.31 |
|  | RSD[%] | 2.18 | 2.36 | 2.41 | 2.26 | 2.35 | 2.36 | 2.33 |
| 2 weeks 40° C./75% RH | Average (%) | 102.37 | 103.09 | 103.27 | 103.04 | 103.25 | 103.18 | 103.25 |
|  | SD | 2.09 | 2.12 | 2.14 | 2.16 | 2.14 | 2.18 | 2.17 |
|  | RSD[%] | 2.12 | 2.13 | 2.16 | 2.18 | 2.15 | 2.19 | 2.18 |
| 4 weeks 40° C./75% RH | Average (%) | 102.61 | 103.57 | 103.55 | 103.64 | 103.56 | 103.83 | 103.72 |
|  | SD | 2.07 | 2.18 | 2.07 | 1.99 | 2.12 | 2.17 | 2.03 |
|  | RSD[%] | 2.10 | 2.19 | 2.08 | 2.00 | 2.13 | 2.18 | 2.03 |

We claim:

1. A process for preparing a vortioxetine salt of Formula VII

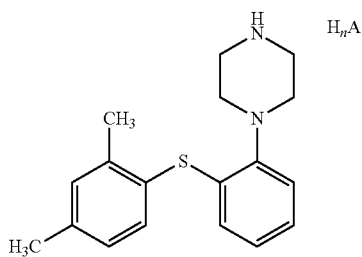
(VII)

comprising reacting a compound of Formula V

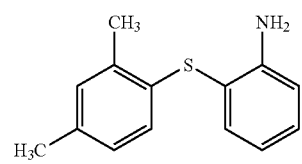
(V)

with a compound of Formula VI

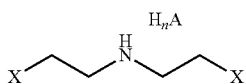
(VI)

wherein

X stands for chlorine, bromine, iodine, methanesulfonyloxy, p-toluenesulfonyloxy or hydroxy;

$H_nA$ represents an organic or inorganic mono- or polybasic acid,

A is an acid residue and n is the number of the hydrogen atoms, converting the resultant vortioxetine base of Formula I

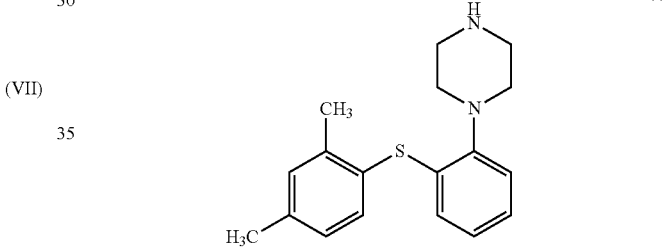
(I)

to form the L-(+)-mandelic acid salt of Formula IX,

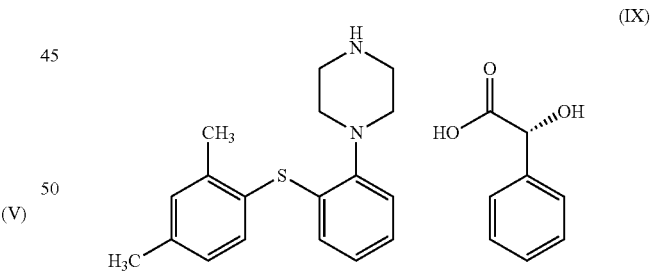
(IX)

optionally setting free the base from the salt, and converting the base to a salt of Formula VII wherein $H_nA$ stands for a mono-or polybasic organic or inorganic acid;

n is 1, 2 or 3, and

A represents an acid residue ion.

2. The process according to claim 1, which comprises carrying out the reaction of the compounds of Formulae V and VI in a solvent, which is an aromatic or aliphatic hydrocarbon, an ether, an acid amide, an urea derivative, a nitrile, an ester or a mixture thereof.

3. The process according to claim 1, which comprises carrying out the reaction of the compounds of Formulae V and VI in the presence of an organic or inorganic base.

4. The process according to claim 1, which comprises carrying out the reaction of the compounds of Formulae V and VI at 100-200° C. for 6-20 hours.

5. The process according to claim 1, which comprises isolating the vortioxetine base of Formula I after the reaction of the compounds of Formulae V and VI has been completed.

6. The process according to claim 1, which comprises isolating the vortioxetine base from the reaction mixture in form of a solution and adding to the solution containing the vortioxetine base a predetermined amount of L-(+)-mandelic acid and separating the precipitated L-(+)-mandelate salt from the solution.

7. The process according to claim 1, which comprises suspending the isolated crystalline vortioxetine L-(+)-mandelate salt thus obtained in water, adding to the mixture an aromatic solvent, a halogenated solvent or an ether solvent, adding to the mixture thus obtained an alkali or alkaline earth metal hydroxide or carbonate in an amount sufficient to make the pH of the aqueous phase alkaline, thereafter separating the organic phase and drying and evaporating and optionally subjecting the vortioxetine base thus obtained to the following steps:
  a) recrystallizing; or
  b) dissolving or suspending in a dipolar aprotic solvent, reacting with an organic acid, or a solution thereof formed with an organic solvent, or with an inorganic acid, or an aqueous solution thereof, and optionally recrystallizing the salts thus obtained; or
reacting the compounds of Formulae V and VI in a 1:2-2:1 weight ratio mixture of toluene and DMI in a closed vessel at 150-200° C., for 10-16 hours, cooling the mixture, filtering the precipitated inorganic salts, washing the united organic phases free from toluene, pouring the residue into an aqueous ammonium hydroxide solution, filtering the precipitated crystalline vortioxetine base, suspending in acetone, warming the suspension thus obtained to 60° C., adding a predetermined amount of an acetone solution of L-(+)-mandelic acid, cooling the mixture, separating the precipitated vortioxetine L-(+)-mandelate salt, suspending said salt in water, adding dichloromethane, making the aqueous phase alkaline with a potassium or sodium carbonate solution or an alkali hydroxide, separating the dichloro methane phase, drying and evaporating and optionally subjecting the vortioxetine base of Formula I to the following steps:
  a) allowing to crystallize or recrystallizing from acetonitrile; or
  b) crystallizing or recrystallizing the base of Formula I and/or suspending or dissolving said base in a dipolar aprotic solvent, adding at 60° C. a predetermined amount of salicylic acid, citric acid, malonic acid, oxalic acid, L-malic acid, benzenesulfonic acid, acetic acid, succinic acid or L-amygdalic acid dissolved in acetone or ethyl acetate, and thereafter separating the corresponding vortioxetine salt by cooling; or
reacting the compounds of Formulae V and VI in a 1:2-2:1 weight mixture of toluene and DMI, in a closed vessel, at 150-200° C., for 6-12 hours, thereafter adding to the reaction mixture a 2-15-fold amount of toluene, related to the volume of the reaction mixture, the mixture thus obtained is cooled, reacted with a sodium or potassium hydroxide solution, the organic phase is separated, optionally dried, warmed to 50-100° C., then a predetermined amount of L-(+)-mandelic acid is added, the mixture is allowed to cool, the precipitated crystals are filtered, dried, the L-(+)-mandelate salt thus obtained is optionally suspended in water, dichloro methane is added, the aqueous layer is made alkaline with potassium or sodium carbonate or an alkali hydroxide, the dichloro methane phase is separated, dried and evaporated, the vortioxetine base of the Formula I thus obtained is optionally
  a) allowed to crystallize or recrystallized from acetonitrile; or
  b) the base of Formula I is optionally crystallized or recrystallized by suspending and/or dissolving in a dipolar aprotic solvent, and adding to the mixture at 60° C. a predetermined amount of salicylic acid, citric acid, malonic acid, oxalic acid, L-malic acid, benzenesulfonic acid, acetic acid, succinic acid or L-amygdalic acid dissolved in acetone or ethyl acetate, and thereafter separating the corresponding vortioxetine salt by cooling; or
preparing the compound of Formula V by reacting the nitro compound of Formula II

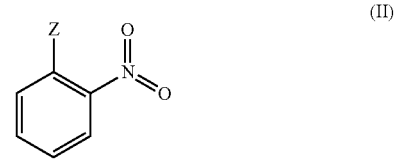

wherein Z stands for fluorine, chlorine, bromine or iodine, with the diol of Formula III

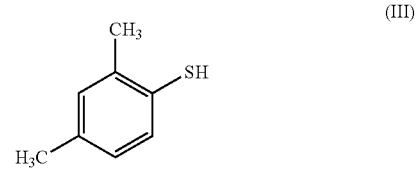

and reducing the compound of Formula IV thus obtained

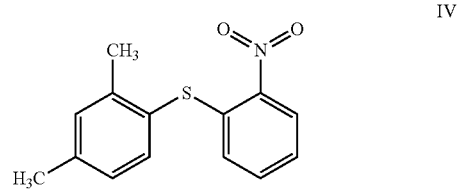 [SMILES: Cc1ccc(Sc2ccccc2[N+](=O)[O-])c(C)c1]

into the amine of the Formula V.

8. The process according to claim 7, which comprises carrying out the reaction of the compounds of Formulae V and VI in the presence of potassium or sodium carbonate.

9. A salt of the vortioxetine base of Formula I

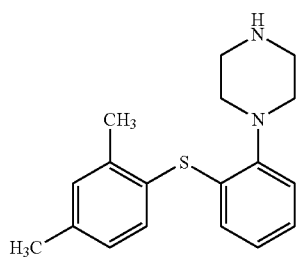
(I)

formed with salicylic acid, citric acid, malonic acid, oxalic acid, L-malic acid, benzenesulfonic acid, acetic acid, succinic acid or L-amygdalic acid of uniform morphology or a polymorph thereof.

10. The vortioxetine salt according to claim 9 having a HPLC purity larger than 99.5% and/or containing less than 0.5% of the impurity of the Formula VIII

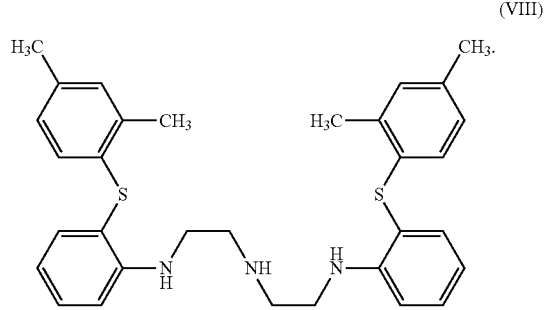 [SMILES: Cc1ccc(Sc2ccccc2NCCNCCNc2ccccc2Sc2ccc(C)cc2C)c(C)c1]
(VIII)

11. A polymorph of one of the following vortioxetine salts:

the polymorph of the vortioxetine succinic acid (1:1) salt of Formula XII

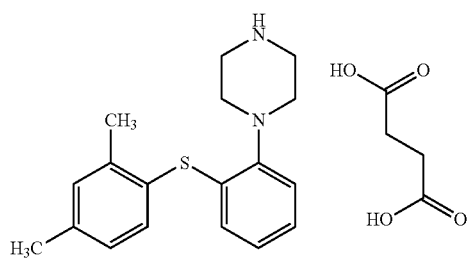
(XII)

having the following characteristic X-ray powder diffraction peaks: 2θ (±0.2°2θ): 11.33; 15.32; 17.03;17.91; 23.44; 24.00;

the polymorph of the vortioxetine salicylate salt of Formula XIII

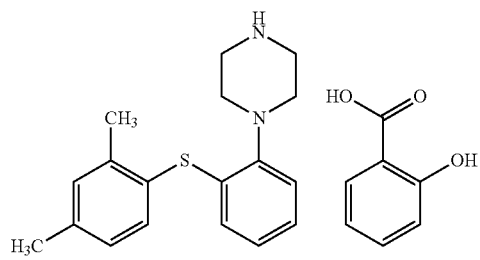
(XIII)

having the following characteristic X-ray powder diffraction peaks: 2θ (±0.2°2θ): 13.73; 14.39; 16.60; 16.84; 18.61;

the polymorph of the vortioxetine monocitrate monohydrate (1:1) salt of Formula XIV

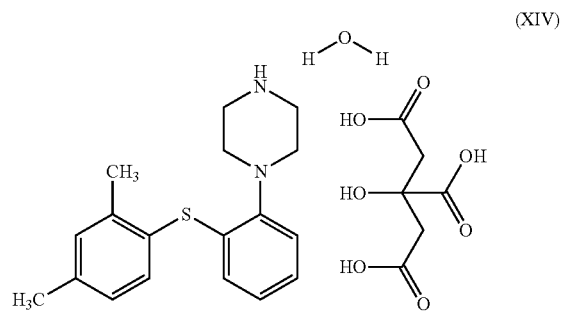
(XIV)

having the following xharacteristic X-ray powder diffraction peaks: 2θ (±0.2°2θ): 11.66; 13.89; 16.36; 17.00; 22.65; 24.09;

the polymorph of the vortioxetine monocitrate anhydrate (1:1) salt of Formula XX

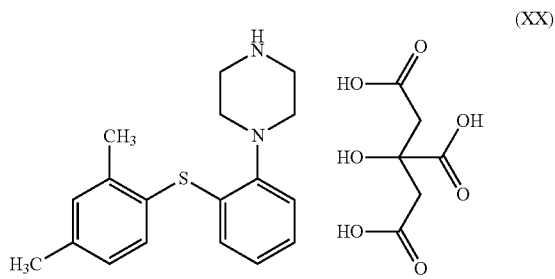 [SMILES: Cc1ccc(Sc2ccccc2N2CCNCC2)c(C)c1 ; O=C(O)CC(O)(CC(=O)O)C(=O)O]
(XX)

having the following characteristic powder X-ray powder diffraction peaks: 2θ (±0.2°2θ): 5.52; 12.38; 16.26; 16.61; 18.12; 20.89;

the polymorph of the vortioxetine malonate salt of Formula XV

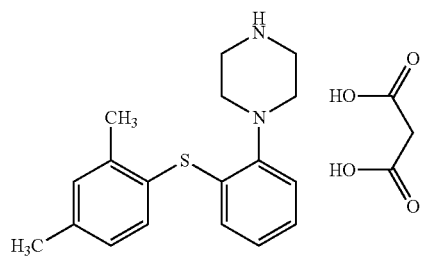
(XV)

having the following characteristic X-ray powder diffraction peaks: 2θ (±0.2°2θ): 5.11; 10.46; 11.93;15.21; 18.71; 20.42;

the polymorph of the vortioxetine hemioxalate (2:1) salt of Formula XVI

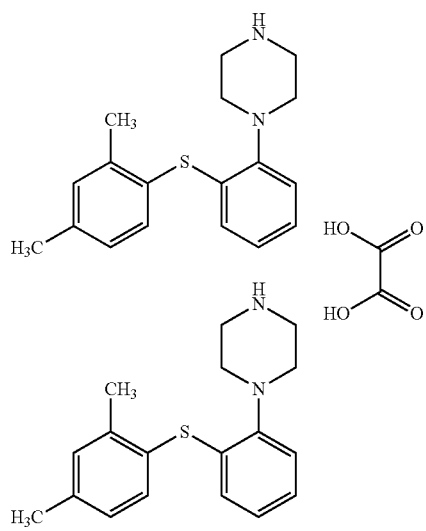
(XVI)

having the following characteristic X-ray powder diffraction peaks: 2θ (±0.2°2θ): 15.43; 16.32;

the polymorph of the vortioxetine L-malate (1:1) salt of Formula XVII

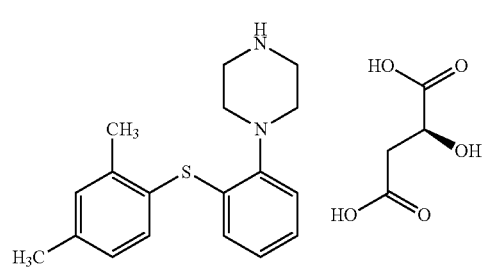
(XVII)

having the following characteristic X-ray powder diffraction peaks: 2θ (±0.2°2θ): 12.08; 13.4; 13.58;16.97; 19.58; 24.26;

the polymorph of the vortioxetine benzenesulfonate salt of Formula XVIII

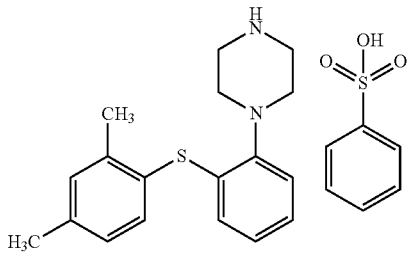
(XVIII)

having the following characteristic X-ray powder diffraction peaks: 2θ (±0.2°2θ): 14.79; 15.63; 17.61;18.51; 19.54; 23.53; or the polymorph of the vortioxetine acetate salt of Formula XIX

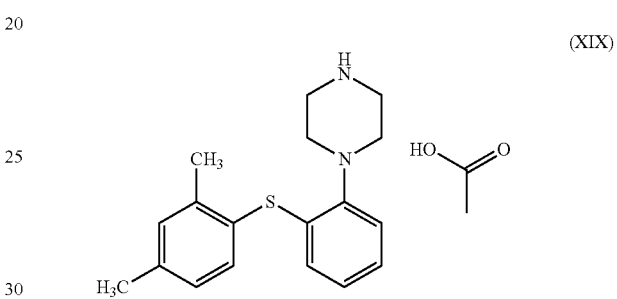
(XIX)

having the following characteristic X-ray powder diffraction peaks: 2θ (±0.2°2θ): 13.08; 14.06; 15.68; 18.26; 21.06; 22.44.

12. A pharmaceutical composition c mprising as active ingredient a morphologically uniform vortioxetine salt according to claim 9 formed with salicylic acid, citric acid, malonic acid, oxalic acid, L-malic acid, benzen sulfonic acid, acetic acid, succinic acid or L-mandelic acid or a polymorph thereof in admixi ure with at least one auxiliary agent.

13. The pharmaceutical composition according to claim 12 wherein the HPLC purity of the active ingredient is larger than 99.5% and/or contains less than 0.5% of the impurity of the Formula VIII

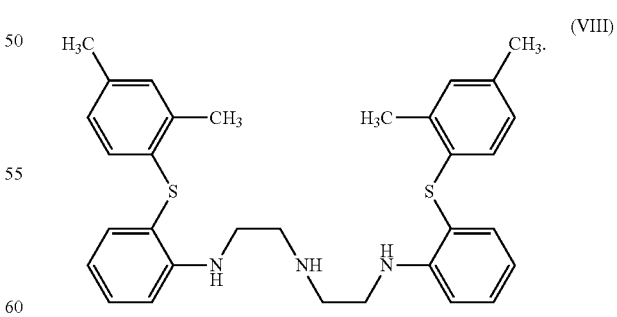
(VIII)

14. The process according to claim 1, which comprises carrying out the reaction of the compounds of Formulae V and VI in a solvent, which is toluene, xylene, ethyl benzene, pentane, hexane, cyclohexane, octane, petrolether, diethyl ether, diisopropyl ether, dibutyl ether, methyl tert-butyl ether, diethylene glycol dimethyl ether, diethylene glycol monoethyl ether, dimethyl- or diethyl-formamide, dimethyl- or diethyl-acetamide or propionamide, 1,3-dimethyl-2-imidazolidinone, ethyl acetate, propyl acetate, ethyl propionate, butyl acetate or a mixture thereof.

15. The process according to claim 1, which comprises carrying out the reaction of the compounds of Formulae V and VI in a solvent, which is a mixture of toluene and 1,3-dimethyl-2-imidazolidinone, wherein the ratio of toluene and 1,3-dimethyl-2-imidazolidinone is 5:1-1:5.

16. The process according to claim 1, which comprises carrying out the reaction of the compounds of Formulae V and VI in the presence of an organic or inorganic base, which is triethyl amine, N,N-diisopropyl ethyl amine, tributyl amine, N,N-dimethyl ethyl amine, pyridine or a pyridine derivative, or potassium carbonate.

17. The process according to claim 1, which comprises
isolating the vortioxetine base of Formula I after the reaction of the compounds of Formulae V and VI has been completed by
 a) evaporating the reaction mixture partially or completely, reacting the residue with an ammonium hydroxide or a potassium or sodium hydroxide solution, and separating the precipitated vortioxetine base from the liquid phase, or
 b) adding to the reaction mixture an apolar aprotic solvent in a 2-15-fold volume amount, related to the volume of the reaction mixture, cooling the mixture thus obtained, reacting with a sodium or potassium hydroxide solution, separating the
organic phase and optionally drying and evaporating said organic phase, and dissolving the vortioxetine base prepared according to a) or b) in a dipolar aprotic solvent, adding to the solution L-(+)-mandelic acid or a solution thereof formed with a dipolar aprotic solvent, isolating the salt and optionally recrystallizing the L-(+)-mandelate salt thus obtained from methanol or 2-propanol.

18. The process according to claim 1, which comprises
isolating the vortioxetine base from the reaction mixture in form of a solution and adding to the solution containing the vortioxetine base a predetermined amount of L-(+)-mandelic acid and separating the precipitated L-(+)-mandelate salt from the solution by
adding to the reaction mixture after the reaction has been completed toluene in a 2-15-fold volume amount, related to the volume of the reaction mixture, reacting the mixture thus obtained with a sodium or potassium hydroxide solution, separating the organic phase, optionally drying and heating to 50-100° C., adding a predetermined amount of L-(+)-mandelic acid, allowing the mixture to cool, separating the precipitated L-(+)-mandelate salt from the solution and optionally filtering and drying the precipitated crystals.

19. The process according to claim 1, which comprises
suspending the isolated crystalline vortioxetine L-(+)-mandelate salt thus obtained in water, adding to the mixture toluene, dichloro methane, diethyl ether or diisopropyl ether, adding to the mixture thus obtained an alkali or alkaline earth metal hydroxide or carbonate in an amount sufficient to make the pH of the aqueous phase alkaline, thereafter separating the organic phase and drying and evaporating and optionally subjecting the vortioxetine base thus obtained to the following steps:
 a) recrystallizing; or
 b) dissolving or suspending in acetonitrile or in acetone or in ethyl acetate, reacting with salicylic acid, citric acid, malonic acid, oxalic acid, L-malic acid, benzenesulfonic acid, acetic acid, succinic acid or L-mandelic acid or solution thereof formed with hydrogen bromide or an aqueous solution thereof with citric acid or oxalic acid or a solution thereof formed with acetone or ethyl acetate or with an aqueous hydrogen bromide solution and optionally recrystallizing the salts thus obtained; or reacting the compounds of Formulae V and VI in a 1:1 weight ratio mixture of toluene and DMI in a closed vessel at 170-180° C. for 12 hours, cooling the mixture, filtering the precipitated inorganic salts, washing the united organic phases free from toluene, pouring the residue into an aqueous ammonium hydroxide solution, filtering the precipitated crystalline vortioxetine base, suspending in acetone, warming the suspension thus obtained to 60° C., adding a predetermined amount of an acetone solution of L-(+)-mandelic acid, cooling the mixture, separating the precipitated vortioxetine L-(+)-mandelate salt , suspending said salt in water, adding dichloromethane, making the aqueous phase alkaline with a sodium or potassium hydroxide solution, separating the dichloro methane phase, drying and evaporating and optionally subjecting the vortioxetine base of Formula I to the following steps:
 a) allowing to crystallize or recrystallizing from acetonitrile; or
 b) crystallizing or recrystallizing the base of Formula I and/or suspending or dissolving said base in acetone or ethyl acetate, adding at 60° C. a predetermined amount of citric acid or oxalic acid or an aqueous hydrogen bromide solution and thereafter separating the corresponding vortioxetine salt by cooling; or reacting the compounds of Formulae V and VI in a 1:1 weight mixtur of toluene and DMI, in a closed vessel, at 170-180° C. for 6-12 hours, thereafter adding to the reaction mixture a 5 fold amount of toluene, related to the volume of the reaction mix re, the mixture thus obtained is cooled, reacted with a sodium or potassium hydroxide solution, the organic phase is separated, optionally dried, warmed to 55-65° C., then a predetermine amount of L-(+)-mandelic acid is added, the mixture is allowed to cool, the precipitated c stals are filtered, dried, the L-(+)-mandelate salt thus obtained is optionally suspended in water, dichloro methane is added, the aqueous layer is made alkaline with a sodium potassium or potassium hydroxide solution, the dichloro methane phase is separated, dried nd evaporated, the vortioxetine base of the Formula I thus obtained is optionally
 a) allowed to crystallize or recrystallized from acetonitrile; or
 b) the base of Formula I is optionally crystallized or recrystallizeu by suspending and/or dissolving in acetone or ethyl acetate and adding to the mixture at 60° C. a predetermined amount of citric acid or oxalic acid or an aqueous hydrogen bromide solution and thereafter separating the corresponding vortioxetine salt by cooling;

or preparing the compound of Formula V by reacting the nitro compouni of Formula II

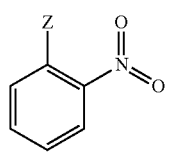

(II)

wherein Z stands for fluorine, chlorine, bromine or iodine, with the diol of Formula III

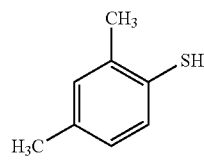

(III)

and reducing the compound of Formula IV thus obtained

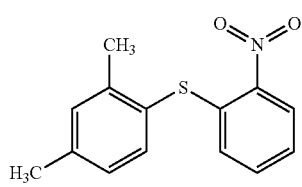

IV into the amine of the Formula V.

20. A salt of the vortioxetine base of Formula I according to claim 9, which is the vortioxetine salicylate salt of Formula XIII,

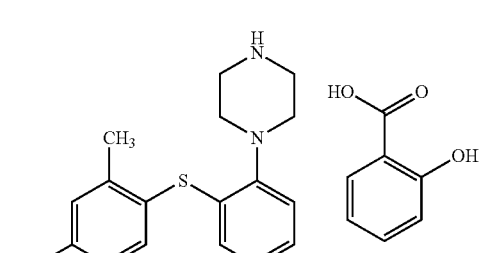

(XIII)

the vortioxetine monocitrate anhydrate salt of Formula XX,

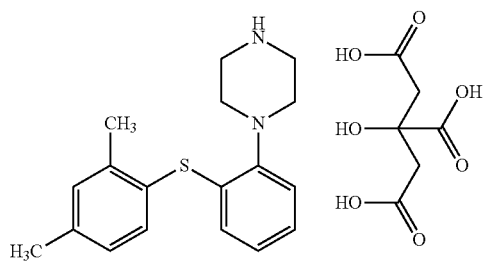

(XX)

the vortioxetine monocitrate hydrate salt of Formula XIV,

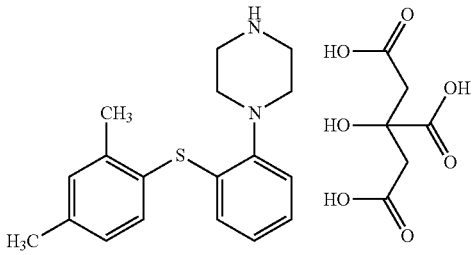

(XIV)

the vortioxetine hemicitrate salt of Formula XI,

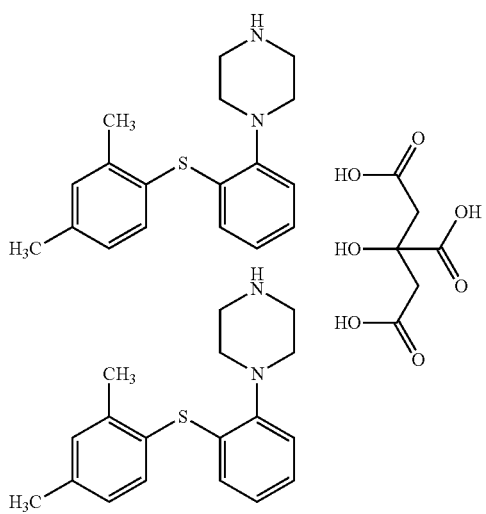

(XI)

the vortioxetine malonate salt of Formula XV,

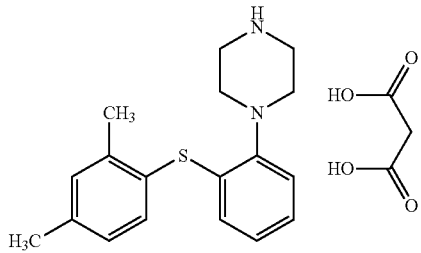

(XV)

the vortioxetine hemioxalate salt of Formula XVI,

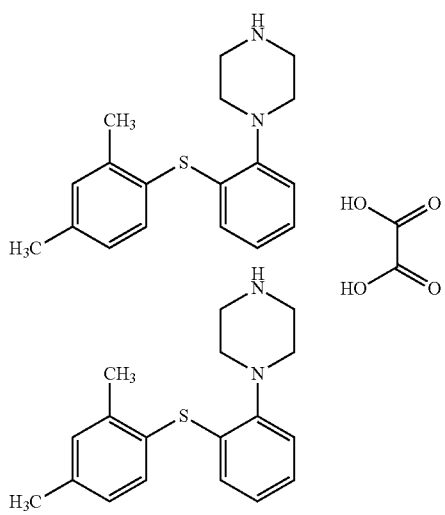

the vortioxetine monooxalate salt of Formula X,

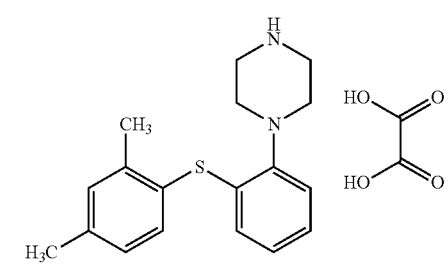

the vortioxetine malate salt of Formula XVII,

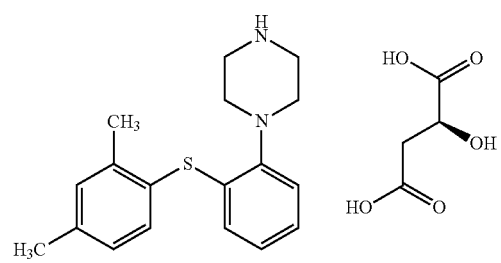

the vortioxetine benzenesulfonate salt of Formula XVIII,

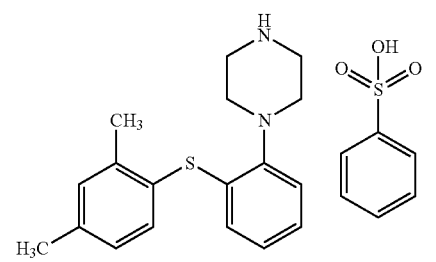

the vortioxetine acetic acid salt of Formula XIX,

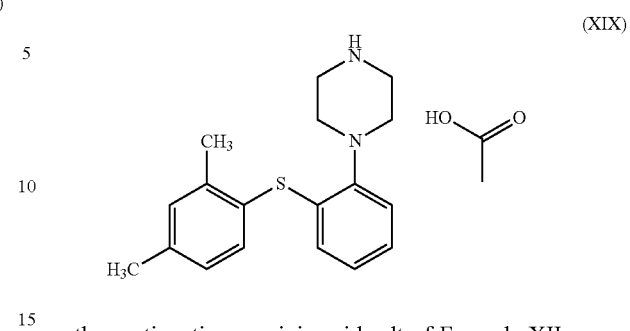

the vortioxetine succinic acid salt of Formula XII

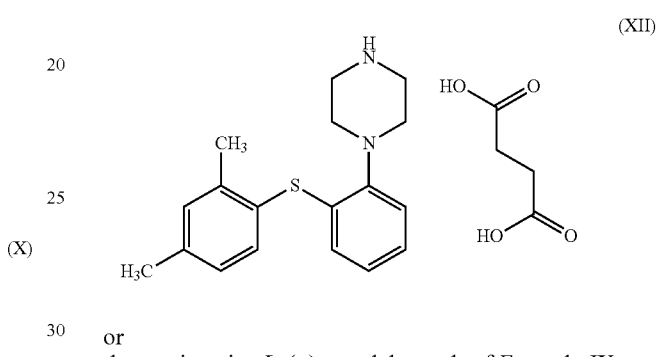

or
the vortioxetine L-(+)-mandelate salt of Formula IX

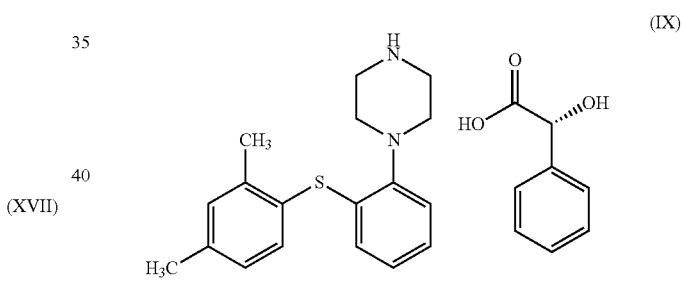

or a polymorph thereof.

21. A pharmaceutical composition comprising as active ingredient a morphologically uniform vortioxetine salt according to claim 20, which is the vortioxetine salicylate salt of the Formula XIII, the vortioxetine monocitrate anhydrate salt of the Formula XX, the vortioxetine monocitrate hydrate salt of the Formula XIV, the vortioxetine hemicitrate salt of the Formula XI, the vortioxetine malonate salt of the Formula XV, the vortioxetine hemioxalate salt of the Formula XVI, the vortioxetine monooxalate salt of the Formula X, the vortioxetine malate salt of the Formula XVII, the vortioxetine henzenesulfonate salt of the Formula XVIII, the vortioxetine acetic acid salt of the Formula XIX, the vortioxetine succinic acid salt of the Formula XII or the vortioxetine L-(+)-mandelate salt of the Formula IX or a polymorph thereof in admixture with at least one auxiliary agent.

22. Pharmaceutical composition according to claim 12, which comprises one of the following active ingredients:
polymorph of the vortioxetine L-(+)-mandelate salt having the following characteristic X-ray powder diffraction peaks: 2θ (±0.2°2 θ): 4.25; 11.69; 11.86; 13.29; 16.52; 16.93; 17.17; 18.47; 23.46; 24.29; 26.21;

polymorph of the vortioxetine-hemicitrate (2:1) salt having the following characteristic X-ray powder diffraction peaks: 2θ (±0.2° 2θ): 5.24; 13.79; 16.52; 17.31; 18.15; 20.35; or polymorph of the vortioxetine monooxalate (1:1) salt having the following characteristic X-ray powder diffraction peaks: 2θ (±0.2° 2θ): 14.48; 17.8; 18.97; 20.38; 23.87; 27.57;

and/or which comprises as auxiliary agent a filler and optionally a glidant, an antiadhesive, a hinder, a disintegrant and a lubricant.

23. The polymorph of the morphologically uniform vortioxetine L-(+)-mandelate salt of Formula IX according to claim 20 having the following characteristic powder diffraction peaks: 2θ (±0.2°2θ): 11.86; 13.29; 16.52; 16.93; 17.17; 23.46;

and/or having the following characteristic X-ray powder diffraction peaks: 2θ (±0.2°2θ): 4.25; 11.69; 11.86; 13.29; 16.52; 16.93; 17.17; 18.47; 23.46; 24.29; 26.21.

24. The polymorph of the vortioxetine L-(+)-mandelate salt according to claim 23 having the characteristic X-ray powder diffraction data disclosed in the following Table:

| Peak | 2θ (°) | d (Å) | Relative intensity (%) |
|---|---|---|---|
| 1 | 4.25 | 20.76 | 16 |
| 2 | 11.69 | 7.56 | 22 |
| 3 | 11.86 | 7.46 | 24 |
| 4 | 12.25 | 7.22 | 10 |
| 5 | 13.29 | 6.66 | 32 |
| 6 | 14.42 | 6.14 | 16 |
| 7 | 16.52 | 5.36 | 65 |
| 8 | 16.93 | 5.23 | 100 |
| 9 | 17.17 | 5.16 | 26 |
| 10 | 17.58 | 5.04 | 11 |
| 11 | 18.47 | 4.8 | 17 |
| 12 | 18.81 | 4.71 | 2 |
| 13 | 19.54 | 4.54 | 7 |
| 14 | 20.55 | 4.32 | 2 |
| 15 | 20.78 | 4.27 | 5 |
| 16 | 22.18 | 4 | 2 |
| 17 | 22.39 | 3.97 | 2 |
| 18 | 23.15 | 3.84 | 9 |
| 19 | 23.46 | 3.79 | 38 |
| 20 | 23.94 | 3.71 | 15 |
| 21 | 24.29 | 3.66 | 18 |
| 22 | 24.59 | 3.62 | 5 |
| 23 | 24.95 | 3.57 | 4 |
| 24 | 25.42 | 3.5 | 8 |
| 25 | 26.21 | 3.4 | 24 |
| 26 | 26.93 | 3.31 | 13 |
| 27 | 28.28 | 3.15 | 5 |
| 28 | 28.71 | 3.11 | 3 |
| 29 | 29 | 3.08 | 3 |
| 30 | 30.18 | 2.96 | 3 |
| 31 | 31.32 | 2.85 | 4 |
| 32 | 31.82 | 2.81 | 2 |
| 33 | 32.58 | 2.75 | 3 |
| 34 | 33.1 | 2.7 | 2 |
| 35 | 33.36 | 2.68 | 2. |

25. The polymorph of the vortioxetine hemicitrate (2:1) salt of the Formula XI according to claim 20 having the following characteristic X-ray powder diffraction peaks: 2θ (±0.2°2θ): 5.24; 13.79; 16.52; 17.31; 18.15; 20.35;

and/or having the following characteristic X-ray powder diffraction peaks: 2θ (±0.2°2θ): 5.24; 13.79; 15.76; 16.52; 17.31; 17.65; 18.15; 20.35; 20.6; 21.00; 23.01.

26. The polymorph of the vortioxetine hemicitrate (2:1) salt according to claim 25 having the characteristic X-ray powder diffraction data disclosed in the following Table:

| Peak | 2θ (°) | d (Å) | Relative intensity (%) |
|---|---|---|---|
| 1 | 5.24 | 16.85 | 100 |
| 2 | 10.26 | 8.61 | 36 |
| 3 | 10.5 | 8.41 | 10 |
| 4 | 10.94 | 8.08 | 9 |
| 5 | 11.43 | 7.74 | 14 |
| 6 | 12.1 | 7.31 | 16 |
| 7 | 13.02 | 6.8 | 21 |
| 8 | 13.79 | 6.41 | 93 |
| 9 | 14.28 | 6.2 | 8 |
| 10 | 14.67 | 6.03 | 10 |
| 11 | 15.76 | 5.62 | 41 |
| 12 | 16.52 | 5.36 | 73 |
| 13 | 17.31 | 5.12 | 48 |
| 14 | 17.65 | 5.02 | 39 |
| 15 | 18.15 | 4.88 | 50 |
| 16 | 18.77 | 4.72 | 27 |
| 17 | 19.04 | 4.66 | 13 |
| 18 | 20.01 | 4.43 | 21 |
| 19 | 20.35 | 4.36 | 53 |
| 20 | 20.6 | 4.31 | 44 |
| 21 | 21 | 4.23 | 40 |
| 22 | 21.45 | 4.14 | 21 |
| 23 | 22 | 4.04 | 14 |
| 24 | 23.01 | 3.86 | 42 |
| 25 | 23.2 | 3.83 | 31 |
| 26 | 24.31 | 3.66 | 13 |
| 27 | 24.71 | 3.6 | 15 |
| 28 | 25.12 | 3.54 | 11 |
| 29 | 25.39 | 3.51 | 10 |
| 30 | 25.85 | 3.44 | 18 |
| 31 | 26.37 | 3.38 | 17 |
| 32 | 26.71 | 3.34 | 4 |
| 33 | 27.3 | 3.26 | 5 |
| 34 | 27.75 | 3.21 | 18 |
| 35 | 28.22 | 3.16 | 3 |
| 36 | 28.84 | 3.09 | 6 |
| 37 | 30 | 2.98 | 6 |
| 38 | 31.07 | 2.88 | 7. |

27. The polymorph of the vortioxetinc monooxalate (1:1) salt of the Formula X according to claim 20 having the following characteristic X-ray powder diffraction data: 2θ (±0.2°2θ): 14.48; 17.8; 18.97; 20.38; 23.87; 27.57;

and/or having the following characteristic X-ray powder diffraction data 2θ (±0.2°2θ): 13.67; 14.48; 16.01; 17.8; 18.15; 18.46; 18.97; 20.38; 23.87; 27.57; 28.15.

28. The polymorph of the vortioxetine monooxalate (1:) salt according to claim 27 having the characteristic X-ray powder diffraction data disclosed in the following table:

| Peak | 2θ (°) | d (Å) | Relative intensity (%) |
|---|---|---|---|
| 1 | 10.16 | 8.7 | 9 |
| 2 | 13.67 | 6.47 | 41 |
| 3 | 14.48 | 6.11 | 96 |
| 4 | 15.38 | 5.76 | 3 |
| 5 | 16.01 | 5.53 | 28 |
| 6 | 16.98 | 5.22 | 8 |
| 7 | 17.8 | 4.98 | 51 |

-continued

| Peak | 2θ (°) | d (Å) | Relative intensity (%) |
|---|---|---|---|
| 8 | 18.15 | 4.88 | 32 |
| 9 | 18.46 | 4.8 | 18 |
| 10 | 18.97 | 4.67 | 100 |
| 11 | 19.54 | 4.54 | 7 |
| 12 | 20.38 | 4.36 | 48 |
| 13 | 21.1 | 4.21 | 10 |
| 14 | 21.72 | 4.09 | 3 |
| 15 | 22.16 | 4.01 | 4 |
| 16 | 22.75 | 3.91 | 3 |
| 17 | 23.16 | 3.84 | 10 |
| 19 | 24.36 | 3.65 | 5 |
| 20 | 24.89 | 3.57 | 2 |
| 21 | 25.35 | 3.51 | 3 |
| 22 | 26.1 | 3.41 | 6 |
| 23 | 26.81 | 3.32 | 16 |
| 24 | 27.15 | 3.28 | 4 |
| 25 | 27.57 | 3.23 | 57 |
| 26 | 28.15 | 3.17 | 29 |
| 27 | 29.32 | 3.04 | 10 |
| 28 | 29.73 | 3 | 3 |
| 29 | 30.65 | 2.91 | 2 |
| 30 | 31.63 | 2.83 | 8 |
| 31 | 31.96 | 2.8 | 3 |
| 32 | 32.33 | 2.77 | 12 |
| 33 | 32.74 | 2.73 | 3 |
| 34 | 33.37 | 2.68 | 4 |
| 35 | 34.44 | 2.6 | 10. |

\* \* \* \* \*